US008202509B2

(12) United States Patent
McBride et al.

(10) Patent No.: US 8,202,509 B2
(45) Date of Patent: Jun. 19, 2012

(54) METHODS AND COMPOSITIONS FOR IMPROVED F-18 LABELING OF PROTEINS, PEPTIDES AND OTHER MOLECULES

(75) Inventors: William J. McBride, Boonton, NJ (US); Christopher A. D'Souza, Pomona, NY (US); David M. Goldenberg, Mendham, NJ (US)

(73) Assignee: Immunomedics, Inc., Morris Plains, NJ (US)

(*) Notice: Subject to any disclaimer, the term of this patent is extended or adjusted under 35 U.S.C. 154(b) by 0 days.

(21) Appl. No.: 12/958,889

(22) Filed: Dec. 2, 2010

(65) Prior Publication Data
US 2011/0110854 A1 May 12, 2011

Related U.S. Application Data

(63) Continuation-in-part of application No. 12/433,212, filed on Apr. 30, 2009, which is a continuation-in-part of application No. 12/343,655, filed on Dec. 24, 2008, now Pat. No. 7,993,626, which is a continuation-in-part of application No. 12/112,289, filed on Apr. 30, 2008, now Pat. No. 7,563,433, which is a continuation-in-part of application No. 11/960,262, filed on Dec. 19, 2007, now Pat. No. 7,597,876.

(60) Provisional application No. 60/884,521, filed on Jan. 11, 2007, provisional application No. 61/266,773, filed on Dec. 4, 2009, provisional application No. 61/302,280, filed on Feb. 8, 2010, provisional application No. 61/316,125, filed on Mar. 22, 2010, provisional application No. 61/347,486, filed on May 24, 2010, provisional application No. 61/381,720, filed on Sep. 10, 2010, provisional application No. 61/388,268, filed on Sep. 30, 2010.

(51) Int. Cl.
*A61K 51/00* (2006.01)
*A61M 36/14* (2006.01)

(52) U.S. Cl. ............ 424/1.89; 424/1.11; 424/1.49; 424/1.65; 424/1.69; 424/1.81; 424/1.85

(58) Field of Classification Search ........... 424/1.11, 424/1.53, 1.65, 1.69, 1.73, 1.81, 1.85, 1.89, 424/9.1, 9.2, 9.3, 9.4, 9.5, 9.6, 9.7, 9.8, 1.49; 514/1.1; 530/300, 333, 338; 534/7, 10–16
See application file for complete search history.

(56) References Cited

U.S. PATENT DOCUMENTS

| 5,256,395 | A | 10/1993 | Barbet et al. |
| 5,446,147 | A | 8/1995 | Kung et al. |
| 6,056,939 | A | 5/2000 | Desreux et al. |
| 6,207,858 | B1 | 3/2001 | Chinn et al. |
| 6,605,615 | B2 | 8/2003 | Medina et al. |
| 6,838,073 | B1 | 1/2005 | Collins et al. |
| 6,953,567 | B2 | 10/2005 | Griffiths et al. |
| 7,011,816 | B2 | 3/2006 | Griffiths et al. |
| 7,081,452 | B2 | 7/2006 | Brechbiel et al. |
| 7,163,935 | B2 | 1/2007 | Brechbiel et al. |
| 7,563,433 | B2 * | 7/2009 | McBride et al. ............ 424/1.89 |
| 7,597,876 | B2 * | 10/2009 | McBride et al. ............ 424/1.89 |
| 7,993,626 | B2 * | 8/2011 | McBride et al. ............ 424/1.89 |
| 2002/0006379 | A1 | 1/2002 | Hansen et al. |
| 2003/0064523 | A1 | 4/2003 | Popov et al. |
| 2005/0112060 | A1 | 5/2005 | White et al. |
| 2005/0136001 | A1 | 6/2005 | McBride et al. |
| 2006/0140858 | A1 | 6/2006 | Goldenberg et al. |
| 2006/0228300 | A1 | 10/2006 | Chang et al. |
| 2008/0027220 | A1 | 1/2008 | Stossel et al. |
| 2008/0038191 | A1 | 2/2008 | Perrin et al. |
| 2008/0089838 | A1 | 4/2008 | Hansen et al. |
| 2008/0170989 | A1 | 7/2008 | McBride et al. |
| 2008/0253964 | A1 | 10/2008 | McBride et al. |
| 2009/0246130 | A1 | 10/2009 | McBride et al. |
| 2009/0299033 | A1 | 12/2009 | McBride et al. |

FOREIGN PATENT DOCUMENTS

| WO | 2007027385 | 3/2007 |
| WO | 2008088648 | 7/2008 |

OTHER PUBLICATIONS

Cai et al., "Chemistry with [18F]Fluoride Ion", Eur. J. Org. Chem. 2008, pp. 2853-2873.
Clark et al., "The Preparation of Fluorine-18 Labelled Compounds Using a Recirculatory Neon Target", Radiochem. Radioanal. Letters 14(2):101-108 (1973).
Imahori et al., "Fluorine-18-Labeled Fluoroboronophenylalanine PET in Patients with Glioma", J Nucl Med 1998; 39:325-333.
Karacay et al., "18F labeling of a peptide for PET imaging of receptor-expressing tumors", Abstract # 1567, 2009 SNM Annual Meeting Scientific Abstracts 50(Suppl. 2), p. 318P, May 2009.
Mamat et al., "Recent Applications of Click Chemistry for the Synthesis of Radiotracers for Molecular Imaging", Mini-Reviews in Organic Chemistry, 2009, vol. 6, pp. 21-34.
Marik et al., "Click for PET: rapid preparation of [18F]fluoropeptides using CuI catalyzed 1,3-dipolar cycloaddition", Tetrahedron Letters 47 (2006) 6681-6684.
McBride et al., "A new method of labeling peptides and proteins with F-18 via a metal ligand", Abstract #384, J Nucl Med. 2008; 49 (Supplement 1):97P.
McBride et al., "A new method of labeling peptides and proteins with F-18 via a metal ligand", PowerPoint Presentation, 55th SNM Annual Meeting, New Orleans, LA, Jun. 17, 2008.

(Continued)

*Primary Examiner* — D L Jones
(74) *Attorney, Agent, or Firm* — Richard A. Nakashima

(57) ABSTRACT

The present application discloses compositions and methods of synthesis and use of $^{68}$Ga, $^{18}$F or $^{19}$F labeled molecules of use in PET or MRI imaging. Preferably, the $^{18}$F or $^{19}$F is conjugated to a targeting molecule by formation of a complex with a group IIIA metal and binding of the complex to a chelating moiety, which may be directly or indirectly attached to the targeting molecule. In other embodiments, the $^{68}$Ga, $^{18}$F or $^{19}$F labeled moiety may comprise a targetable construct used in combination with a bispecific antibody to target a disease-associated antigen. In more preferred embodiments, a chelating moiety or targetable construct may be conjugated to a targeting molecule, such as an antibody or antibody fragment.

54 Claims, 15 Drawing Sheets

OTHER PUBLICATIONS

McBride et al., "A New Method of Labeling Peptides with F-18 Via a Metal Ligand", Abstract #04, Cancer Biother Radiopharm Aug. 2008; 23(4): 514.

McBride et al., "A New Method of Labeling Peptides with F-18 Via a Metal Ligand", PowerPoint Presentation, 19th Winter Fluorine Conference, St. Pete Beach, FL, Jan. 13, 2009.

McBride et al., "A New Method of Labeling Peptides with F-18 Via a Metal Ligand", Abstract #68, 19th Winter Fluorine Conference (Jan. 11-16, 2009) Abstract Book, p. 32.

McBride et al., "A novel method of radiolabeling peptides with aluminium-fluoride-18 (AlF-18) using various NOTA derivatives", Abstract # 202, 2009 SNM Annual Meeting Scientific Abstracts 50(Suppl. 2), pp. 52P-53P, May 2009.

Miller et al., "Synthesis of 11C, 18F, 15O, and 13N Radiolabels for Positron Emission Tomography", Angew. Chem. Int. Ed. 2008, vol. 47, pp. 8998-9033.

Murata et al., "Formation of the Stable Myosin-ADP-Aluminum Fluoride and Myosin-ADP-Beryllium Fluoride Complexes and Their Analysis Using 19F NMR", J. Biol. Chem. 268(10):7093-7100 (1993).

Schirrmacher et al., "Recent Developments and Trends in 18F-Radiochemistry: Syntheses and Applications" Mini-Reviews in Organic Chemistry, 2007, vol. 4, pp. 317-329.

Schoffelen et al., "Pretargeted immunoPET for imaging colorectal cancer in a mouse model", Abstract # 381, 2009 NM Annual Meeting Scientific Abstracts 50(Suppl. 2), pp. 100P, May 2009.

Ting et al., "Toward [18F]-Labeled Aryltrifluoroborate Radiotracers: In Vivo Positron Emission Tomography Imaging of Stable Aryltrifluoroborate Clearance in Mice", J. Am. Chem. Soc. 2008, 130, 12045-12055.

Ting et al., "Arylfruoroborates and Alkylfluorosilicates as Potential PET Imaging Agents: High-Yielding Aqueous Biomolecular 18F-Labeling", J. Am. Chem. Soc. 2005, 127, 13094-13095.

Wagner, Henry N. "Advancing a Molecular Theory of Disease", J Nulc Med 49(8):15N-34N. (2008).

Wester et al., "Fluorine-18 Labeling of Peptides and Proteins", Review, Ernst Schering Res. Found. Workshop 62:79-111 (2007).

International Search Report for PCT/US10/58724, filed Dec. 2, 2010. Date of mailing Apr. 6, 2011.

* cited by examiner

FIG. 1

| | %ID/g [F-18]-FDG | | %ID/g pretargeted Al[F-18] IMP 449 | | %ID/g Al[F-18] IMP 449 alone |
|---|---|---|---|---|---|
| Tumor | 7.91 | | 3.01 | | 0.09 |
| (weight (g)) | (0.056) | | (0.021) | | (0.082) |
| Liver | 1.03 | | 0.08 | | 0.13 |
| Spleen | 3.05 | | 0.05 | | 0.06 |
| Kidneys | 1.62 | | 2.01 | | 2.67 |
| Lungs | 4.98 | | 0.06 | | 0.13 |
| Blood | 0.80 | | 0.01 | | 0.03 |
| Stomach | 2.09 | | 0.04 | | 0.21 |
| Sm Intestine | 2.56 | | 0.03 | | 0.08 |
| Muscle | 1.73 | | 0.02 | | 0.02 |
| Femur | 2.49 | | 0.04 | | 0.07 |
| Tumor/blood | 10:1 | | 249:1 | | 3:1 |

F-18    Ga-68

IMP-479
Molecular Weight =1349.5446
Exact Mass =1348.7330
Molecular Formula =C62H96N18O16

HH22-168
NODA-HA-D-Ala-D-Lys(HSG)-D-Tyr-D-Lys(HSG)-NH₂

[M-H]⁻ 1347.7214

IMP-485
Molecular Weight =1312.4750
Exact Mass =1311.6724
Molecular Formula =C62H89N17O15
II14-137-11
NODA-MPAA-D-Lys(HSG)-D-Tyr-D-Lys(HSG)-NH₂

(M+H)⁺  1312.6838

IMP-487

Molecular Weight =1383.5229
Exact Mass =1382.7095
Molecular Formula =C65H94N18O16

II14-150-13

NODA-EPA-succinyl-D-Lys(HSG)-D-Tyr-D-Lys(HSG)-NH$_2$

SEQUENCE LISTING

```
<160> NUMBER OF SEQ ID NOS: 39

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term DOTA
<220> FEATURE:
<221> NAME/KEY: MOD_RES
<222> LOCATION: (2)..(2)
<223> OTHER INFORMATION: Lys(HSG)
<220> FEATURE:
<221> NAME/KEY: MOD_RES
<222> LOCATION: (4)..(4)
<223> OTHER INFORMATION: Lys(HSG)
<220> FEATURE:
<223> OTHER INFORMATION: C-term amidated
<220> FEATURE:
<223> OTHER INFORMATION: see specification as filed for detailed
      description of substitutions and preferred embodiments

<400> SEQUENCE: 1

Phe Lys Tyr Lys
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Lys(DTPA)
<220> FEATURE:
<221> NAME/KEY: MOD_RES
<222> LOCATION: (3)..(3)
<223> OTHER INFORMATION: Lys(DTPA)
<220> FEATURE:
<221> NAME/KEY: MOD_RES
<222> LOCATION: (4)..(4)
<223> OTHER INFORMATION: Lys(Tscg-Cys); branched sequence with C-term
      Lys which has a (Tscg-Cys) side-chain; Cys is not the C-term
      residue

<400> SEQUENCE: 2

Lys Tyr Lys Lys
```

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term DTPA
<220> FEATURE:
<221> NAME/KEY: MOD_RES
<222> LOCATION: (3)..(3)
<223> OTHER INFORMATION: Lys(HSG)
<220> FEATURE:
<221> NAME/KEY: MOD_RES
<222> LOCATION: (4)..(4)
<223> OTHER INFORMATION: D-Tyr
<220> FEATURE:
<221> NAME/KEY: MOD_RES
<222> LOCATION: (5)..(5)
<223> OTHER INFORMATION: Lys(HSG)
<220> FEATURE:
<223> OTHER INFORMATION: C-term amidated

<400> SEQUENCE: 3

Gln Ala Lys Tyr Lys
1               5

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NOTA-ITC benzyl
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 4

Ala Lys Tyr Lys
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES

```
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 5

Ala Lys Tyr Lys
1

<210> SEQ ID NO 6
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 7
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Ile Glu Tyr Leu Ala Lys Gln Ile Val Asp Asn Ala Ile Gln Gln
1               5                   10                  15

Ala

<210> SEQ ID NO 9
<211> LENGTH: 21
<212> TYPE: PRT
<213> ORGANISM: Artificial Sequence
<220> FEATURE:
```

<223> OTHER INFORMATION: Description of Artificial Sequence: Synthetic
       peptide

<400> SEQUENCE: 9

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 10
<211> LENGTH: 55
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 10

Gly Ser Gly Gly Gly Ser Gly Gly Gly Ser His Ile Gln Ile
1               5                   10                  15

Pro Pro Gly Leu Thr Glu Leu Leu Gln Gly Tyr Thr Val Glu Val Leu
                20                  25                  30

Arg Gln Gln Pro Pro Asp Leu Val Glu Phe Ala Val Glu Tyr Phe Thr
            35                  40                  45

Arg Leu Arg Glu Ala Arg Ala
        50                  55

<210> SEQ ID NO 11
<211> LENGTH: 29
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 11

Gly Ser Gly Gly Gly Gly Ser Gly Gly Gly Ser Gln Ile Glu Tyr
1               5                   10                  15

Leu Ala Lys Gln Ile Val Asp Asn Ala Ile Gln Gln Ala
            20                  25

<210> SEQ ID NO 12
<211> LENGTH: 51
<212> TYPE: PRT
<213> ORGANISM: Homo sapiens

<400> SEQUENCE: 12

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
                20                  25                  30

Arg Pro Met Ala Phe Leu Arg Glu Tyr Phe Glu Lys Leu Glu Lys Glu
            35                  40                  45

Glu Ala Lys
    50

<210> SEQ ID NO 13
<211> LENGTH: 54
<212> TYPE: PRT
<213> ORGANISM: Homo sapiens

<400> SEQUENCE: 13

Ser Leu Lys Gly Cys Glu Leu Tyr Val Gln Leu His Gly Ile Gln Gln

-continued

```
                1               5                  10                  15
Val Leu Lys Asp Cys Ile Val His Leu Cys Ile Ser Lys Pro Glu Arg
                    20                  25                  30

Pro Met Lys Phe Leu Arg Glu His Phe Glu Lys Leu Glu Lys Glu Glu
            35                  40                  45

Asn Arg Gln Ile Leu Ala
        50

<210> SEQ ID NO 14
<211> LENGTH: 44
<212> TYPE: PRT
<213> ORGANISM: Homo sapiens

<400> SEQUENCE: 14

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Gln
        35                  40

<210> SEQ ID NO 15
<211> LENGTH: 44
<212> TYPE: PRT
<213> ORGANISM: Homo sapiens

<400> SEQUENCE: 15

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
        35                  40

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Ile Glu Tyr Val Ala Lys Gln Ile Val Asp Tyr Ala Ile His Gln
1               5                   10                  15

Ala

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Ile Glu Tyr Lys Ala Lys Gln Ile Val Asp His Ala Ile His Gln
1               5                   10                  15

Ala

<210> SEQ ID NO 18
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ile Glu Tyr His Ala Lys Gln Ile Val Asp His Ala Ile His Gln
1               5                   10                  15

Ala

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ile Glu Tyr Val Ala Lys Gln Ile Val Asp His Ala Ile His Gln
1               5                   10                  15

Ala

<210> SEQ ID NO 20
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Glu Gln Tyr Ala Asn Gln Leu Ala Asp Gln Ile Ile Lys Glu Ala
1               5                   10                  15

Thr Glu

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Glu Glu Leu Ala Trp Lys Ile Ala Lys Met Ile Trp Ser Asp Val
1               5                   10                  15

Phe Gln Gln Cys
            20
```

```
<210> SEQ ID NO 23
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 24
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 25
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NODA-Ga
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 26
```

Ala Lys Tyr Lys
1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NOTA
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 27

Ala Lys Tyr Lys
1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NOTA
<220> FEATURE:
<221> NAME/KEY: MOD_RES
<222> LOCATION: (1)..(1)
<223> OTHER INFORMATION: D-Asp
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 28

Asp Lys Tyr Lys
1

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: N-term C-NETA-succinyl
<220> FEATURE:
<221> NAME/KEY: MOD_RES
<222> LOCATION: (1)..(1)
<223> OTHER INFORMATION: D-Lys(HSG)
<220> FEATURE:
<221> NAME/KEY: MOD_RES
<222> LOCATION: (2)..(2)
<223> OTHER INFORMATION: D-Tyr
<220> FEATURE:
<221> NAME/KEY: MOD_RES
<222> LOCATION: (3)..(3)
<223> OTHER INFORMATION: D-Lys(HSG)
<220> FEATURE:
<223> OTHER INFORMATION: C-term amidated

<400> SEQUENCE: 29

Lys Tyr Lys
1

<210> SEQ ID NO 30
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term L-NETA-succinyl
<220> FEATURE:
<221> NAME/KEY: MOD_RES
<222> LOCATION: (1)..(1)
<223> OTHER INFORMATION: D-Lys(HSG)
<220> FEATURE:
<221> NAME/KEY: MOD_RES
<222> LOCATION: (2)..(2)
<223> OTHER INFORMATION: D-Tyr
<220> FEATURE:
<221> NAME/KEY: MOD_RES
<222> LOCATION: (3)..(3)
<223> OTHER INFORMATION: D-Lys(HSG)
<220> FEATURE:
<223> OTHER INFORMATION: C-term amidated

<400> SEQUENCE: 30

Lys Tyr Lys
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NOTA
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated
```

```
<400> SEQUENCE: 31

Ala Lys Tyr Lys
1

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NOTA-NH-(CH2)7CO
<220> FEATURE:
<223> OTHER INFORMATION: C-term amidated

<400> SEQUENCE: 32

Gln Trp Val Trp Ala Val Gly His Leu Met
1               5                   10

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NOTA
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (8)..(8)
<223> OTHER INFORMATION: Threoninol

<400> SEQUENCE: 33

Phe Cys Phe Trp Lys Thr Cys Thr
1               5

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term DOTA
<220> FEATURE:
<221> NAME/KEY: MOD_RES
<222> LOCATION: (1)..(1)
<223> OTHER INFORMATION: D-Tyr
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Glu
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated
```

```
<400> SEQUENCE: 34

Tyr Lys Glu Lys
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NODA-HA
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 35

Ala Lys Tyr Lys
1

<210> SEQ ID NO 36
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NODA-MPAA
<220> FEATURE:
<221> NAME/KEY: MOD_RES
<222> LOCATION: (1)..(1)
<223> OTHER INFORMATION: D-Lys(HSG)
<220> FEATURE:
<221> NAME/KEY: MOD_RES
<222> LOCATION: (2)..(2)
<223> OTHER INFORMATION: D-Tyr
<220> FEATURE:
<221> NAME/KEY: MOD_RES
<222> LOCATION: (3)..(3)
<223> OTHER INFORMATION: D-Lys(HSG)
<220> FEATURE:
<223> OTHER INFORMATION: C-term amidated

<400> SEQUENCE: 36

Lys Tyr Lys
1

<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NODA-EPA-succinyl
```

```
<220> FEATURE:
<221> NAME/KEY: MOD_RES
<222> LOCATION: (1)..(1)
<223> OTHER INFORMATION: D-Lys(HSG)
<220> FEATURE:
<221> NAME/KEY: MOD_RES
<222> LOCATION: (2)..(2)
<223> OTHER INFORMATION: D-Tyr
<220> FEATURE:
<221> NAME/KEY: MOD_RES
<222> LOCATION: (3)..(3)
<223> OTHER INFORMATION: D-Lys(HSG)
<220> FEATURE:
<223> OTHER INFORMATION: C-term amidated

<400> SEQUENCE: 37

Lys Tyr Lys
1

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NOT2A-MPAA
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (8)..(8)
<223> OTHER INFORMATION: Threoninol

<400> SEQUENCE: 38

Phe Cys Phe Trp Lys Thr Cys Thr
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NOT2A-MPAA-(PEG)3
<220> FEATURE:
<223> OTHER INFORMATION: C-term amidated

<400> SEQUENCE: 39

Gln Trp Ala Val Gly His Leu Met
1               5
```

METHODS AND COMPOSITIONS FOR IMPROVED F-18 LABELING OF PROTEINS, PEPTIDES AND OTHER MOLECULES

RELATED APPLICATIONS

This application is a continuation-in-part of U.S. patent application Ser. No. 12/433,212, filed Apr. 30, 2009, which was a continuation-in-part of U.S. patent application Ser. No. 12/343,655, filed Dec. 24, 2008, now U.S. Pat. No. 7,993,626 which was a continuation-in-part of U.S. patent application Ser. No. 12/112,289 (now issued U.S. Pat. No. 7,563,433), filed Apr. 30, 2008, which was a continuation-in-part of U.S. patent application Ser. No. 11/960,262 (now issued U.S. Pat. No. 7,597,876), filed Dec. 19, 2007, which claimed the benefit under 35 U.S.C. 119(e) of provisional U.S. Patent Application 60/884,521 (now expired), filed Jan. 11, 2007. This application claims the benefit under 35 U.S.C. 119(e) of provisional U.S. Patent Application No. 61/266,773 (now expired), filed Dec. 4, 2009; provisional U.S. Patent Application No. 61/302,280 (now expired), filed Feb. 8, 2010; provisional U.S. Patent Application No. 61/316,125 (now expired), filed Mar. 22, 2010; provisional U.S. Patent Application No. 61/347,486 (now expired), filed May 24, 2010; provisional U.S. Patent Application No. 61/381,720, filed Sep. 10, 2010 and provisional U.S. Patent Application No. 61/388,268, filed Sep. 30, 2010. Each priority application is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Dec. 2, 2010, is named IMM31US7.txt and is 16,944 bytes in size.

FIELD

The present invention concerns methods of labeling peptides or other molecules with $^{18}F$ or $^{19}F$ that are of use, for example, in PET or NMR in vivo imaging. Preferably, the $^{18}F$ or $^{19}F$ is attached as a conjugate [complex] with aluminum or another metal via a chelating moiety, which may be covalently linked to a protein, peptide or other molecule. Using the techniques described herein, $^{18}F$- or $^{19}F$-labeled molecules of high specific activity may be prepared in 30 minutes or less and are suitable for use in imaging techniques without the need for HPLC purification of the labeled molecule. Labeling may occur in a saline medium suitable for direct use in vivo. In alternative embodiments an organic solvent may be added to improve the efficiency of labeling. The labeled molecules are stable under in vivo conditions, although for certain purposes, such as kit formulations, a stabilizing agent such as ascorbic acid, trehalose, sorbitol or mannitol may be added. In other alternative embodiments, a chelating moiety may be preloaded with aluminum and lyophilized for storage, prior to labeling with $^{18}F$ or $^{19}F$.

BACKGROUND

Positron Emission Tomography (PET) has become one of the most prominent functional imaging modalities in diagnostic medicine, with very high sensitivity (fmol), high resolution (4-10 mm) and tissue accretion that can be adequately quantitated (Volkow et al., 1988, Am. J. Physiol. Imaging 3:142). Although [$^{18}F$]2-deoxy-2-fluoro-D-glucose ([$^{18}F$] FDG) is the most widely used functional imaging agent in oncology (Fletcher et al., 2008, J. Nucl. Med. 49:480), there is a keen interest in developing other labeled compounds for functional imaging to complement and augment anatomic imaging methods (Torigian et al., 2007, CA Cancer J. Clin. 57:206), especially with the hybrid PET/computed tomography systems currently in use. Thus, there is a need to have facile methods of conjugating positron-emitting radionuclides to various molecules of biological and medical interest.

Peptides or other small molecules can be labeled with the positron emitters $^{18}F$, $^{64}Cu$, $^{11}C$, $^{66}Ga$, $^{68}Ga$, $^{76}Br$, $^{94m}Tc$, $^{86}Y$, and $^{124}I$. A low ejection energy for a PET isotope is desirable to minimize the distance that the positron travels from the target site before it generates the two 511 keV gamma rays that are imaged by the PET camera. Many isotopes that emit positrons also have other emissions such as gamma rays, alpha particles or beta particles in their decay chain. It is desirable to have a PET isotope that is a pure positron emitter so that any dosimetry problems will be minimized. The half-life of the isotope is also important, since the half-life must be long enough to attach the isotope to a targeting molecule, analyze the product, inject it into the patient, and allow the product to localize, clear from non-target tissues and then image. If the half-life is too long the specific activity may not be high enough to obtain enough photons for a clear image and if it is too short the time needed for manufacturing, commercial distribution and biodistribution may not be sufficient. $^{18}F$ ($\beta^+$ 635 keV 97%, $t_{1/2}$ 110 min) is one of the most widely used PET emitting isotopes because of its low positron emission energy, lack of side emissions and suitable half-life.

Conventionally, $^{18}F$ is attached to compounds by binding it to a carbon atom (Miller et al., 2008, Angew Chem Int Ed 47:8998-9033), but attachments to silicon (Shirrmacher et al., 2007, Bioconj Chem 18:2085-89; Hohne et al., 2008, Bioconj Chem 19:1871-79) and boron (Ting et al., 2008, Fluorine Chem 129:349-58) have also been reported. Binding to carbon usually involves multistep syntheses, including multiple purification steps, which is problematic for an isotope with a 110-min half-life. Current methods for $^{18}F$ labeling of peptides typically involve the labeling of a reagent at low specific activity, HPLC purification of the reagent and then conjugation to the peptide of interest. The conjugate is often repurified after conjugation to obtain the desired specific activity of labeled peptide.

An example is the labeling method of Poethko et al. (J. Nucl. Med. 2004; 45: 892-902) in which 4-[$^{18}F$]fluorobenzaldehyde is first synthesized and purified (Wilson et al, J. Labeled Compounds and Radiopharm. 1990; XXVIII: 1189-1199) and then conjugated to the peptide. The peptide conjugate is then purified by HPLC to remove excess peptide that was used to drive the conjugation to completion. Other examples include labeling with succinyl [$^{18}F$]fluorobenzoate (SFB) (e.g., Vaidyanathan et al., 1992, Int. J. Rad. Appl. Instrum. B 19:275), other acyl compounds (Tada et al., 1989, Labeled Compd. Radiopharm.XXVII:1317; Wester et al., 1996, Nucl. Med. Biol. 23:365; Guhlke et al., 1994, Nucl. Med. Biol 21:819), or click chemistry adducts (Li et al., 2007, Bioconjugate Chem. 18:1987). The total synthesis and formulation time for these methods ranges between 1-3 hours, with most of the time dedicated to the HPLC purification of the labeled peptides to obtain the specific activity required for in vivo targeting. With a 2 hr half-life, all of the manipulations that are needed to attach the $^{18}F$ to the peptide are a significant burden. These methods are also tedious to perform and require the use of equipment designed specifically to produce the labeled product and/or the efforts of specialized professional chemists. They are also not conducive to kit formulations that could routinely be used in a clinical setting.

A need exists for a rapid, simple method of $^{18}$F labeling of targeting moieties, such as proteins or peptides, which results in targeting constructs of suitable specific activity and in vivo stability for detection and/or imaging, while minimizing the requirements for specialized equipment or highly trained personnel and reducing operator exposure to high levels of radiation. More preferably a need exists for methods of preparing $^{18}$F-labeled targeting peptides of use in pretargeting technologies. A further need exists for prepackaged kits that could provide compositions required for performing such novel methods.

SUMMARY

In various embodiments, the present invention concerns compositions and methods relating to $^{18}$F- or $^{19}$F-labeled molecules of use for PET or NMR imaging. As discussed herein, where the present application refers to $^{18}$F the skilled artisan will realize that either $^{18}$F, $^{19}$F or another metal-binding radionuclide, such as $^{68}$Ga, may be utilized. In an exemplary approach, the $^{18}$F is bound to a metal and the $^{18}$F-metal complex is attached to a ligand on a peptide or other molecule. As described below, the metals of group IIIA (aluminum, gallium, indium, and thallium) are suitable for $^{18}$F binding, although aluminum is preferred. Lutetium may also be of use. The metal binding ligand is preferably a chelating agent, such as NOTA, NETA, DOTA, DTPA and other chelating groups discussed in more detail below. Alternatively, one can attach the metal to a molecule first and then add the $^{18}$F to bind to the metal.

The skilled artisan will realize that virtually any delivery molecule can be attached to $^{18}$F for imaging purposes, so long as it contains derivatizable groups that may be modified without affecting the ligand-receptor binding interaction between the delivery molecule and the cellular or tissue target receptor. Although the Examples below primarily concern $^{18}$F-labeled peptide moieties, many other types of delivery molecules, such as oligonucleotides, hormones, growth factors, cytokines, chemokines, angiogenic factors, anti-angiogenic factors, immunomodulators, proteins, nucleic acids, antibodies, antibody fragments, drugs, interleukins, interferons, oligosaccharides, polysaccharides, lipids, etc. may be $^{18}$F-labeled and utilized for imaging purposes.

Exemplary targetable construct peptides described in the Examples below, of use for pre-targeting delivery of $^{18}$F or other agents, include but are not limited to IMP 449, IMP 460, IMP 461, IMP 467, IMP 469, IMP 470, IMP 471, IMP 479, IMP 485 and IMP 487, comprising chelating moieties that include, but are not limited to, DTPA, NOTA, benzyl-NOTA, alkyl or aryl derivatives of NOTA, NODA-GA, C-NETA, succinyl-C-NETA and bis-t-butyl-NODA.

In certain embodiments, the exemplary $^{18}$F-labeled peptides may be of use as targetable constructs in a pre-targeting method, utilizing bispecific or multispecific antibodies or antibody fragments. In this case, the antibody or fragment will comprise one or more binding sites for a target associated with a disease or condition, such as a tumor-associated or autoimmune disease-associated antigen or an antigen produced or displayed by a pathogenic organism, such as a virus, bacterium, fungus or other microorganism. A second binding site will specifically bind to the targetable construct. Methods for pre-targeting using bispecific or multispecific antibodies are well known in the art (see, e.g., U.S. Pat. No. 6,962,702, the Examples section of which is incorporated herein by reference.) Similarly, antibodies or fragments thereof that bind to targetable constructs are also well known in the art, such as the 679 monoclonal antibody that binds to HSG (histamine succinyl glycine) or the 734 antibody that binds to In-DTPA (see U.S. Pat. Nos. 7,429,381; 7,563,439; 7,666,415; and 7,534,431, the Examples section of each incorporated herein by reference). Generally, in pretargeting methods the bispecific or multispecific antibody is administered first and allowed to bind to cell or tissue target antigens. After an appropriate amount of time for unbound antibody to clear from circulation, the e.g. $^{18}$F-labeled targetable construct is administered to the patient and binds to the antibody localized to target cells or tissues, then an image is taken for example by PET scanning.

In alternative embodiments, molecules that bind directly to receptors, such as somatostatin, octreotide, bombesin, folate or a folate analog, an RGD peptide or other known receptor ligands may be labeled and used for imaging. Receptor targeting agents may include, for example, TA138, a non-peptide antagonist for the integrin $\alpha_v\beta_3$ receptor (Liu et al., 2003, Bioconj. Chem. 14:1052-56). Other methods of receptor targeting imaging using metal chelates are known in the art and may be utilized in the practice of the claimed methods (see, e.g., Andre et al., 2002, J. Inorg. Biochem. 88:1-6; Pearson et al., 1996, J. Med., Chem. 39:1361-71).

The type of diseases or conditions that may be imaged is limited only by the availability of a suitable delivery molecule for targeting a cell or tissue associated with the disease or condition. Many such delivery molecules are known. For example, any protein or peptide that binds to a diseased tissue or target, such as cancer, may be labeled with $^{18}$F by the disclosed methods and used for detection and/or imaging. In certain embodiments, such proteins or peptides may include, but are not limited to, antibodies or antibody fragments that bind to tumor-associated antigens (TAAs). Any known TAA-binding antibody or fragment may be labeled with $^{18}$F by the described methods and used for imaging and/or detection of tumors, for example by PET scanning or other known techniques.

Certain alternative embodiments involve the use of click chemistry reactions for attachment of metal-$^{18}$F-chelating moieties to molecules. Preferably, the click chemistry involves the reaction of a targeting molecule such as an antibody or antigen-binding antibody fragment, comprising an activating moiety such as an alkyne, a nitrone or an azide group, with a chelating moiety or a carrier molecule attached to one or more chelating groups and comprising a corresponding reactive moiety, such as an azide, alkyne or nitrone. Where the targeting molecule comprises an alkyne, the chelating moiety or carrier will comprise an azide, a nitrone or similar reactive moiety. The click chemistry reaction may occur in vitro to form a highly stable, labeled targeting molecule that is then administered to a subject.

BRIEF DESCRIPTION OF THE DRAWINGS

The following Figures are included to illustrate particular embodiments of the invention and are not meant to be limiting as to the scope of the claimed subject matter.

FIG. 1. Biodistribution of $^{18}$F-labeled agents in tumor-bearing nude mice by microPET imaging. Coronal slices of 3 nude mice bearing a small, subcutaneous LS174T tumor on each left flank after being injected with either (A) [$^{18}$F]FDG, (B) Al[$^{18}$F] IMP 449 pretargeted with the anti-CEA×anti-HSG bsMAb, (C) Al[$^{18}$F] IMP 449 alone (not pretargeted with the bsMAb). Biodistribution data expressed as percent-injected dose per gram (% ID/g) are given for the tissues removed from the animals at the conclusion of the imaging session. Abbreviations: B, bone marrow; H, heart; K, kidney; T, tumor.

DETAILED DESCRIPTION

Figure 2:
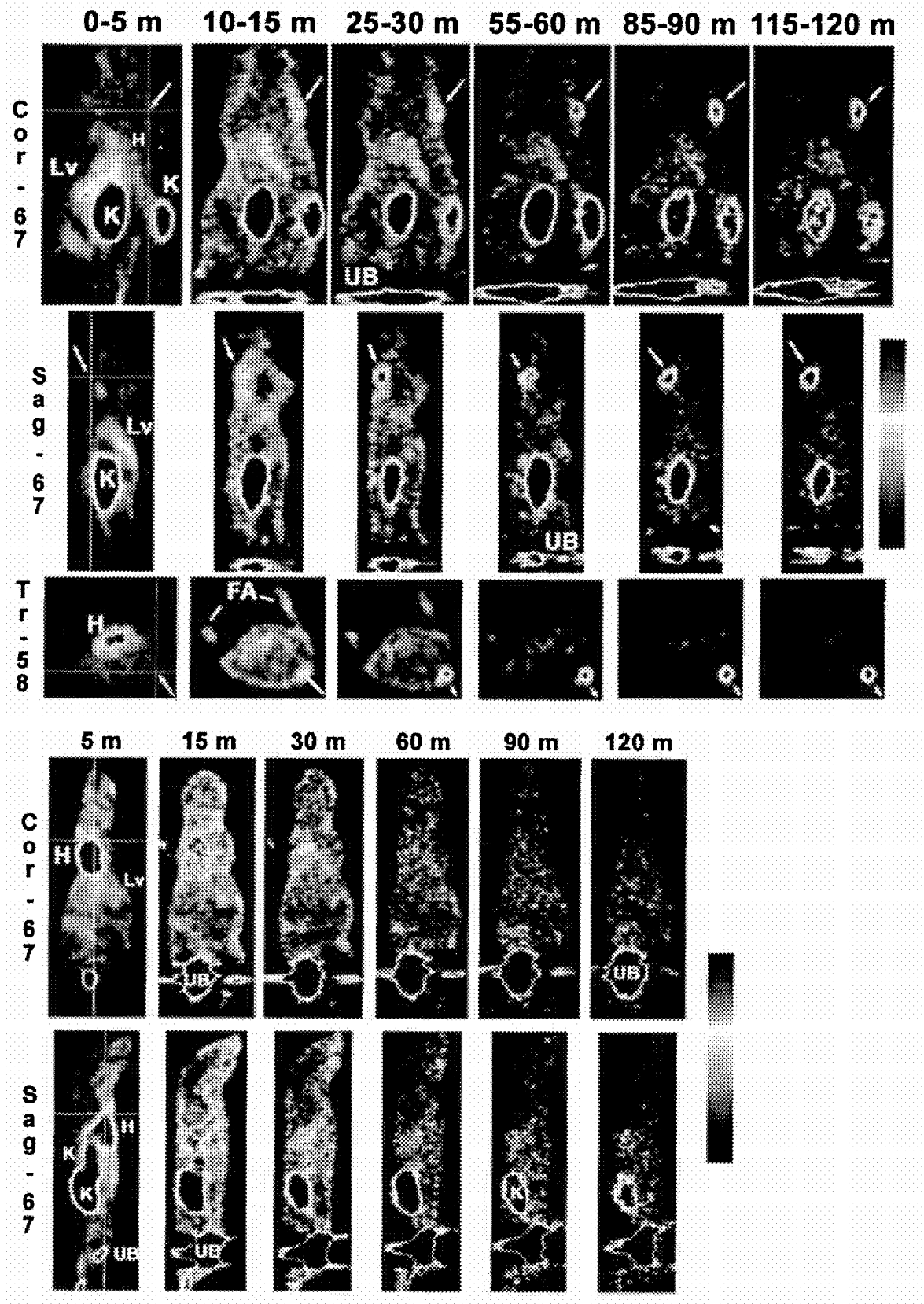
FIG. 2. Dynamic imaging study of pretargeted Al[$^{18}$F] IMP 449 given to a nude mouse bearing a 35-mg LS174T human colorectal cancer xenograft in the upper flank. The top 3 panels show coronal, sagittal, and transverse sections, respectively, taken of a region of the body centering on the tumor's peripheral location at 6 different 5-min intervals over the 120-min imaging session. The first image on the left in each sectional view shows the positioning of the tumor at the intersection of the crosshairs, which is highlighted by arrows. The animal was partially tilted to its right side during the imaging session. The bottom 2 panels show additional coronal and sagittal sections that focus on a more anterior plane in the coronal section to highlight distribution in the liver and intestines, while the sagittal view crosses more centrally in the body. Abbreviations: Cor, coronal; FA, forearms; H, heart; K, kidney; Lv, liver; Sag, sagittal; Tr, transverse; UB, urinary bladder.

The following definitions are provided to facilitate understanding of the disclosure herein. Terms that are not explicitly defined are used according to their plain and ordinary meaning.

As used herein, "a" or "an" may mean one or more than one of an item.

As used herein, the terms "and" and "or" may be used to mean either the conjunctive or disjunctive. That is, both terms should be understood as equivalent to "and/or" unless otherwise stated.

As used herein, "about" means within plus or minus ten percent of a number. For example, "about 100" would refer to any number between 90 and 110.

As used herein, a "peptide" refers to any sequence of naturally occurring or non-naturally occurring amino acids of between 2 and 100 amino acid residues in length, more preferably between 2 and 10, more preferably between 2 and 6 amino acids in length. An "amino acid" may be an L-amino acid, a D-amino acid, an amino acid analogue, an amino acid derivative or an amino acid mimetic.

As used herein, the term "pathogen" includes, but is not limited to fungi, viruses, parasites and bacteria, including but not limited to human immunodeficiency virus (HIV), herpes virus, cytomegalovirus, rabies virus, influenza virus, hepatitis B virus, Sendai virus, feline leukemia virus, Reovirus, polio virus, human serum parvo-like virus, simian virus 40, respiratory syncytial virus, mouse mammary tumor virus, Varicella-Zoster virus, Dengue virus, rubella virus, measles virus, adenovirus, humane T-cell leukemia viruses, Epstein-Barr virus, murine leukemia virus, mumps virus, vesicular stomatitis virus, Sindbis virus, lymphocytic choriomeningitis virus, wart virus, blue tongue virus, *Streptococcus agalactiae, Legionella pneumophila, Streptococcus pyogenes, Escherichia coli, Neisseria gonorrhoeae, Neisseria meningitidis, Pneumococcus, Hemophilus influenzae* B, *Treponema pallidum, Lyme disease spirochetes, Pseudomonas aeruginosa, Mycobacterium leprae, Brucella abortus, Mycobacterium tuberculosis* and *Clostridium tetani*.

As used herein, a "radiolysis protection agent" refers to any molecule, compound or composition that may be added to an $^{18}$F-labeled complex or molecule to decrease the rate of breakdown of the $^{18}$F-labeled complex or molecule by radiolysis. Any known radiolysis protection agent, including but not limited to ascorbic acid, may be used.

$^{18}$F Labeling Techniques

A variety of techniques for labeling molecules with $^{18}$F are known. Table 1 lists the properties of several of the more commonly reported fluorination procedures. Peptide labeling through carbon often involves $^{18}$F-binding to a prosthetic group through nucleophilic substitution, usually in 2- or 3-steps where the prosthetic group is labeled and purified, attached to the compound, and then purified again. This general method has been used to attach prosthetic groups through amide bonds, aldehydes, and "click chemistry" (Marik et al., 2006, Bioconjug Chem 17:1017-21; Poethko et al., 2004, J Nucl Med 45:892-902; Li et al., 2007, Bioconjug Chem 18:989-93). The most common amide bond-forming reagent has been N-succinimidyl 4-$^{18}$F-fluorobenzoate ($^{18}$F-SFB), but a number of other groups have been tested (Marik et al., 2006). In some cases, such as when $^{18}$F-labeled active ester amide-forming groups are used, it may be necessary to protect certain groups on a peptide during the coupling reaction, after which they are cleaved. The synthesis of this $^{18}$F—SFB reagent and subsequent conjugation to the peptide requires many synthetic steps and takes about 2-3 h.

A simpler, more efficient $^{18}$F-peptide labeling method was developed by Poethko et al. (2004), where a 4-$^{18}$F-fluorobenzaldehyde reagent was conjugated to a peptide through an oxime linkage in about 75-90 min, including the dry-down step. The newer "click chemistry" method attaches $^{18}$F-labeled molecules onto peptides with an acetylene or azide in the presence of a copper catalyst (Li et al, 2007; Glaser and Arstad, 2007, Bioconjug Chem 18:989-93). The reaction between the azide and acetylene groups forms a triazole connection, which is quite stable and forms very efficiently on peptides without the need for protecting groups. Click chemistry produces the $^{18}$F-labeled peptides in good yield (~50%) in about 75-90 min with the dry-down step.

1982, Science 215:1511-13). For PET imaging, $^{64}$Cu and $^{68}$Ga have been bound to peptides via a chelate, and have shown reasonably good PET-imaging properties (Heppler et al., 2000, Current Med Chem 7:971-94). Since fluoride binds to most metals, we sought to determine if an $^{18}$F-metal complex could be bound to a chelator on a targeting molecule (Tewson, 1989, Nucl Med Biol. 16:533-51; Martin, 1996, Coordination Chem Rev 141:23-32). We have focused on the binding of an Al$^{18}$F complex, since aluminum-fluoride can be relatively stable in vivo (Li, 2003, Crit. Rev Oral Biol Med 14:100-114; Antonny et al., 1992, J Biol Chem 267:6710-18). Initial studies showed the feasibility of this approach to prepare an $^{18}$F-labeled peptide for in vivo targeting of cancer with a bispecific antibody (bsMAb) pretargeting system, a highly sensitive and specific technique for localizing cancer,

TABLE 1

Summary of selected $^{18}$F-peptide labeling methods.

| | Schirrmacher et al. (2007) | Höhne et al. (2008) | Li et al. (2007) | Glaser & Arstad (2007) | Poethko et al. (2004) | Marik et al (2006) |
|---|---|---|---|---|---|---|
| Attachment | Silicon | Silicon | Click | Click | Aldehyde/oxime | Amide |
| Rx steps | 2 | 1 | 2 | 2 | 2 | many |
| Rx time (min)$^a$ | 40 | 115-155 | 110 | 65-80 (estimated) | 75-90 min (estimated) | 110+ |
| Yield$^b$ | 55% | 13% | 54% | 50% | 40% | 10% |
| HPLC-purification steps | 1 | 1 | 2 | 1 + distillation | 1 | 2 |
| Specific Activity (GBq/µmol) | 225-680 | 62 | high | high | high | high |

$^a$Including dry-down time
$^b$Decay corrected

A more recent method of binding $^{18}$F to silicon uses isotopic exchange to displace $^{19}$F with $^{18}$F (Shirrmacher et al., 2007). Performed at room temperature in 10 min, this reaction produces the $^{18}$F-prosthetic aldehyde group with high specific activity (225-680 GBq/µmol; 6,100-18,400 Ci/mmol). The $^{18}$F-labeled aldehyde is subsequently conjugated to a peptide and purified by HPLC, and the purified labeled peptide is obtained within 40 min (including dry-down) with ~55% yield. This was modified subsequently to a single-step process by incorporating the silicon into the peptide before the labeling reaction (Hohne et al, 2008). However, biodistribution studies in mice with an $^{18}$F-silicon-bombesin derivative showed bone uptake increasing over time (1.35±0.47% injected dose (ID)/g at 0.5 h vs. 5.14±2.71% ID/g at 4.0 h), suggesting a release of $^{18}$F from the peptide, since unbound $^{18}$F is known to localize in bone (Hohn et al., 2008). HPLC analysis of urine showed a substantial amount of $^{18}$F activity in the void volume, which presumably is due to $^{18}$F$^-$ fluoride anion released from the peptide. It would therefore appear that the $^{18}$F-silicon labeled molecule was not stable in serum. Substantial hepatobiliary excretion was also reported, attributed to the lipophilic nature of the $^{18}$F-silicon-binding substrate, and requiring future derivatives to be more hydrophilic. Methods of attaching $^{18}$F to boron also have been explored; however, the current process produces conjugates with low specific activity (Ting et al., 2008).

Antibodies and peptides are coupled routinely with radiometals, typically in 15 min and in quantitative yields (Meares et al., 1984, Acc Chem Res 17:202-209; Scheinberg et al., in some cases better than $^{18}$F-FDG (fluorodeoxyglucose) (McBride et al., 2008, J Nucl Med (suppl) 49:97 P; Wagner, 2008, J Nucl Med 49:23 N-24N; Karacay et al., 2000, Bioconj Chem 11:842-54; Sharkey et al., 2008, Cancer Res 68; 5282-90; Gold Et al., 2008, Cancer Res 68:4819-26; Sharkey et al., 2005, Nature Med 11:1250-55; Sharkey et al., 2005, Clin Cancer Res 11:7109s-7121s; McBride et al., 2006, J Nucl Med 47:1678-88; Sharkey et al., 2008, Radiology 246:497-508). These studies revealed that an Al$^{18}$F complex could bind stably to a 1,4,7-triazacyclononane-1,4,7-triacetic acid (NOTA), but the yields were low.

In the Examples below, new labeling conditions and several new chelating moieties were examined that enhanced yields from about 10% to about 80%, providing a feasible method for $^{18}$F labeling of peptides and other molecules of use for PET imaging.

Targetable Constructs

In certain embodiments, the moiety labeled with $^{18}$F or other diagnostic and/or therapeutic agents may comprise a peptide or other targetable construct. Labeled peptides (or proteins) may be selected to bind directly to a targeted cell, tissue, pathogenic organism or other target for imaging, detection and/or diagnosis. In other embodiments, labeled peptides may be selected to bind indirectly, for example using a bispecific antibody with one or more binding sites for a targetable construct peptide and one or more binding sites for a target antigen associated with a disease or condition. Bispecific antibodies may be used, for example, in a pretargeting technique wherein the antibody may be administered first to a subject. Sufficient time may be allowed for the bispecific antibody to bind to a target antigen and for unbound antibody to clear from circulation. Then a targetable construct, such as a labeled peptide, may be administered to the subject and allowed to bind to the bispecific antibody and localize at the diseased cell or tissue. The distribution of $^{18}$F-labeled targetable constructs may be determined by PET scanning or other known techniques.

Such targetable constructs can be of diverse structure and are selected not only for the availability of an antibody or fragment that binds with high affinity to the targetable construct, but also for rapid in vivo clearance when used within the pre-targeting method and bispecific antibodies (bsAb) or multispecific antibodies. Hydrophobic agents are best at eliciting strong immune responses, whereas hydrophilic agents are preferred for rapid in vivo clearance. Thus, a balance between hydrophobic and hydrophilic character is established. This may be accomplished, in part, by using hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic. Aside from peptides, carbohydrates may also be used.

Peptides having as few as two amino acid residues, preferably two to ten residues, may be used and may also be coupled to other moieties, such as chelating agents. The linker should be a low molecular weight conjugate, preferably having a molecular weight of less than 50,000 daltons, and advantageously less than about 20,000 daltons, 10,000 daltons or 5,000 daltons. More usually, the targetable construct peptide will have four or more residues, such as the peptide DOTA-Phe-Lys(HSG)-Tyr-Lys(HSG)-NH$_2$ (SEQ ID NO: 1), wherein DOTA is 1,4,7,10-tetraazacyclododecane-1,4,7,10-tetraacetic acid and HSG is the histamine succinyl glycyl group. Alternatively, DOTA may be replaced by NOTA (1,4, 7-triaza-cyclononane-1,4,7-triacetic acid), TETA (p-bromoacetamido-benzyl-tetraethylaminetetraacetic acid), NETA ([2-(4,7-biscarboxymethyl[1,4,7]triazacyclononan-1-yl-ethyl]-2-carbonylmethyl-amino]acetic acid) or other known chelating moieties.

The targetable construct may also comprise unnatural amino acids, e.g., D-amino acids, in the backbone structure to increase the stability of the peptide in vivo. In alternative embodiments, other backbone structures such as those constructed from non-natural amino acids or peptoids may be used.

The peptides used as targetable constructs are conveniently synthesized on an automated peptide synthesizer using a solid-phase support and standard techniques of repetitive orthogonal deprotection and coupling. Free amino groups in the peptide, that are to be used later for conjugation of chelating moieties or other agents, are advantageously blocked with standard protecting groups such as a Boc group, while N-terminal residues may be acetylated to increase serum stability. Such protecting groups are well known to the skilled artisan. See Greene and Wuts Protective Groups in Organic Synthesis, 1999 (John Wiley and Sons, N.Y.). When the peptides are prepared for later use within the bispecific antibody system, they are advantageously cleaved from the resins to generate the corresponding C-terminal amides, in order to inhibit in vivo carboxypeptidase activity. Exemplary methods of peptide synthesis are disclosed in the Examples below.

Where pretargeting with bispecific antibodies is used, the antibody will contain a first binding site for an antigen produced by or associated with a target tissue and a second binding site for a hapten on the targetable construct. Exemplary haptens include, but are not limited to, HSG and In-DTPA. Antibodies raised to the HSG hapten are known (e.g. 679 antibody) and can be easily incorporated into the appropriate bispecific antibody (see, e.g., U.S. Pat. Nos. 6,962,702; 7,138,103 and 7,300,644, incorporated herein by reference with respect to the Examples sections). However, other haptens and antibodies that bind to them are known in the art and may be used, such as In-DTPA and the 734 antibody (e.g., U.S. Pat. No. 7,534,431, the Examples section incorporated herein by reference).

The skilled artisan will realize that although the majority of targetable constructs disclosed in the Examples below are peptides, other types of molecules may be used as targetable constructs. For example, polymeric molecules, such as polyethylene glycol (PEG) may be easily derivatized with chelating moieties to bind $^{18}$F—Al. Many examples of such carrier molecules are known in the art and may be utilized, including but not limited to polymers, nanoparticles, microspheres, liposomes and micelles. For use in pretargeted delivery of $^{18}$F, the only requirement is that the carrier molecule comprise one or more chelating moieties for attachment of metal-$^{18}$F and one or more hapten moieties to bind to a bispecific or multispecific antibody or other targeting molecule.

Chelating Moieties

In some embodiments, an $^{18}$F-labeled molecule may comprise one or more hydrophilic chelate moieties, which can bind metal ions and also help to ensure rapid in vivo clearance. Chelators may be selected for their particular metal-binding properties, and may be readily interchanged.

Particularly useful metal-chelate combinations include 2-benzyl-DTPA and its monomethyl and cyclohexyl analogs. Macrocyclic chelators such as NOTA (1,4,7-triaza-cyclononane-1,4,7-triacetic acid), DOTA, TETA (p-bromoacetamido-benzyl-tetraethylaminetetraacetic acid) and NETA are also of use with a variety of metals, that may potentially be used as ligands for $^{18}$F conjugation.

DTPA and DOTA-type chelators, where the ligand includes hard base chelating functions such as carboxylate or amine groups, are most effective for chelating hard acid cations, especially Group IIa and Group IIIa metal cations. Such metal-chelate complexes can be made very stable by tailoring the ring size to the metal of interest. Other ring-type chelators such as macrocyclic polyethers are of interest for stably binding nuclides. Porphyrin chelators may be used with numerous metal complexes. More than one type of chelator may be conjugated to a carrier to bind multiple metal ions. Chelators such as those disclosed in U.S. Pat. No. 5,753,206, especially thiosemicarbazonylglyoxylcysteine (Tscg-Cys) and thiosemicarbazinyl-acetylcysteine (Tsca-Cys) chelators are advantageously used to bind soft acid cations of Tc, Re, Bi and other transition metals, lanthanides and actinides that are tightly bound to soft base ligands. It can be useful to link more than one type of chelator to a peptide. Because antibodies to a di-DTPA hapten are known (Barbet et al., U.S. Pat. No. 5,256,395) and are readily coupled to a targeting antibody to form a bispecific antibody, it is possible to use a peptide hapten with cold di-DTPA chelator and another chelator for binding an $^{18}$F complex, in a pretargeting protocol. One example of such a peptide is Ac-Lys(DTPA)-Tyr-Lys (DTPA)-Lys(Tscg-Cys)-NH$_2$ (core peptide disclosed as SEQ ID NO:2). Other hard acid chelators such as DOTA, TETA and the like can be substituted for the DTPA and/or Tscg-Cys groups, and MAbs specific to them can be produced using analogous techniques to those used to generate the anti-di-DTPA MAb.

Another useful chelator may comprise a NOTA-type moiety, for example as disclosed in Chong et al. (*J. Med. Chem.*, 2008, 51:118-25). Chong et al. disclose the production and use of a bifunctional C-NETA ligand, based upon the NOTA structure, that when complexed with $^{177}$Lu or $^{205/206}$Bi showed stability in serum for up to 14 days. The chelators are not limiting and these and other examples of chelators that are known in the art and/or described in the following Examples may be used in the practice of the invention.

It will be appreciated that two different hard acid or soft acid chelators can be incorporated into the targetable construct, e.g., with different chelate ring sizes, to bind preferentially to two different hard acid or soft acid cations, due to the differing sizes of the cations, the geometries of the chelate rings and the preferred complex ion structures of the cations. This will permit two different metals, one or both of which may be attached to $^{18}$F, to be incorporated into a targetable construct for eventual capture by a pretargeted bispecific antibody.

Antibodies

Target Antigens

Targeting antibodies of use may be specific to or selective for a variety of cell surface or disease-associated antigens. Exemplary target antigens of use for imaging or treating various diseases or conditions, such as a malignant disease, a cardiovascular disease, an infectious disease, an inflammatory disease, an autoimmune disease, a metabolic disease, or a neurological (e.g., neurodegenerative) disease may include carbonic anhydrase IX, CCCL19, CCCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CXCR4, CXCR7, CXCL12, HIF-1α, AFP, CEACAM5, CEACAM6, c-met, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, NCA-95, NCA-90, pancreatic cancer mucin, placental growth factor, p53, PLAGL2, prostatic acid phosphatase, PSA, PRAME, PSMA, P1GF, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, complement factors C3, C3a, C3b, C5a, C5, PLAGL2, and an oncogene product.

In certain embodiments, such as imaging or treating tumors, antibodies of use may target tumor-associated antigens. These antigenic markers may be substances produced by a tumor or may be substances which accumulate at a tumor site, on tumor cell surfaces or within tumor cells. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744, the Examples section of each of which is incorporated herein by reference. Reports on tumor associated antigens (TAAs) include Mizukami et al., (2005, *Nature Med.* 11:992-97); Hatfield et al., (2005, *Curr. Cancer Drug Targets* 5:229-48); Vallbohmer et al. (2005, *J. Clin. Oncol.* 23:3536-44); and Ren et al. (2005, *Ann. Surg.* 242:55-63), each incorporated herein by reference with respect to the TAAs identified.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcinoembryonic antigen (CEA), which stimulate the production of antibodies having a greatly reduced cross-reactivity to non-tumor substances as disclosed in U.S. Pat. Nos. 4,361, 644 and 4,444,744.

Another marker of interest is transmembrane activator and CAML-interactor (TACI). See Yu et al. Nat. Immunol. 1:252-256 (2000). Briefly, TACI is a marker for B-cell malignancies (e.g., lymphoma). TACI and B-cell maturation antigen (BCMA) are bound by the tumor necrosis factor homolog—a proliferation-inducing ligand (APRIL). APRIL stimulates in vitro proliferation of primary B and T-cells and increases spleen weight due to accumulation of B-cells in vivo. APRIL also competes with TALL-I (also called BLyS or BAFF) for receptor binding. Soluble BCMA and TACI specifically prevent binding of APRIL and block APRIL-stimulated proliferation of primary B-cells. BCMA-Fc also inhibits production of antibodies against keyhole limpet hemocyanin and Pneumovax in mice, indicating that APRIL and/or TALL-I signaling via BCMA and/or TACI are required for generation of humoral immunity. Thus, APRIL-TALL-I and BCMA-TACI form a two ligand-two receptor pathway involved in stimulation of B and T-cell function.

Where the disease involves a lymphoma, leukemia or autoimmune disorder, targeted antigens may be selected from the group consisting of CD4, CD5, CD8, CD14, CD15, CD19, CD20, CD21, CD22, CD23, CD25, CD33, CD37, CD38, CD40, CD40L, CD46, CD52, CD54, CD67, CD74, CD79a, CD80, CD126, CD138, CD154, B7, MUC1, Ia, Ii, HM1.24, HLA-DR, tenascin, VEGF, P1GF, ED-B fibronectin, an oncogene (e.g., c-met or PLAGL2), an oncogene product, CD66a-d, necrosis antigens, IL-2, T101, TAG, IL-6, MIF, TRAIL-R1 (DR4) and TRAIL-R2 (DR5).

Methods for Raising Antibodies

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS 1N MOLECULAR BIOLOGY, VOL. 10, pages 79-104 (The Humana Press, Inc. 1992). After the initial raising of antibodies to the immunogen, the antibodies can be sequenced and subsequently prepared by recombinant techniques. Humanization and chimerization of murine antibodies and antibody fragments are well known to those skilled in the art, as discussed below.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., *Proc. Nat'l Acad. Sci. USA* 6: 3833 (1989). Techniques for constructing chimeric antibodies are well known to those of skill in the art. As an example, Leung et al., *Hybridoma* 13:469 (1994), produced an LL2 chimera by combining DNA sequences encoding the $V_\kappa$ and $V_H$ domains of murine LL2, an anti-CD22 monoclonal antibody, with respective human κ and IgG₁ constant region domains.

Humanized Antibodies

Techniques for producing humanized MAbs are well known in the art (see, e.g., Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Preferred residues for substitution include FR residues that are located within 1, 2, or 3 Angstroms of a CDR residue side chain, that are located adjacent to a CDR sequence, or that are predicted to interact with a CDR residue.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Pharmacol.* 3:544-50). A fully human antibody also can be constructed by genetic or chromosomal transfection methods, as well as phage display technology, all of which are known in the art. See for example, McCafferty et al., *Nature* 348:552-553 (1990). Such fully human antibodies are expected to exhibit even fewer side effects than chimeric or humanized antibodies and to function in vivo as essentially endogenous human antibodies.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), 1ˢᵗ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art. Phage display can be performed in a variety of formats, for their review, see e.g. Johnson and Chiswell, *Current Opinion in Structural Biology* 3:5564-571 (1993).

Human antibodies may also be generated by in vitro activated B-cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along with accessory genes and regulatory sequences. The human variable region repertoire may be used to generate antibody producing B-cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Known Antibodies

The skilled artisan will realize that the targeting molecules of use for imaging, detection and/or diagnosis may incorporate any antibody or fragment known in the art that has binding specificity for a target antigen associated with a disease state or condition. Such known antibodies include, but are not limited to, hR1 (anti-IGF-1R, U.S. patent application Ser. No. 12/772,645, filed Mar. 12, 2010) hPAM4 (anti-pancreatic cancer mucin, U.S. Pat. No. 7,282,567), hA20 (anti-CD20, U.S. Pat. No. 7,251,164), hA19 (anti-CD19, U.S. Pat. No. 7,109,304), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 7,662,378, U.S. patent application Ser. No. 12/846,062, filed Jul. 29, 2010), hRS7 (anti-EGP-1, U.S. Pat. No. 7,238,785), hMN-3 (anti-CEACAM6, U.S. Pat. No. 7,541,440), Ab124 and Ab125 (anti-CXCR4, U.S. Pat. No. 7,138,496) the Examples section of each cited patent or application incorporated herein by reference.

Candidate anti-HIV antibodies include the anti-envelope antibody described by Johansson et al. (AIDS. 2006 Oct. 3; 20(15):1911-5), as well as the anti-HIV antibodies described and sold by Polymun (Vienna, Austria), also described in U.S. Pat. Nos. 5,831,034, 5,911,989, and Vcelar et al., AIDS 2007; 21(16):2161-2170 and Joos et al., Antimicrob. Agents Chemother. 2006; 50(5):1773-9, all incorporated herein by reference.

Where bispecific antibodies are used, the second MAb may be selected from any anti-hapten antibody known in the art, including but not limited to h679 (U.S. Pat. No. 7,429,381) and 734 (U.S. Pat. Nos. 7,429,381; 7,563,439; 7,666,415; and 7,534,431), the Examples section of each of which is incorporated herein by reference.

Various other antibodies of use are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239 and U.S. Patent Application Publ. No. 20060193865; each incorporated herein by reference.) Such known antibodies are of use for detection and/or imaging of a variety of disease states or conditions (e.g., hMN-14 or TF2 (CEA-expressing carcinomas), hA20 or TF-4 (lymphoma), hPAM4 or TF-10 (pancreatic cancer), RS7 (lung, breast, ovarian, prostatic cancers), hMN-15 or hMN3 (inflammation), anti-gp120 and/or anti-gp41 (HIV), anti-platelet and anti-thrombin (clot imaging), anti-myosin (cardiac necrosis), anti-CXCR4 (cancer and inflammatory disease)).

Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312, 318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,15; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Antibody Fragments

Antibody fragments which recognize specific epitopes can be generated by known techniques. The antibody fragments are antigen binding portions of an antibody, such as $F(ab')_2$, Fab', $F(ab)_2$, Fab, Fv, sFv and the like. $F(ab')_2$ fragments can be produced by pepsin digestion of the antibody molecule and Fab' fragments can be generated by reducing disulfide bridges of the $F(ab')_2$ fragments. Alternatively, Fab' expression libraries can be constructed (Huse et al., 1989, Science, 246:1274-1281) to allow rapid and easy identification of monoclonal Fab' fragments with the desired specificity. An antibody fragment can be prepared by proteolytic hydrolysis of the full length antibody or by expression in E. coli or another host of the DNA coding for the fragment. These methods are described, for example, by Goldenberg, U.S. Pat. Nos. 4,036, 945 and 4,331,647 and references contained therein, which patents are incorporated herein in their entireties by reference. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

A single chain Fv molecule (scFv) comprises a $V_L$ domain and a $V_H$ domain. The $V_L$ and $V_H$ domains associate to form a target binding site. These two domains are further covalently linked by a peptide linker (L). Methods for making scFv molecules and designing suitable peptide linkers are described in U.S. Pat. Nos. 4,704,692, 4,946,778, R. Raag and M. Whitlow, "Single Chain Fvs." FASEB Vol 9:73-80 (1995) and R. E. Bird and B. W. Walker, "Single Chain Antibody Variable Regions," TIBTECH, Vol 9: 132-137 (1991), incorporated herein by reference.

An scFv library with a large repertoire can be constructed by isolating V-genes from non-immunized human donors using PCR primers corresponding to all known $V_H$, $V_{kappa}$ and $V_{80}$ gene families. See, e.g., Vaughn et al., Nat. Biotechnol., 14: 309-314 (1996). Following amplification, the $V_{kappa}$ and $V_{lambda}$ pools are combined to form one pool. These fragments are ligated into a phagemid vector. The scFv linker is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned for binding to the selected antigen.

Other antibody fragments, for example single domain antibody fragments, are known in the art and may be used in the claimed constructs. Single domain antibodies (VHH) may be obtained, for example, from camels, alpacas or llamas by standard immunization techniques. (See, e.g., Muyldermans et al., TIBS 26:230-235, 2001; Yau et al., J Immunol Methods 281:161-75, 2003; Maass et al., J Immunol Methods 324:13-25, 2007). The VHH may have potent antigen-binding capacity and can interact with novel epitopes that are inaccessible to conventional VH-VL pairs. (Muyldermans et al., 2001) Alpaca serum IgG contains about 50% camelid heavy chain only IgG antibodies (Cabs) (Maass et al., 2007). Alpacas may be immunized with known antigens and VHHs can be isolated that bind to and neutralize the target antigen (Maass et al., 2007). PCR primers that amplify virtually all alpaca VHH coding sequences have been identified and may be used to construct alpaca VHH phage display libraries, which can be used for antibody fragment isolation by standard biopanning techniques well known in the art (Maass et al., 2007). These and other known antigen-binding antibody fragments may be utilized in the claimed methods and compositions.

General Techniques for Antibody Cloning and Production

Various techniques, such as production of chimeric or humanized antibodies, may involve procedures of antibody cloning and construction. The antigen-binding $V_\kappa$ (variable light chain) and $V_H$ (variable heavy chain) sequences for an antibody of interest may be obtained by a variety of molecular cloning procedures, such as RT-PCR, 5'-RACE, and cDNA library screening. The V genes of a MAb from a cell that expresses a murine MAb can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci., USA*, 86: 3833 (1989)). Based on the V gene sequences, a humanized MAb can then be designed and constructed as described by Leung et al. (*Mol. Immunol.*, 32: 1413 (1995)).

cDNA can be prepared from any known hybridoma line or transfected cell line producing a murine MAb by general molecular cloning techniques (Sambrook et al., Molecular Cloning, A laboratory manual, $2^{nd}$ Ed (1989)). The $V_\kappa$ sequence for the MAb may be amplified using the primers VK1BACK and VK1FOR (Orlandi et al., 1989) or the extended primer set described by Leung et al. (*BioTechniques*, 15: 286 (1993)). The $V_H$ sequences can be amplified using the primer pair VH1BACK/VH1FOR (Orlandi et al., 1989) or the primers annealing to the constant region of murine IgG described by Leung et al. (Hybridoma, 13:469 (1994)). Humanized V genes can be constructed by a combination of long oligonucleotide template syntheses and PCR amplification as described by Leung et al. (*Mol. Immunol.*, 32: 1413 (1995)).

PCR products for $V_\kappa$ can be subcloned into a staging vector, such as a pBR327-based staging vector, VKpBR, that contains an Ig promoter, a signal peptide sequence and convenient restriction sites. PCR products for $V_H$ can be subcloned into a similar staging vector, such as the pBluescript-based VHpBS. Expression cassettes containing the $V_\kappa$ and $V_H$ sequences together with the promoter and signal peptide sequences can be excised from VKpBR and VHpBS and ligated into appropriate expression vectors, such as pKh and pG1g, respectively (Leung et al., Hybridoma, 13:469 (1994)). The expression vectors can be co-transfected into an appropriate cell and supernatant fluids monitored for production of a chimeric, humanized or human MAb. Alternatively, the $V_\kappa$ and $V_H$ expression cassettes can be excised and subcloned into a single expression vector, such as pdHL2, as described by Gillies et al. (*J. Immunol. Methods* 125:191 (1989) and also shown in Losman et al., Cancer, 80:2660 (1997)).

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. Pat. Nos. 7,531,327; 7,537,930 and 7,608,425; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression.

Bispecific and Multispecific Antibodies

Certain embodiments concern pretargeting methods with bispecific antibodies and hapten-bearing targetable constructs. Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, Nature, 1983; 305:537-540).

Another method for producing bispecific antibodies uses heterobifunctional cross-linkers to chemically tether two different monoclonal antibodies (Staerz, et al. Nature. 1985; 314:628-631; Perez, et al. Nature. 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. Proc Natl Acad Sci USA. 1986; 83:1453-1457). Other methods include improving the efficiency of generating hybrid hybridomas by gene transfer of distinct selectable markers via retrovirus-derived shuttle vectors into respective parental hybridomas, which are fused subsequently (DeMonte, et al. Proc Natl Acad Sci USA. 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv), as discussed above. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL), discussed in more detail below, has been utilized to produce combinations of virtually any desired antibodies, antibody fragments and other effector molecules (see, e.g., U.S. Patent Application Publ. Nos. 20060228357; 20060228300; 20070086942; 20070140966 and 20070264265, the Examples section of each incorporated herein by reference). The DNL technique allows the assembly of monospecific, bispecific or multispecific antibodies, either as naked antibody moieties or in combination with a wide range of other effector molecules such as immunomodulators, enzymes, chemotherapeutic agents, chemokines, cytokines, diagnostic agents, therapeutic agents, radionuclides, imaging agents, anti-angiogenic agents, growth factors, oligonucleotides, hormones, peptides, toxins, proapoptotic agents, or a combination thereof. Any of the techniques known in the art for making bispecific or multispecific antibodies may be utilized in the practice of the presently claimed methods.

Dock-and-Lock (DNL)

In preferred embodiments, bispecific or multispecific antibodies or other constructs may be produced using the dock-and-lock technology (see, e.g., U.S. Pat. Nos. 7,550,143; 7,521,056; 7,534,866; 7,527,787 and 7,666,400, the Examples section of each incorporated herein by reference). The DNL method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell. Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has $\alpha$ and $\beta$ isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci. USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell. Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human Mkt, the AD binds to a hydrophobic surface formed by the 23 amino-terminal residues (Colledge and Scott, Trends Cell Biol. 1999; 6:216). Thus, the dimerization domain and AKAP binding domain of human RII$\alpha$ are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human RII$\alpha$ and the AD of AKAP as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL constructs of different stoichiometry may be produced and used, including but not limited to dimeric, trimeric, tetrameric, pentameric and hexameric DNL constructs (see, e.g., U.S. Pat. Nos. 7,550,143; 7,521,056; 7,534,866; 7,527, 787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Pre-Targeting

Bispecific or multispecific antibodies may be utilized in pre-targeting techniques. Pre-targeting is a multistep process originally developed to resolve the slow blood clearance of directly targeting antibodies, which contributes to undesirable toxicity to normal tissues such as bone marrow. With pre-targeting, a radionuclide or other diagnostic or therapeutic agent is attached to a small delivery molecule (targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. Nos. 6,077,499; 7,011,812; 7,300,644; 7,074,405; 6,962,702; 7,387,772; 7,052,872; 7,138,103; 6,090,381; 6,472,511; 6,962,702; and 6,962,702, each incorporated herein by reference.

A pre-targeting method of treating or diagnosing a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents.

Immunoconjugates

Any of the antibodies, antibody fragments or antibody fusion proteins described herein may be conjugated to a chelating moiety or other carrier molecule to form an immunoconjugate. Methods for covalent conjugation of chelating moieties and other functional groups are known in the art and any such known method may be utilized.

For example, a chelating moiety or carrier can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995).

Alternatively, the chelating moiety or carrier can be conjugated via a carbohydrate moiety in the Fc region of the antibody. Methods for conjugating peptides to antibody components via an antibody carbohydrate moiety are well-known to those of skill in the art. See, for example, Shih et al., Int. J. Cancer 41: 832 (1988); Shih et al., Int. J. Cancer 46: 1101 (1990); and Shih et al., U.S. Pat. No. 5,057,313, the Examples section of which is incorporated herein by reference. The general method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody used as the antibody component of the immunoconjugate is an antibody fragment. However, it is possible to introduce a carbohydrate moiety into the light chain variable region of a full length antibody or antibody fragment. See, for example, Leung et al., J. Immunol. 154: 5919 (1995); U.S. Pat. Nos. 5,443,953 and 6,254,868, the Examples section of which is incorporated herein by reference. The engineered carbohydrate moiety is used to attach the functional group to the antibody fragment.

Other methods of conjugation of chelating agents to proteins are well known in the art (see, e.g., U.S. Pat. No. 7,563,433, the Examples section of which is incorporated herein by reference). Chelates may be directly linked to antibodies or peptides, for example as disclosed in U.S. Pat. No. 4,824,659, incorporated herein in its entirety by reference.

Click Chemistry

An alternative method for attaching chelating moieties, peptides or other functional groups to a targeting molecule involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tornoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for immunoconjugate formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2] azide-alkyne cycloaddition reaction (Id.) For example, cyclooctyne is a 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.)

Another type of copper-free click reaction was reported by Ning et al. (2010, Angew Chem hit Ed 49:3065-68), involving strain-promoted alkyne-nitrone cycloaddition. To address the slow rate of the original cyclooctyne reaction, electron-withdrawing groups are attached adjacent to the triple bond (Id.) Examples of such substituted cyclooctynes include difluorinated cyclooctynes, 4-dibenzocyclooctynol and azacyclooctyne (Id.) An alternative copper-free reaction involved strain-promoted alkyne-nitrone cycloaddition to give N-alkylated isoxazolines (Id.) The reaction was reported to have exceptionally fast reaction kinetics and was used in a one-pot three-step protocol for site-specific modification of peptides and proteins (Id.) Nitrones were prepared by the condensation of appropriate aldehydes with N-methylhydroxylamine and the cycloaddition reaction took place in a mixture of acetonitrile and water (Id.) These and other known click chemistry reactions may be used to attach chelating moieties to antibodies or other targeting molecules in vitro.

Methods of Administration

In various embodiments, bispecific antibodies and targetable constructs may be used for imaging normal or diseased tissue and organs (see, e.g. U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference in its Examples section).

The administration of a bispecific antibody (bsAb) and an $^{18}$F-labeled targetable construct may be conducted by administering the bsAb antibody at some time prior to administration of the targetable construct. The doses and timing of the reagents can be readily devised by a skilled artisan, and are dependent on the specific nature of the reagents employed. If a bsAb-F(ab')$_2$ derivative is given first, then a waiting time of 24-72 hr (alternatively 48-96 hours) before administration of the targetable construct would be appropriate. If an IgG-Fab' bsAb conjugate is the primary targeting vector, then a longer waiting period before administration of the targetable construct would be indicated, in the range of 3-10 days. After sufficient time has passed for the bsAb to target to the diseased tissue, the $^{18}$F-labeled targetable construct is administered. Subsequent to administration of the targetable construct, imaging can be performed.

Certain embodiments concern the use of multivalent target binding proteins which have at least three different target binding sites as described in patent application Ser. No. 60/220,782. Multivalent target binding proteins have been made by cross-linking several Fab-like fragments via chemical linkers. See U.S. Pat. Nos. 5,262,524; 5,091,542 and Landsdorp et al. Euro. J. Immunol. 16: 679-83 (1986). Multivalent target binding proteins also have been made by covalently linking several single chain Fv molecules (scFv) to form a single polypeptide. See U.S. Pat. No. 5,892,020. A multivalent target binding protein which is basically an aggregate of scFv molecules has been disclosed in U.S. Pat. Nos. 6,025,165 and 5,837,242. A trivalent target binding protein comprising three scFv molecules has been described in Krott et al. Protein Engineering 10(4): 423-433 (1997).

Alternatively, a technique known as "dock-and-lock" (DNL), described in more detail below, has been demonstrated for the simple and reproducible construction of a variety of multivalent complexes, including complexes comprising two or more different antibodies or antibody fragments. (See, e.g., U.S. Pat. Nos. 7,550,143; 7,521,056; 7,534,866; 7,527,787 and 7,666,400, the Examples section of each of which is incorporated herein by reference.) Such constructs are also of use for the practice of the claimed methods and compositions described herein.

A clearing agent may be used which is given between doses of the bispecific antibody (bsAb) and the targetable construct. A clearing agent of novel mechanistic action may be used, namely a glycosylated anti-idiotypic Fab' fragment targeted against the disease targeting arm(s) of the bsAb. In one example, anti-CEA (MN-14 Ab)×anti-peptide bsAb is given and allowed to accrete in disease targets to its maximum extent. To clear residual bsAb from circulation, an anti-idiotypic Ab to MN-14, termed WI2, is given, preferably as a glycosylated Fab' fragment. The clearing agent binds to the bsAb in a monovalent manner, while its appended glycosyl residues direct the entire complex to the liver, where rapid metabolism takes place. Then the $^{18}$F-labeled targetable construct is given to the subject. The WI2 Ab to the MN-14 arm of the bsAb has a high affinity and the clearance mechanism differs from other disclosed mechanisms (see Goodwin et al., ibid), as it does not involve cross-linking, because the WI2-Fab' is a monovalent moiety. However, alternative methods and compositions for clearing agents are known and any such known clearing agents may be used.

Formulation and Administration

The $^{18}$F-labeled molecules may be formulated to obtain compositions that include one or more pharmaceutically suitable excipients, one or more additional ingredients, or some combination of these. These can be accomplished by known methods to prepare pharmaceutically useful dosages, whereby the active ingredients (i.e., the $^{18}$F-labeled molecules) are combined in a mixture with one or more pharmaceutically suitable excipients. Sterile phosphate-buffered saline is one example of a pharmaceutically suitable excipient. Other suitable excipients are well known to those in the art. See, e.g., Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The preferred route for administration of the compositions described herein is parenteral injection. Injection may be intravenous, intraarterial, intralymphatic, intrathecal, or intracavitary (i.e., parenterally). In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hank's solution. Nonaqueous excipients such as fixed oils and ethyl oleate may also be used. A preferred excipient is 5% dextrose in saline. The excipient may contain minor amounts of additives such as substances that enhance isotonicity and chemical stability, including buffers and preservatives. Other methods of administration, including oral administration, are also contemplated.

Formulated compositions comprising $^{18}$F-labeled molecules can be used for intravenous administration via, for example, bolus injection or continuous infusion. Compositions for injection can be presented in unit dosage form, e.g., in ampoules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions may be administered in solution. The pH of the solution should be in the range of pH 5 to 9.5, preferably pH 6.5 to 7.5. The formulation thereof should be in a solution having a suitable pharmaceutically acceptable buffer such as phosphate, TRIS (hydroxymethyl)aminomethane-HCl or citrate and the like. Buffer concentrations should be in the range of 1 to 100 mM. The formulated solution may also contain a salt, such as sodium chloride or potassium chloride in a concentration of 50 to 150 mM. An effective amount of a stabilizing agent such as glycerol, albumin, a globulin, a detergent, a gelatin, a protamine or a salt of protamine may also be included. The compositions may be administered to a mammal subcutaneously, intravenously, intramuscularly or by other parenteral routes. Moreover, the administration may be by continuous infusion or by single or multiple boluses.

Where bispecific antibodies are administered, for example in a pretargeting technique, the dosage of an administered antibody for humans will vary depending upon such factors as the patient's age, weight, height, sex, general medical condition and previous medical history. Typically, for imaging purposes it is desirable to provide the recipient with a dosage of bispecific antibody that is in the range of from about 1 mg to 200 mg as a single intravenous infusion, although a lower or higher dosage also may be administered as circumstances dictate. Typically, it is desirable to provide the recipient with a dosage that is in the range of from about 10 mg per square meter of body surface area or 17 to 18 mg of the antibody for the typical adult, although a lower or higher dosage also may be administered as circumstances dictate. Examples of dosages of bispecific antibodies that may be administered to a human subject for imaging purposes are 1 to 200 mg, more preferably 1 to 70 mg, most preferably 1 to 20 mg, although higher or lower doses may be used.

In general, the dosage of $^{18}$F label to administer will vary depending upon such factors as the patient's age, weight, height, sex, general medical condition and previous medical history. Preferably, a saturating dose of the $^{18}$F-labeled molecules is administered to a patient. For administration of $^{18}$F-labeled molecules, the dosage may be measured by millicuries. A typical range for $^{18}$F imaging studies would be five to 10 mCi.

Administration of Peptides

Various embodiments of the claimed methods and/or compositions may concern one or more $^{18}$F-labeled peptides to be administered to a subject. Administration may occur by any route known in the art, including but not limited to oral, nasal, buccal, inhalational, rectal, vaginal, topical, orthotopic, intradermal, subcutaneous, intramuscular, intraperitoneal, intraarterial, intrathecal or intravenous injection. Where, for example, $^{18}$F-labeled peptides are administered in a pretargeting protocol, the peptides would preferably be administered i.v.

Unmodified peptides administered orally to a subject can be degraded in the digestive tract and depending on sequence and structure may exhibit poor absorption across the intestinal lining. However, methods for chemically modifying peptides to render them less susceptible to degradation by endogenous proteases or more absorbable through the alimentary tract are well known (see, for example, Blondelle et al., 1995, Biophys. J. 69:604-11; Ecker and Crooke, 1995, Biotechnology 13:351-69; Goodman and Ro, 1995, BURGER'S MEDICINAL CHEMISTRY AND DRUG DISCOVERY, VOL. I, ed. Wollf, John Wiley & Sons; Goodman and Shao, 1996, Pure & Appl. Chem. 68:1303-08). Methods for preparing libraries of peptide analogs, such as peptides containing D-amino acids; peptidomimetics consisting of organic molecules that mimic the structure of a peptide; or peptoids such as vinylogous peptoids, have also been described and may be used to construct peptide based $^{18}$F-labeled molecules suitable for oral administration to a subject.

In certain embodiments, the standard peptide bond linkage may be replaced by one or more alternative linking groups, such as $CH_2$—NH, $CH_2$—S, $CH_2$—$CH_2$, CH=CH, CO—$CH_2$, CHOH—$CH_2$ and the like. Methods for preparing peptide mimetics are well known (for example, Hruby, 1982, Life Sci 31:189-99; Holladay et al., 1983, Tetrahedron Lett. 24:4401-04; Jennings-White et al., 1982, Tetrahedron Lett. 23:2533; Almquiest et al., 1980, J. Med. Chem. 23:1392-98; Hudson et al., 1979, Int. J. Pept. Res. 14:177-185; Spatola et al., 1986, Life Sci 38:1243-49; U.S. Pat. Nos. 5,169,862; 5,539,085; 5,576,423, 5,051,448, 5,559,103.) Peptide mimetics may exhibit enhanced stability and/or absorption in vivo compared to their peptide analogs.

Alternatively, peptides may be administered by oral delivery using N-terminal and/or C-terminal capping to prevent exopeptidase activity. For example, the C-terminus may be capped using amide peptides and the N-terminus may be capped by acetylation of the peptide. Peptides may also be cyclized to block exopeptidases, for example by formation of cyclic amides, disulfides, ethers, sulfides and the like.

Peptide stabilization may also occur by substitution of D-amino acids for naturally occurring L-amino acids, particularly at locations where endopeptidases are known to act. Endopeptidase binding and cleavage sequences are known in the art and methods for making and using peptides incorporating D-amino acids have been described (e.g., U.S. Patent Application Publication No. 20050025709, McBride et al., filed Jun. 14, 2004, the Examples section of which is incorporated herein by reference). In certain embodiments, peptides and/or proteins may be orally administered by co-formulation with proteinase- and/or peptidase-inhibitors.

Other methods for oral delivery of therapeutic peptides are disclosed in Mehta ("Oral delivery and recombinant production of peptide hormones," June 2004, BioPharm International). The peptides are administered in an enteric-coated solid dosage form with excipients that modulate intestinal proteolytic activity and enhance peptide transport across the intestinal wall. Relative bioavailability of intact peptides using this technique ranged from 1% to 10% of the administered dosage. Insulin has been successfully administered in dogs using enteric-coated microcapsules with sodium cholate and a protease inhibitor (Ziv et al., 1994, J. Bone Miner. Res. 18 (Suppl. 2):792-94. Oral administration of peptides has been performed using acylcarnitine as a permeation enhancer and an enteric coating (Eudragit L30D-55, Rohm Pharma Polymers, see Mehta, 2004). Excipients of use for orally administered peptides may generally include one or more inhibitors of intestinal proteases/peptidases along with detergents or other agents to improve solubility or absorption of the peptide, which may be packaged within an enteric-coated capsule or tablet (Mehta, 2004). Organic acids may be included in the capsule to acidify the intestine and inhibit intestinal protease activity once the capsule dissolves in the intestine (Mehta, 2004). Another alternative for oral delivery of peptides would include conjugation to polyethylene glycol (PEG)-based amphiphilic oligomers, increasing absorption and resistance to enzymatic degradation (Soltero and Ekwuribe, 2001, Pharm. Technol. 6:110).

Imaging Using Labeled Molecules

Methods of imaging using labeled molecules are well known in the art, and any such known methods may be used with the $^{18}$F-labeled molecules disclosed herein. See, e.g., U.S. Pat. Nos. 6,241,964; 6,358,489; 6,953,567 and published U.S. Patent Application Publ. Nos. 20050003403; 20040018557; 20060140936, the Examples section of each incorporated herein by reference. See also, Page et al., Nuclear Medicine And Biology, 21:911-919, 1994; Choi et al., Cancer Research 55:5323-5329, 1995; Zalutsky et al., J. Nuclear Med., 33:575-582, 1992; Woessner et. al. Magn. Reson. Med. 2005, 53: 790-99.

In certain embodiments, $^{18}$F-labeled molecules may be of use in imaging normal or diseased tissue and organs, for example using the methods described in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference. Such imaging can be conducted by direct $^{18}$F labeling of the appropriate targeting molecules, or by a pretargeted imaging method, as described in Goldenberg et al. (2007, Update Cancer Ther. 2:19-31); Sharkey et al. (2008, Radiology 246:497-507); Goldenberg et al. (2008, J. Nucl. Med. 49:158-63); Sharkey et al. (2007, Clin. Cancer Res. 13:5777s-5585s); McBride et al. (2006, J. Nucl. Med. 47:1678-88); Goldenberg et al. (2006, J. Clin. Oncol. 24:823-85), see also U.S. Patent Publication Nos. 20050002945, 20040018557, 20030148409 and 20050014207, each incorporated herein by reference.

Methods of diagnostic imaging with labeled peptides or MAbs are well-known. For example, in the technique of immunoscintigraphy, ligands or antibodies are labeled with a gamma-emitting radioisotope and introduced into a patient. A gamma camera is used to detect the location and distribution of gamma-emitting radioisotopes. See, for example, Srivastava (ed.), RADIOLABELED MONOCLONAL ANTIBODIES FOR IMAGING AND THERAPY (Plenum Press 1988), Chase, "Medical Applications of Radioisotopes," in REMINGTON'S PHARMACEUTICAL SCIENCES, 18th Edition, Gennaro et al. (eds.), pp. 624-652 (Mack Publishing Co., 1990), and Brown, "Clinical Use of Monoclonal Antibodies," in BIOTECHNOLOGY AND PHARMACY 227-49, Pezzuto et al. (eds.) (Chapman & Hall 1993). Also preferred is the use of positron-emitting radionuclides (PET isotopes), such as with an energy of 511 keV, such as $^{18}$F, $^{68}$Ga, $^{64}$Cu, and $^{124}$I. Such radionuclides may be imaged by well-known PET scanning techniques.

In preferred embodiments, the $^{18}$F-labeled peptides, proteins and/or antibodies are of use for imaging of cancer. Examples of cancers include, but are not limited to, carcinoma, lymphoma, blastoma, sarcoma, and leukemia or lymphoid malignancies. More particular examples of such cancers are noted below and include: squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to detect or diagnose malignant or premalignant conditions. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be detected include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be detected include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, menangioma, melanoma, neuroblastoma, and retinoblastoma.

In a preferred embodiment, diseases that may be treated using the claimed compositions and methods include cardiovascular diseases, such as fibrin clots, atherosclerosis, myocardial ischemia and infarction. Antibodies to fibrin (e.g., scFv(59D8); T2G1s; MH1) are known and in clinical trials as imaging agents for disclosing said clots and pulmonary emboli, while anti-granulocyte antibodies, such as MN-3, MN-15, anti-NCA95, and anti-CD15 antibodies, can target myocardial infarcts and myocardial ischemia. (See, e.g., U.S. Pat. Nos. 5,487,892; 5,632,968; 6,294,173; 7,541,440, the Examples section of each incorporated herein by reference) Anti-macrophage, anti-low-density lipoprotein (LDL) and anti-CD74 (e.g., hLL1) antibodies can be used to target atherosclerotic plaques. Abciximab (anti-glycoprotein IIb/IIIa) has been approved for adjuvant use for prevention of restenosis in percutaneous coronary interventions and the treatment of unstable angina (Waldmann et al., 2000, Hematol 1:394-408). Anti-CD3 antibodies have been reported to reduce development and progression of atherosclerosis (Steffens et al., 2006, Circulation 114:1977-84). Treatment with blocking MIF antibody has been reported to induce regression of established atherosclerotic lesions (Sanchez-Madrid and Sessa, 2010, Cardiovasc Res 86:171-73). Antibodies against oxidized LDL also induced a regression of established atherosclerosis in a mouse model (Ginsberg, 2007, J Am Coll Cardiol 52:2319-21). Anti-ICAM-1 antibody was shown to reduce ischemic cell damage after cerebral artery occlusion in rats (Zhang et al., 1994, Neurology 44:1747-51). Commercially available monoclonal antibodies to leukocyte antigens are represented by: OKT anti-T-cell monoclonal antibodies (available from Ortho Pharmaceutical Company) which bind to normal T-lymphocytes; the monoclonal antibodies produced by the hybridomas having the ATCC accession numbers HB44, HB55, HB12, HB78 and HB2; G7E11, W8E7, NKP15 and G022 (Becton Dickinson); NEN9.4 (New England Nuclear); and FMC11 (Sera Labs). A description of antibodies against fibrin and platelet antigens is contained in Knight, Semin. Nucl. Med., 20:52-67 (1990).

In one embodiment, a pharmaceutical composition of the present invention may be used to treat a subject having a metabolic disease, such amyloidosis, or a neurodegenerative disease, such as Alzheimer's disease, amyotrophic lateral sclerosis (ALS), Parkinson's disease, Huntington's disease, olivopontocerebellar atrophy, multiple system atrophy, progressive supranuclear palsy, diffuse lewy body disease, corticodentatonigral degeneration, progressive familial myoclonic epilepsy, strionigral degeneration, torsion dystonia, familial tremor, Gilles de la Tourette syndrome or Hallervorden-Spatz disease. Bapineuzumab is in clinical trials for Alzheimer's disease therapy. Other antibodies proposed for therapy of Alzheimer's disease include Alz 50 (Ksiezak-Reding et al., 1987, J Biol Chem 263:7943-47), gantenerumab, and solanezumab. Infliximab, an anti-TNF-α antibody, has been reported to reduce amyloid plaques and improve cognition. Antibodies against mutant SOD1, produced by hybridoma cell lines deposited with the International Depositary Authority of Canada (accession Nos. ADI-290806-01, ADI-290806-$O_2$, ADI-290806-03) have been proposed for therapy of ALS, Parkinson's disease and Alzheimer's disease (see U.S. Patent Appl. Publ. No. 20090068194). Anti-CD3 antibodies have been proposed for therapy of type 1 diabetes (Cernea et al., 2010, Diabetes Metab Rev 26:602-05). In addition, a pharmaceutical composition of the present invention may be used to treat a subject having an immune-dysregulatory disorder, such as graft-versus-host disease or organ transplant rejection.

The exemplary conditions listed above that may be detected, diagnosed and/or imaged are not limiting. The skilled artisan will be aware that antibodies, antibody fragments or targeting peptides are known for a wide variety of conditions, such as autoimmune disease, cardiovascular disease, neurodegenerative disease, metabolic disease, cancer, infectious disease and hyperproliferative disease. Any such condition for which an $^{18}$F-labeled molecule, such as a protein or peptide, may be prepared and utilized by the methods described herein, may be imaged, diagnosed and/or detected as described herein.

Kits

Various embodiments may concern kits containing components suitable for imaging, diagnosing and/or detecting diseased tissue in a patient using labeled compounds. Exemplary kits may contain an antibody, fragment or fusion protein, such as a bispecific antibody of use in pretargeting methods as described herein. Other components may include a targetable construct for use with such bispecific antibodies. In preferred embodiments, the targetable construct is pre-conjugated to a chelating group that may be used to attach an Al$^{18}$F complex or a complex of $^{18}$F with a different metal. However, in alternative embodiments it is contemplated that a targetable construct may be attached to one or more different diagnostic agents, such as $^{68}$Ga.

If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used for certain applications.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

Example 1

$^{18}$F Labeling of Peptide IMP 272

The first peptide that was prepared and $^{18}$F-labeled was IMP 272:

(SEQ ID NO: 3)
DTPA-Gln-Ala-Lys(HSG)-D-Tyr-Lys(HSG)-NH$_2$

Acetate buffer solution—Acetic acid, 1.509 g was diluted in ~160 mL water and the pH was adjusted by the addition of 1 M NaOH then diluted to 250 mL to make a 0.1 M solution at pH 4.03.

Aluminum acetate buffer solution—A solution of aluminum was prepared by dissolving 0.1028 g of AlCl$_3$ hexahydrate in 42.6 mL DI water. A 4 mL aliquot of the aluminum solution was mixed with 16 mL of a 0.1 M NaOAc solution at pH 4 to provide a 2 mM Al stock solution.

IMP 272 acetate buffer solution—Peptide, 0.0011 g, 7.28×10$^{-7}$ mol IMP 272 was dissolved in 364 µL of the 0.1 M pH 4 acetate buffer solution to obtain a 2 mM stock solution of the peptide.

F-18 Labeling of IMP 272—A 3 µL aliquot of the aluminum stock solution was placed in a REACTI-VIAL™ and mixed with 50 µL $^{18}$F (as received) and 3 µL of the IMP 272 solution. The solution was heated in a heating block at 110° C. for 15 min and analyzed by reverse phase HPLC. The HPLC trace (not shown) showed 93% free $^{18}$F and 7% bound to the peptide. An additional 10 µL of the IMP 272 solution was added to the reaction and it was heated again and analyzed by reverse phase HPLC (not shown). The HPLC trace showed 8% $^{18}$F at the void volume and 92% of the activity attached to the peptide. The remainder of the peptide solution was incubated at room temperature with 150 µL PBS for ~1 hr and then examined by reverse phase HPLC. The HPLC (not shown) showed 58% $^{18}$F unbound and 42% still attached to the peptide. The data indicate that $^{18}$F-Al-DTPA complex may be unstable when mixed with phosphate.

Example 2

IMP 272 $^{18}$F Labeling with Other Metals

A ~3 µL aliquot of the metal stock solution (6×10$^{-9}$ mol) was placed in a polypropylene cone vial and mixed with 75 µL $^{18}$F (as received), incubated at room temperature for ~2 min and then mixed with 20 µL of a 2 mM (4×10$^{-8}$ mol) IMP 272 solution in 0.1 M NaOAc pH 4 buffer. The solution was heated in a heating block at 100° C. for 15 min and analyzed by reverse phase HPLC. IMP 272 was labeled with indium (24%), gallium (36%), zirconium (15%), lutetium (37%) and yttrium (2%) (not shown). These results demonstrate that the $^{18}$F metal labeling technique is not limited to an aluminum ligand, but can also utilize other metals as well. With different metal ligands, different chelating moieties may be utilized to optimize binding of an F-18-metal conjugate.

Example 3

Production and Use of a Serum-Stable $^{18}$F-Labeled Peptide IMP 449

IMP 449

(SEQ ID NO: 4)
NOTA-ITC benzyl-D-Ala-D-Lys(HSG)-D-Tyr-D-Lys(HSG)-NH$_2$

The peptide, IMP 448 D-Ala-D-Lys(HSG)-D-Tyr-D-Lys (HSG)-NH$_2$ (SEQ ID NO:5) was made on Sieber Amide resin by adding the following amino acids to the resin in the order shown: Aloc-D-Lys(Fmoc)-OH, Trt-HSG-OH, the Aloc was cleaved, Fmoc-D-Tyr(But)-OH, Aloc-D-Lys(Fmoc)-OH, Trt-HSG-OH, the Aloc was cleaved, Fmoc-D-Ala-OH with final Fmoc cleavage to make the desired peptide. The peptide was then cleaved from the resin and purified by HPLC to produce IMP 448, which was then coupled to ITC-benzyl NOTA.

IMP 448 (0.0757 g, 7.5×10$^{-5}$ mol) was mixed with 0.0509 g (9.09×10$^{-5}$ mol) ITC benzyl NOTA and dissolved in 1 mL water. Potassium carbonate anhydrous (0.2171 g) was then slowly added to the stirred peptide/NOTA solution. The reaction solution was pH 10.6 after the addition of all the carbonate. The reaction was allowed to stir at room temperature overnight. The reaction was carefully quenched with 1 M HCl after 14 hr and purified by HPLC to obtain 48 mg of IMP 449.

$^{18}$F Labeling of IMP 449

IMP 449 (0.002 g, 1.37×10$^{-6}$ mol) was dissolved in 686 µL (2 mM peptide solution) 0.1 M NaOAc pH 4.02. Three microliters of a 2 mM solution of Al in a pH 4 acetate buffer was mixed with 15 µL, 1.3 mCi of $^{18}$F. The solution was then mixed with 20 µL of the 2 mM IMP 449 solution and heated at 105° C. for 15 min. Reverse Phase HPLC analysis showed 35% ($t_R$~10 min) of the activity was attached to the peptide and 65% of the activity was eluted at the void volume of the column (3.1 min, not shown) indicating that the majority of activity was not associated with the peptide. The crude labeled mixture (5 µL) was mixed with pooled human serum and incubated at 37° C. An aliquot was removed after 15 min and analyzed by HPLC. The HPLC showed 9.8% of the activity was still attached to the peptide (down from 35%). Another aliquot was removed after 1 hr and analyzed by HPLC. The HPLC showed 7.6% of the activity was still attached to the peptide (down from 35%), which was essentially the same as the 15 min trace (data not shown).

High Dose $^{18}$F Labeling

Further studies with purified IMP 449 demonstrated that the $^{18}$F-labeled peptide was highly stable (91%, not shown) in human serum at 37° C. for at least one hour and was partially stable (76%, not shown) in human serum at 37° C. for at least four hours. Additional studies were performed in which the IMP 449 was prepared in the presence of ascorbic acid as a stabilizing agent. In those studies (not shown), the metal-$^{18}$F-peptide complex showed no detectable decomposition in serum after 4 hr at 37° C. The mouse urine 30 min after injection of $^{18}$F-labeled peptide was found to contain $^{18}$F bound to the peptide (not shown). These results demonstrate that the $^{18}$F-labeled peptides disclosed herein exhibit sufficient stability under approximated in vivo conditions to be used for $^{18}$F imaging studies.

Since IMP 449 peptide contains a thiourea linkage, which is sensitive to radiolysis, several products are observed by RP-HPLC. However, when ascorbic acid is added to the reaction mixture, the side products generated are markedly reduced.

Example 4

Preparation of DNL Constructs for $^{18}$F Imaging by Pretargeting

The DNL technique may be used to make dimers, trimers, tetramers, hexamers, etc. comprising virtually any antibodies or fragments thereof or other effector moieties. For certain preferred embodiments, IgG antibodies, Fab fragments or other proteins or peptides may be produced as fusion proteins containing either a DDD (dimerization and docking domain) or AD (anchoring domain) sequence. Bispecific antibodies may be formed by combining a Fab-DDD fusion protein of a first antibody with a Fab-AD fusion protein of a second antibody. Alternatively, constructs may be made that combine IgG-AD fusion proteins with Fab-DDD fusion proteins. For purposes of $^{18}$F detection, an antibody or fragment containing a binding site for an antigen associated with a target tissue to be imaged, such as a tumor, may be combined with a second antibody or fragment that binds a hapten on a targetable construct, such as IMP 449, to which a metal-$^{18}$F can be attached. The bispecific antibody (DNL construct) is administered to a subject, circulating antibody is allowed to clear from the blood and localize to target tissue, and the $^{18}$F-labeled targetable construct is added and binds to the localized antibody for imaging.

Independent transgenic cell lines may be developed for each Fab or IgG fusion protein. Once produced, the modules can be purified if desired or maintained in the cell culture supernatant fluid. Following production, any DDD$_2$-fusion protein module can be combined with any corresponding AD-fusion protein module to generate a bispecific DNL construct. For different types of constructs, different AD or DDD sequences may be utilized. The following DDD sequences are based on the DDD moiety of PKA RIIα, while the AD sequences are based on the AD moiety of the optimized synthetic AKAP-IS sequence (Alto et al., Proc. Natl. Acad. Sci. USA. 2003; 100:4445).

```
                                          (SEQ ID NO: 6)
DDD1: SHIQIPPGLTELLQGYTVEVLRQQPPDLVEFAVEYFTRLREARA (SEQ ID NO: 7)
DDD2: CGHIQIPPGLTELLQGYTVEVLRQQPPDLVEFAVEYFTRLREARA (SEQ ID NO: 8)
AD1:  QIEYLAKQIVDNAIQQA (SEQ ID NO: 9)
AD2:  CGQIEYLAKQIVDNAIQQAGC
```

The plasmid vector pdHL2 has been used to produce a number of antibodies and antibody-based constructs. See Gillies et al., J Immunol Methods (1989), 125:191-202; Losman et al., Cancer (Phila) (1997), 80:2660-6. The di-cistronic mammalian expression vector directs the synthesis of the heavy and light chains of IgG. The vector sequences are mostly identical for many different IgG-pdHL2 constructs, with the only differences existing in the variable domain (VH and VL) sequences. Using molecular biology tools known to those skilled in the art, these IgG expression vectors can be converted into Fab-DDD or Fab-AD expression vectors. To generate Fab-DDD expression vectors, the coding sequences for the hinge, CH2 and CH3 domains of the heavy chain are replaced with a sequence encoding the first 4 residues of the hinge, a 14 residue Gly-Ser linker and the first 44 residues of human Mkt (referred to as DDD1). To generate Fab-AD expression vectors, the sequences for the hinge, CH2 and CH3 domains of IgG are replaced with a sequence encoding the first 4 residues of the hinge, a 15 residue Gly-Ser linker and a 17 residue synthetic AD called AKAP-IS (referred to as AD1), which was generated using bioinformatics and peptide array technology and shown to bind RIIα dimers with a very high affinity (0.4 nM). See Alto, et al. Proc. Natl. Acad. Sci., U.S.A (2003), 100:4445-50.

Two shuttle vectors were designed to facilitate the conversion of IgG-pdHL2 vectors to either Fab-DDD1 or Fab-AD1 expression vectors, as described below.

Preparation of CH1

The CH1 domain was amplified by PCR using the pdHL2 plasmid vector as a template. The left PCR primer consisted of the upstream (5') end of the CH1 domain and a SacII restriction endonuclease site, which is 5' of the CH1 coding sequence. The right primer consisted of the sequence coding for the first 4 residues of the hinge followed by four glycines and a serine, with the final two codons (GS) comprising a Bam HI restriction site. The 410 by PCR amplimer was cloned into the pGemT PCR cloning vector (Promega, Inc.) and clones were screened for inserts in the T7 (5') orientation.

A duplex oligonucleotide was synthesized by to code for the amino acid sequence of DDD1 preceded by 11 residues of a linker peptide, with the first two codons comprising a BamHI restriction site. A stop codon and an EagI restriction site are appended to the 3' end. The encoded polypeptide sequence is shown below, with the DDD1 sequence underlined.

(SEQ ID NO: 10)
GSGGGGSGGGGSHIQIPPGLTELLQGYTVEVLRQQPPDLVEFAVEYFTRLR EARA

Two oligonucleotides, designated RIIA1-44 top and RIIA1-44 bottom, that overlap by 30 base pairs on their 3' ends, were synthesized (Sigma Genosys) and combined to comprise the central 154 base pairs of the 174 by DDD1 sequence. The oligonucleotides were annealed and subjected to a primer extension reaction with Taq polymerase. Following primer extension, the duplex was amplified by PCR. The amplimer was cloned into pGemT and screened for inserts in the T7 (5') orientation.

A duplex oligonucleotide was synthesized to code for the amino acid sequence of AD1 preceded by 11 residues of the linker peptide with the first two codons comprising a BamHI restriction site. A stop codon and an EagI restriction site are appended to the 3' end. The encoded polypeptide sequence is shown below, with the sequence of AD1 underlined.

GSGGGGSGGGGSQIEYLAKQIVDNAIQQA      (SEQ ID NO: 11)

Two complimentary overlapping oligonucleotides encoding the above peptide sequence, designated AKAP-IS Top and AKAP-IS Bottom, were synthesized and annealed. The duplex was amplified by PCR. The amplimer was cloned into the pGemT vector and screened for inserts in the T7 (5') orientation.

Ligating DDD1 with CH1

A 190 by fragment encoding the DDD1 sequence was excised from pGemT with BamHI and NotI restriction enzymes and then ligated into the same sites in CH1-pGemT to generate the shuttle vector CH1-DDD1-pGemT.

Ligating AD1 with CH1

A 110 by fragment containing the AD1 sequence was excised from pGemT with BamHI and NotI and then ligated into the same sites in CH1-pGemT to generate the shuttle vector CH1-AD1-pGemT.

Cloning CH1-DDD1 or CH1-AD1 into pdHL2-Based Vectors

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective pGemT shuttle vector.

Construction of h679-Fd-AD1-pdHL2 h679-Fd-AD1-pdHL2 is an expression vector for production of h679 Fab with AD1 coupled to the carboxyl terminal end of the CH1 domain of the Fd via a flexible Gly/Ser peptide spacer composed of 14 amino acid residues. A pdHL2-based vector containing the variable domains of h679 was converted to h679-Fd-AD1-pdHL2 by replacement of the SacII/EagI fragment with the CH1-AD1 fragment, which was excised from the CH1-AD1-SV3 shuttle vector with SacII and EagI.

Construction of C-DDD1-Fd-hMN-14-pdHL2

C-DDD1-Fd-hMN-14-pdHL2 is an expression vector for production of a stable dimer that comprises two copies of a fusion protein C-DDD1-Fab-hMN-14, in which DDD1 is linked to hMN-14 Fab at the carboxyl terminus of CH1 via a flexible peptide spacer. The plasmid vector hMN14(I)-pdHL2, which has been used to produce hMN-14 IgG, was converted to C-DDD1-Fd-hMN-14-pdHL2 by digestion with SacII and EagI restriction endonucleases to remove the CH1-CH3 domains and insertion of the CH1-DDD1 fragment, which was excised from the CH1-DDD1-SV3 shuttle vector with SacII and EagI.

The same technique has been utilized to produce plasmids for Fab expression of a wide variety of known antibodies, such as hLL1, hLL2, hPAM4, hR1, hRS7, hMN-14, hMN-15, hA19, hA20 and many others. Generally, the antibody variable region coding sequences were present in a pdHL2 expression vector and the expression vector was converted for production of an AD- or DDD-fusion protein as described above. The AD- and DDD-fusion proteins comprising a Fab fragment of any of such antibodies may be combined, in an approximate ratio of two DDD-fusion proteins per one AD-fusion protein, to generate a trimeric DNL construct comprising two Fab fragments of a first antibody and one Fab fragment of a second antibody.

C-DDD2-Fd-hMN-14-pdHL2

C-DDD2-Fd-hMN-14-pdHL2 is an expression vector for production of C-DDD2-Fab-hMN-14, which possesses a dimerization and docking domain sequence of DDD2 appended to the carboxyl terminus of the Fd of hMN-14 via a 14 amino acid residue Gly/Ser peptide linker. The fusion protein secreted is composed of two identical copies of hMN-14 Fab held together by non-covalent interaction of the DDD2 domains.

Two overlapping, complimentary oligonucleotides, which comprise the coding sequence for part of the linker peptide and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

The duplex DNA was ligated with the shuttle vector CH1-DDD1-pGemT, which was prepared by digestion with BamHI and PstI, to generate the shuttle vector CH1-DDD2-pGemT. A 507 by fragment was excised from CH1-DDD2-pGemT with SacII and EagI and ligated with the IgG expression vector hMN14(I)-pdHL2, which was prepared by digestion with SacII and EagI. The final expression construct was designated C-DDD2-Fd-hMN-14-pdHL2. Similar techniques have been utilized to generated DDD2-fusion proteins of the Fab fragments of a number of different humanized antibodies.

H679-Fd-AD2-pdHL2 h679-Fab-AD2, was designed to pair as B to C-DDD2-Fab-hMN-14 as A. h679-Fd-AD2-pdHL2 is an expression vector for the production of h679-Fab-AD2, which possesses an anchor domain sequence of AD2 appended to the carboxyl terminal end of the CH1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides (AD2 Top and AD2 Bottom), which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

The duplex DNA was ligated into the shuttle vector CH1-AD1-pGemT, which was prepared by digestion with BamHI and SpeI, to generate the shuttle vector CH1-AD2-pGemT. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Example 5

Generation of TF2 DNL Construct

A trimeric DNL construct designated TF2 was obtained by reacting C-DDD2-Fab-hMN-14 with h679-Fab-AD2. A pilot batch of TF2 was generated with >90% yield as follows. Protein L-purified C-DDD2-Fab-hMN-14 (200 mg) was mixed with h679-Fab-AD2 (60 mg) at a 1.4:1 molar ratio. The total protein concentration was 1.5 mg/ml in PBS containing 1 mM EDTA. Subsequent steps involved TCEP reduction, HIC chromatography, DMSO oxidation, and IMP 291 affinity chromatography. Before the addition of TCEP, SE-HPLC did not show any evidence of $a_2b$ formation. Addition of 5 mM TCEP rapidly resulted in the formation of $a_2b$ complex consistent with a 157 kDa protein expected for the binary structure. TF2 was purified to near homogeneity by IMP 291 affinity chromatography (not shown). IMP 291 is a synthetic peptide containing the HSG hapten to which the 679 Fab binds (Rossi et al., 2005, Clin Cancer Res 11:7122s-29s). SE-HPLC analysis of the IMP 291 unbound fraction demonstrated the removal of $a_4$, $a_2$ and free kappa chains from the product (not shown).

Non-reducing SDS-PAGE analysis demonstrated that the majority of TF2 exists as a large, covalent structure with a relative mobility near that of IgG (not shown). The additional bands suggest that disulfide formation is incomplete under the experimental conditions (not shown). Reducing SDS-PAGE shows that any additional bands apparent in the non-reducing gel are product-related (not shown), as only bands representing the constituent polypeptides of TF2 are evident. MALDI-TOF mass spectrometry (not shown) revealed a single peak of 156,434 Da, which is within 99.5% of the calculated mass (157,319 Da) of TF2.

The functionality of TF2 was determined by BIACORE assay. TF2, C-DDD1-hMN-14+h679-AD1 (used as a control sample of noncovalent $a_2b$ complex), or C-DDD2-hMN-14+ h679-AD2 (used as a control sample of unreduced $a_2$ and b components) were diluted to 1 µg/ml (total protein) and passed over a sensorchip immobilized with HSG. The response for TF2 was approximately two-fold that of the two control samples, indicating that only the h679-Fab-AD component in the control samples would bind to and remain on the sensorchip. Subsequent injections of WI2 IgG, an anti-idiotype antibody for hMN-14, demonstrated that only TF2 had a DDD-Fab-hMN-14 component that was tightly associated with h679-Fab-AD as indicated by an additional signal response. The additional increase of response units resulting from the binding of WI2 to TF2 immobilized on the sensor-chip corresponded to two fully functional binding sites, each contributed by one subunit of C-DDD2-Fab-hMN-14. This was confirmed by the ability of TF2 to bind two Fab fragments of WI2 (not shown).

Example 6

Production of TF10 DNL Construct

A similar protocol was used to generate a trimeric TF10 DNL construct, comprising two copies of a C-DDD2-Fab-hPAM4 and one copy of C-AD2-Fab-679. The TF10 bispecific ([hPAM4]$_2$×h679) antibody was produced using the method disclosed for production of the (anti CEA)$_2$×anti HSG bsAb TF2, as described above. The TF10 construct bears two humanized PAM4 Fabs and one humanized 679 Fab.

The two fusion proteins (hPAM4-DDD2 and h679-AD2) were expressed independently in stably transfected myeloma cells. The tissue culture supernatant fluids were combined, resulting in a two-fold molar excess of hPAM4-DDD2. The reaction mixture was incubated at room temperature for 24 hours under mild reducing conditions using 1 mM reduced glutathione. Following reduction, the DNL reaction was completed by mild oxidation using 2 mM oxidized glutathione. TF10 was isolated by affinity chromatography using IMP 291-affigel resin, which binds with high specificity to the h679 Fab.

Example 7

Sequence variants for DNL

In certain preferred embodiments, the AD and DDD sequences incorporated into the cytokine-MAb DNL complex comprise the amino acid sequences of AD1 or AD2 and DDD1 or DDD2, as discussed above. However, in alternative embodiments sequence variants of AD and/or DDD moieties may be utilized in construction of the DNL complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

PKA RIα
(SEQ ID NO: 12)
SLRECELYVQKHNIQALLKDVSIVQLCTARPERPMAFLREYFEKLEKEEAK

PKA RIβ
(SEQ ID NO: 13)
SLKGCELYVQLHGIQQVLKDCIVHLCISKPERPMKFLREHFEKLEKEENRQ
ILA

PKA RIIα
(SEQ ID NO: 14)
SHIQIPPGLTELLQGYTVEVGQQPPDLVDFAVEYFTRLREARRQ

PKA RIIβ
(SEQ ID NO: 15)
SIEIPAGLTELLQGFTVEVLRHQPADLLEFALQHFTRLQQENER

The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400: 493-99; Gold et al., 2006, Mol Cell 24:383-95; Kinderman et al., 2006, Mol Cell 24:397-408, the entire text of each of which is incorporated herein by reference.)

For example, Kinderman et al. (2006) examined the crystal structure of the AD-DDD binding interaction and concluded that the human DDD sequence contained a number of conserved amino acid residues that were important in either dimer formation or AKAP binding, underlined in SEQ ID NO:6 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

```
                                               (SEQ ID NO: 6)
SHIQIPPGLTELLQGYTVEVLRQQPPDLVEFAVEYFTRLREARA
```

Alto et al. (2003) performed a bioinformatic analysis of the AD sequence of various AKAP proteins to design an RII selective AD sequence called AKAP-IS (SEQ ID NO:8), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:8. The skilled artisan will realize that in designing sequence variants of the AD sequence, one would desirably avoid changing any of the underlined residues, while conservative amino acid substitutions might be made for residues that are less critical for DDD binding.

```
AKAP-IS sequence
QIEYLAKQIVDNAIQQA          (SEQ ID NO: 8)
```

Gold (2006) utilized crystallography and peptide screening to develop a SuperAKAP-IS sequence (SEQ ID NO:16), exhibiting a five order of magnitude higher selectivity for the R11 isoform of PKA compared with the RI isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL constructs. Other alternative sequences that might be substituted for the AKAP-IS AD sequence are shown in SEQ ID NO:17-19. Substitutions relative to the AKAP-IS sequence are underlined. It is anticipated that, as with the AD2 sequence shown in SEQ ID NO:9, the AD moiety may also include the additional N-terminal residues cysteine and glycine and C-terminal residues glycine and cysteine.

```
SuperAKAP-IS
QIEYVAKQIVDYAIHQA          (SEQ ID NO: 16)

Alternative AKAP sequences
QIEYKAKQIVDHAIHQA          (SEQ ID NO: 17)

QIEYHAKQIVDHAIHQA          (SEQ ID NO: 18)

QIEYVAKQIVDHAIHQA          (SEQ ID NO: 19)
```

Stokka et al. (2006) also developed peptide competitors of AKAP binding to PKA, shown in SEQ ID NO:20-22. The peptide antagonists were designated as Ht31 (SEQ ID NO:20), RIAD (SEQ ID NO:21) and PV-38 (SEQ ID NO:22). The Ht-31 peptide exhibited a greater affinity for the RII isoform of PKA, while the RIAD and PV-38 showed higher affinity for RI.

```
Ht31
DLIEEAASRIVDAVIEQVKAAGAY   (SEQ ID NO: 20)

RIAD
LEQYANQLADQIIKEATE         (SEQ ID NO: 21)

PV-38
FEELAWKIAKMIWSDVFQQC       (SEQ ID NO: 22)
```

Hundsrucker et al. (2006) developed still other peptide competitors for AKAP binding to PKA, with a binding constant as low as 0.4 nM to the DDD of the RII form of PKA. The sequences of various AKAP antagonistic peptides is provided in Table 1 of Hundsrucker et al. (incorporated herein by reference). Residues that were highly conserved among the AD domains of different AKAP proteins are indicated below by underlining with reference to the AKAP IS sequence (SEQ ID NO:8). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence are shown in SEQ ID NO:23-25.

```
AKAP-IS
QIEYLAKQIVDNAIQQA          (SEQ ID NO: 8)

AKAP7δ-wt-pep
PEDAELVRLSKRLVENAVLKAVQQY  (SEQ ID NO: 23)

AKAP7δ-L304T-pep
PEDAELVRTSKRLVENAVLKAVQQY  (SEQ ID NO: 24)

AKAP7δ-L308D-pep
PEDAELVRLSKRDVENAVLKAVQQY  (SEQ ID NO: 25)
```

Carr et al. (2001) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:6. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

```
                                               (SEQ ID NO: 6)
SHIQIPPGLTELLQGYTVEVLRQQPPDLVEFAVEYFTRLREARA
```

Example 8

In Vivo Studies with Pretargeting Antibody and $^{18}$F-Labeled Peptide $^{18}$F-labeled IMP 449 was prepared as follows. The $^{18}$F, 54.7 mCi in ~0.5 mL was mixed with 3 μL, 2 mM Al in 0.1 M NaOAc pH 4 buffer. After 3 min 10 µL of 0.05 M IMP 449 in 0.5 M pH 4 NaOAc buffer was added and the reaction was heated in a 96° C. heating block for 15 min. The crude labeled peptide was then purified by HPLC on a $C_{18}$ column. The HPLC purified peptide sample was further processed by diluting the fractions of interest two fold in water and placing the solution in the barrel of a 1 cc WATERS® HLB column. The cartridge was eluted with 3×1 mL water to remove acetonitrile and TFA followed by 400 µL 1:1 EtOH/$H_2O$ to elute the $^{18}F$-labeled peptide. The purified [$Al^{18}F$] IMP 449 eluted as a single peak on an analytical HPLC $C_{18}$ column (not shown).

Taconic nude mice bearing the four slow-growing sc CaPan1 xenografts were used for in vivo studies. Three of the mice were injected with TF10 (162 µg) followed with [$Al^{18}F$] IMP 449 18 h later. TF10 is a humanized bispecific antibody of use for tumor imaging studies, with divalent binding to the PAM-4 defined tumor antigen and monovalent binding to HSG (see, e.g., Gold et al., 2007, J. Clin. Oncol. 25(18S): 4564). One mouse was injected with peptide alone. All of the mice were necropsied at 1 h post peptide injection. Tissues were counted immediately. Comparison of mean distributions showed substantially higher levels of $^{18}F$-labeled peptide localized in the tumor than in any normal tissues in the presence of tumor-targeting bispecific antibody.

Tissue uptake was similar in animals given the [$Al^{18}F$] IMP 449 alone or in a pretargeting setting (Table 2). Uptake in the human pancreatic cancer xenograft, CaPanl, at 1 h was increased 5-fold in the pretargeted animals as compared to the peptide alone (4.6±0.9% ID/g vs. 0.89% ID/g). Exceptional tumor/nontumor ratios were achieved at this time (e.g., tumor/blood and liver ratios were 23.4±2.0 and 23.5±2.8, respectively).

TABLE 2

Tissue uptake at 1 h post peptide injection, mean and the individual animals:

| Tissue | | TF10 (162 µg) -→ 18 h → [$Al^{18}F$] IMP 449 (10:1) | | | | [$Al^{18}F$] IMP 449 alone |
|---|---|---|---|---|---|---|
| | n | Mean | SD | Animal 1 | Animal 2 | Animal 3 | Animal 1 |
| Tumor (mass) | 3 | 4.591 | 0.854 | 4.330 (0.675 g) | 5.546 (0.306 g) | 3.898 (0.353 g) | 0.893 (0.721 g) |
| Liver | 3 | 0.197 | 0.041 | 0.163 | 0.242 | 0.186 | 0.253 |
| Spleen | 3 | 0.202 | 0.022 | 0.180 | 0.224 | 0.200 | 0.226 |
| Kidney | 3 | 5.624 | 0.531 | 5.513 | 6.202 | 5.158 | 5.744 |
| Lung | 3 | 0.421 | 0.197 | 0.352 | 0.643 | 0.268 | 0.474 |

TABLE 2-continued

Tissue uptake at 1 h post peptide injection, mean and the individual animals:

| Tissue | n | TF10 (162 µg) -→ 18 h → [$Al^{18}F$] IMP 449 (10:1) | | | | [$Al^{18}F$] IMP 449 alone |
|---|---|---|---|---|---|---|
| | | Mean | SD | Animal 1 | Animal 2 | Animal 3 | Animal 1 |
| Blood | 3 | 0.196 | 0.028 | 0.204 | 0.219 | 0.165 | 0.360 |
| Stomach | 3 | 0.123 | 0.046 | 0.080 | 0.172 | 0.118 | 0.329 |
| Small Int. | 3 | 0.248 | 0.042 | 0.218 | 0.295 | 0.230 | 0.392 |
| Large Int. | 3 | 0.141 | 0.094 | 0.065 | 0.247 | 0.112 | 0.113 |
| Pancreas | 3 | 0.185 | 0.078 | 0.259 | 0.194 | 0.103 | 0.174 |
| Spine | 3 | 0.394 | 0.427 | 0.140 | 0.888 | 0.155 | 0.239 |
| Femur | 3 | 3.899 | 4.098 | 2.577 | 8.494 | 0.625 | 0.237 |
| Brain | 3 | 0.064 | 0.041 | 0.020 | 0.072 | 0.100 | 0.075 |
| Muscle | 3 | 0.696 | 0.761 | 0.077 | 1.545 | 0.465 | 0.162 |

Example 9

Biodistribution of [$Al^{18}F$] IMP 449 with Pretargeting Antibody

The goal of the study was to examine biodistribution of [$Al^{18}F$] IMP 449 in nude mice bearing sc LS174 T xenografts after pretargeting with bispecific antibody TF2.

[$Al^{18}F$] IMP 449: Labeling was performed as described above except the $^{18}F$ was purified on a QMA cartridge before labeling as described by Kim et. al. (Applied Radiation and Isotopes 61, 2004, 1241-46). The column was eluted with 1 mL 0.4 M $KHCO_3$ in 200 µL fractions. The pH of the $^{18}F$ solution was adjusted with 10 µL of glacial acetic acid and $^{18}F$ from the peak fraction was mixed with 3 µL of 2 mM Al in 0.1 M pH 4 NaOAc buffer. The sample was then mixed with 10 µL of 0.05 M IMP 449 in 0.5 M NaOAc buffer at pH 4 and the reaction solution was heated at 94° C. for 15 min. The [$Al^{18}F$] IMP 449 was purified by RP-HPLC. The fraction containing the product was put through an HLB column to exchange the buffer. The product was eluted with 400 µL 1:1 EtOH:$H_2O$, Since the yield was low, the specific activity was low and more peptide was injected into mice, resulting in a bsMAb: peptide ratio of 6.9:1 instead of 10:1.

Results

The biodistribution of pretargeted $^{18}F$ labeled IMP 449 in mice is summarized in Table 3. The labeled peptide showed a high level of localization to tumor tissues in the presence of the bispecific TF2 antibody. In the absence of TF2, the labeled peptide did not show significantly higher localization to tumor than to normal tissues (not shown).

TABLE 3

Mice were injected with TF2 (163.2 µg, 1.035 × $10^{-9}$ mol) i.v. followed by [$Al^{18}F$] IMP 449 (1.5 × $10^{-10}$ mol) 16 h later. Peptide tissue uptake (% ID/g) at 1 h post peptide injection is shown below.

| Tissue | n | Mean | SD | Animal 1 | Animal 2 | Animal 3 | Animal 4 | Animal 5 |
|---|---|---|---|---|---|---|---|---|
| Tumor | 5 | 7.624 | 3.080 | 5.298 | 7.848 | 12.719 | 5.118 | 7.136 |
| Liver | 5 | 0.172 | 0.033 | 0.208 | 0.143 | 0.196 | 0.131 | 0.180 |
| Spleen | 5 | 0.142 | 0.059 | 0.239 | 0.081 | 0.132 | 0.118 | 0.140 |
| Kidney | 5 | 2.191 | 0.125 | 2.313 | 2.141 | 2.154 | 2.319 | 2.027 |
| Lung | 5 | 0.315 | 0.094 | 0.474 | 0.230 | 0.300 | 0.305 | 0.265 |
| Blood | 5 | 0.269 | 0.143 | 0.431 | 0.395 | 0.132 | 0.126 | 0.260 |
| Stomach | 5 | 0.218 | 0.341 | 0.827 | 0.041 | 0.098 | 0.054 | 0.070 |
| Small Int. | 5 | 0.351 | 0.313 | 0.903 | 0.185 | 0.297 | 0.170 | 0.198 |
| Large Int. | 5 | 0.069 | 0.028 | 0.076 | 0.043 | 0.111 | 0.073 | 0.042 |
| Femur | 5 | 0.625 | 0.358 | 0.869 | 0.146 | 0.811 | 0.957 | 0.344 |
| Spine | 5 | 0.585 | 0.569 | 0.159 | 0.119 | 0.493 | 1.526 | 0.626 |
| Brain | 5 | 0.029 | 0.005 | 0.033 | 0.021 | 0.035 | 0.026 | 0.028 |

TABLE 3-continued

Mice were injected with TF2 (163.2 μg, 1.035 × 10⁻⁹ mol) i.v. followed by [Al¹⁸F] IMP 449 (1.5 × 10⁻¹⁰ mol) 16 h later. Peptide tissue uptake (% ID/g) at 1 h post peptide injection is shown below.

| Tissue | n | Mean | SD | Animal 1 | Animal 2 | Animal 3 | Animal 4 | Animal 5 |
|---|---|---|---|---|---|---|---|---|
| Muscle | 5 | 0.736 | 0.970 | 0.190 | 0.064 | 0.494 | 2.438 | 0.496 |
| Body Wt. | 5 | 24.69 | 1.20 | 23.05 | 26.36 | 24.45 | 24.48 | 25.11 |

This study shows that the simple, reproducible methods and compositions described herein produce $^{18}$F-labeled targeting peptides suitable for use in in vivo imaging of a variety of disease states. The skilled artisan will realize that the bispecific antibodies disclosed above are not limiting, but may comprise any known antibodies against a wide variety of disease or pathogen target antigens. Nor is the method limited to pretargeting with bispecific antibodies. In other embodiments, molecules or complexes that directly bind to target cells, tissues or organisms to be imaged may be labeled with $^{18}$F using the methods disclosed herein and administered to a subject for PET imaging (see Examples below).

The Al$^{18}$F-labeled peptides, exemplified by IMP 449, are sufficiently stable under in vivo conditions to be utilized in known imaging protocols, such as PET scanning. Further, the claimed methods result in preparation of $^{18}$F-labeled targeting peptides that are ready for injection within 1 hour of preparation time, well within the decay time of $^{18}$F to allow suitable imaging procedures to be performed. Finally, the described and claimed methods result in minimal exposure of the operator to radioisotope exposure, compared with known methods of preparing $^{18}$F-labeled compounds for imaging studies.

Example 10

In Vivo Imaging Using $^{18}$F-Labeled Peptides and Comparison with $^{18}$F[FDG]

In vivo imaging techniques using pretargeting with bispecific antibodies and labeled targeting peptides were used to successfully detect tumors of relatively small size. The $^{18}$F was purified on a WATERS® ACCELL™ Plus QMA Light cartridge. The $^{18}$F eluted with 0.4 M KHCO$_3$ was mixed with 3 μL 2 mM Al$^{3+}$ in a pH 4 acetate buffer. The Al$^{18}$F solution was then injected into the ascorbic acid IMP 449 labeling vial and heated to 105° C. for 15 min. The reaction solution was cooled and mixed with 0.8 mL DI water. The reaction contents were loaded on a WATERS® OASIS® 1 cc HLB Column and eluted with 2×200 μL 1:1 EtOH/H$_2$O. TF2 was prepared as described above. TF2 binds divalently to carcinoembryonic antigen (CEA) and monovalently to the synthetic hapten, HSG (histamine-succinyl-glycine).

Biodistribution and microPET Imaging.

Six-week-old NCr nu-m female nude mice were implanted s.c. with the human colonic cancer cell line, LS174T (ATCC, Manassas, Va.). When tumors were visibly established, pretargeted animals were injected intravenously with 162 μg (~1 nmole/0.1 mL) TF2 or TF10 (control non-targeting tri-Fab bsMAb), and then 16-18 h later, ~0.1 nmol of [Al$^{18}$F] IMP 449 (84 μCi, 3.11 MBq/0.1 mL) was injected intravenously. Other non-pretargeted control animals received $^{18}$F alone (150 μCi, 5.5 MBq), Al$^{18}$F complex alone (150 μCi, 5.55 MBq), the [Al$^{18}$F]IMP 449 peptide alone (84 μCi, 3.11 MBq), or [$^{18}$F]FDG (150 μCi, 5.55 MBq). $^{18}$F and [$^{18}$F]FDG were obtained on the day of use from IBA Molecular (Somerset, N.J.). Animals receiving [$^{18}$F]FDG were fasted overnight, but water was given ad libitum.

At 1.5 h after the radiotracer injection, animals were anesthetized, bled intracardially, and necropsied. Tissues were weighed and counted together with a standard dilution prepared from each of the respective products. Due to the short physical half-life of $^{18}$F, standards were interjected between each group of tissues from each animal. Uptake in the tissues is expressed as the counts per gram divided by the total injected activity to derive the percent-injected dose per gram (% ID/g).

Two types of imaging studies were performed. In one set, 3 nude mice bearing small LS174T subcutaneous tumors received either the pretargeted [Al$^{18}$F] IMP 449, [Al$^{18}$F] IMP 449 alone (not pretargeted), both at 135 μCi (5 MBq; 0.1 nmol), or [$^{18}$F]FDG (135 μCi, 5 MBq). At 2 h after the intravenous radiotracer injection, the animals were anesthetized with a mixture of O$_2$/N$_2$O and isoflurane (2%) and kept warm during the scan, performed on an INVEON® animal PET scanner (Siemens Preclinical Solutions, Knoxyille, Tenn.).

Representative coronal cross-sections (0.8 mm thick) in a plane located approximately in the center of the tumor were displayed, with intensities adjusted until pixel saturation occurred in any region of the body (excluding the bladder) and without background adjustment.

In a separate dynamic imaging study, a single LS174T-bearing nude mouse that was given the TF2 bsMAb 16 h earlier was anesthetized with a mixture of O$_2$/N$_2$O and isoflurane (2%), placed supine on the camera bed, and then injected intravenously with 219 μCi (8.1 MBq) [Al$^{18}$F] IMP 449 (0.16 nmol). Data acquisition was immediately initiated over a period of 120 minutes. The scans were reconstructed using OSEM3D/MAP. For presentation, time-frames ending at 5, 15, 30, 60, 90, and 120 min were displayed for each cross-section (coronal, sagittal, and transverse). For sections containing tumor, at each interval the image intensity was adjusted until pixel saturation first occurred in the tumor. Image intensity was increased as required over time to maintain pixel saturation within the tumor. Coronal and sagittal cross-sections without tumor taken at the same interval were adjusted to the same intensity as the transverse section containing the tumor. Background activity was not adjusted.

Results

While $^{18}$F alone and [Al$^{18}$F] complexes had similar uptake in all tissues, considerable differences were found when the complex was chelated to IMP 449 (Table 4). The most striking differences were found in the uptake in the bone, where the non-chelated $^{18}$F was 60- to nearly 100-fold higher in the scapula and ~200-fold higher in the spine. This distribution is expected since $^{18}$F, or even a metal-fluoride complex, is known to accrete in bone (Franke et al. 1972, Radiobiol. Radiother. (Berlin) 13:533). Higher uptake was also observed in the tumor and intestines as well as in muscle and blood. The chelated [Al$^{18}$F] IMP 449 had significantly lower uptake in all the tissues except the kidneys, illustrating the ability of the chelate-complex to be removed efficiently from the body by urinary excretion.

Pretargeting the [Al$^{18}$F] IMP 449 using the TF2 anti-CEA bsMAb shifted uptake to the tumor, increasing it from 0.20±0.05 to 6.01±1.72% injected dose per gram at 1.5 h, while uptake in the normal tissues was similar to the [Al$^{18}$F] IMP 449 alone. Tumor/nontumor ratios were 146±63, 59±24, 38±15, and 2.0±1.0 for the blood, liver, lung, and kidneys, respectively, with other tumor/tissue ratios >100:1 at this time. Although both $^{18}$F alone and [Al$^{18}$F] alone had higher uptake in the tumor than the chelated [Al$^{18}$F] IMP 449, yielding tumor/blood ratios of 6.7±2.7 and 11.0±4.6 vs. 5.1±1.5, respectively, tumor uptake and tumor/blood ratios were significantly increased with pretargeting (all P values <0.001).

Biodistribution was also compared to the most commonly used tumor imaging agent, [$^{18}$F]FDG, which targets tissues with high glucose consumption and metabolic activity (Table 4). Its uptake was appreciably higher than the [Al$^{18}$F] IMP 449 in all normal tissues, except the kidney. Tumor uptake was similar for both the pretargeted [Al$^{18}$F] IMP 449 and [$^{18}$F]FDG, but because of the higher accretion of [$^{18}$F]FDG in most normal tissues, tumor/nontumor ratios with [$^{18}$F]FDG were significantly lower than those in the pretargeted animals (all P values <0.001).

TABLE 4

Biodistribution of TF2-pretargeted [Al$^{18}$F] IMP 449 and other control $^{18}$F-labeled agents in nude mice bearing LS174T human colonic xenografts. For pretargeting, animals were given TF2 16 h before the injection of the [Al$^{18}$F] IMP 449. All injections were administered intravenously.

| | Percent Injected Dose Per Gram (Mean ± SD) at 1.5 hr Post-Injection | | | | |
|---|---|---|---|---|---|
| | $^{18}$F alone | [Al$^{18}$F] alone | [Al$^{18}$F] IMP 449 alone | TF2-pretargeted [Al$^{18}$F] IMP 449 | [$^{18}$F]FDG |
| Tumor | 1.02 ± 0.45 | 1.38 ± 0.39 | 0.20 ± 0.05 | 6.01 ± 1.72 | 7.25 ± 2.54 |
| Liver | 0.11 ± 0.02 | 0.12 ± 0.02 | 0.08 ± 0.03 | 0.11 ± 0.03 | 1.34 ± 0.36 |
| Spleen | 0.13 ± 0.06 | 0.10 ± 0.03 | 0.08 ± 0.02 | 0.08 ± 0.02 | 2.62 ± 0.73 |
| Kidney | 0.29 ± 0.07 | 0.25 ± 0.07 | 3.51 ± 0.56 | 3.44 ± 0.99 | 1.50 ± 0.61 |
| Lung | 0.26 ± 0.08 | 0.38 ± 0.19 | 0.11 ± 0.03 | 0.17 ± 0.04 | 3.72 ± 1.48 |
| Blood | 0.15 ± 0.03 | 0.13 ± 0.03 | 0.04 ± 0.01 | 0.04 ± 0.02 | 0.66 ± 0.19 |
| Stomach | 0.21 ± 0.13 | 0.15 ± 0.05 | 0.20 ± 0.32 | 0.12 ± 0.18 | 2.11 ± 1.04 |
| Small Int. | 1.53 ± 0.33 | 1.39 ± 0.34 | 0.36 ± 0.23 | 0.27 ± 0.10 | 1.77 ± 0.61 |
| Large Int. | 1.21 ± 0.13 | 1.78 ± 0.70 | 0.05 ± 0.04 | 0.03 ± 0.01 | 2.90 ± 0.79 |
| Scapula | 6.13 ± 1.33 | 9.83 ± 2.31 | 0.08 ± 0.06 | 0.04 ± 0.02 | 10.63 ± 5.88 |
| Spine | 19.88 ± 2.12 | 19.03 ± 2.70 | 0.13 ± 0.14 | 0.08 ± 0.03 | 4.21 ± 1.79 |
| Muscle | 0.16 ± 0.05 | 0.58 ± 0.36 | 0.06 ± 0.05 | 0.10 ± 0.20 | 4.35 ± 3.01 |
| Brain | 0.15 ± 0.06 | 0.13 ± 0.03 | 0.01 ± 0.01 | 0.01 ± 0.00 | 10.71 ± 4.53 |
| Tumor wt (g) | 0.29 ± 0.07 | 0.27 ± 0.10 | 0.27 ± 0.08 | 0.33 ± 0.11 | 0.25 ± 0.21 |
| N | 6 | 7 | 8 | 7 | 5 |

Several animals were imaged to further analyze the biodistribution of [Al$^{18}$F] IMP 449 alone or [Al$^{18}$F] IMP 449 pretargeted with TF2, as well [$^{18}$F]FDG. Static images initiated at 2.0 h after the radioactivity was injected corroborated the previous tissue distribution data showing uptake almost exclusively in the kidneys (FIG. 1). A 21-mg tumor was easily visualized in the pretargeted animal, while the animal given the [Al$^{18}$F] IMP 449 alone failed to localize the tumor, having only renal uptake. No evidence of bone accretion was observed, suggesting that the Al$^{18}$F was bound firmly to IMP 449. This was confirmed in another pretargeted animal that underwent a dynamic imaging study that monitored the distribution of the [Al$^{18}$F] IMP 449 in 5-min intervals over 120 minutes (FIG. 2). Coronal and sagittal slices showed primarily cardiac, renal, and some hepatic uptake over the first 5 min, but heart and liver activity decreased substantially over the next 10 min, while the kidneys remained prominent throughout the study. There was no evidence of activity in the intestines or bone over the full 120-min scan. Uptake in a 35-mg LS174T tumor was first observed at 15 min, and by 30 min, the signal was very clearly delineated from background, with intense tumor activity being prominent during the entire 120-min scanning.

In comparison, static images from an animal given [$^{18}$F]FDG showed the expected pattern of radioactivity in the bone, heart muscle, and brain observed previously (McBride et al., 2006, J. Nucl. Med. 47:1678; Sharkey et al., 2008, Radiology 246:497), with considerably more background activity in the body (FIG. 1). Tissue uptake measured in the 3 animals necropsied at the conclusion of the static imaging study confirmed much higher tissue $^{18}$F radioactivity in all tissues (not shown). While tumor uptake with [$^{18}$F]FDG was higher in this animal than in the pretargeted one, tumor/blood ratios were more favorable for pretargeting; and with much less residual activity in the body, tumor visualization was enhanced by pretargeting.

These studies demonstrate that a hapten-peptide used in pretargeted imaging can be rapidly labeled (60 min total preparation time) with $^{18}$F by simply forming an aluminum-fluoride complex that can then be bound by a suitable chelate and incorporated into the hapten-peptide. This can be made more general by simply coupling the [Al$^{18}$F]-chelate to any molecule that can be attached to the chelating moiety and be subsequently purified. In preferred embodiments, the percentage incorporation of label and specific activity of the labeled compound are sufficient that purification of the labeled molecule is not necessary.

This report describes a direct, facile, and rapid method of binding $^{18}$F to various compounds via an aluminum conjugate. The [Al$^{18}$F] peptide was stable in vitro and in vivo when bound by a NOTA-based chelate. Yields were within the range found with conventional $^{18}$F labeling procedures. These results further demonstrate the feasibility of PET imaging using metal$^{18}$F chelated to a wide variety of targeting molecules.

Example 11

Preparation and Labeling of IMP 460 with Al—$^{18}$F

IMP 460 NODA-Ga-D-Ala-D-Lys(HSG)-D-Tyr-D-Lys(HSG)-NH$_2$ (SEQ ID NO:26) was chemically synthesized. The NODA-Ga ligand was purchased from CHEMATECH® and attached on the peptide synthesizer like the other amino acids. The peptide was synthesized on Sieber amide resin with the amino acids and other agents added in the following order Aloc-D-Lys(Fmoc)-OH, Trt-HSG-OH, Aloc removal, Fmoc-D-Tyr(But)-OH, Aloc-D-Lys(Fmoc)-OH, Trt-HSG-OH, Aloc removal, Fmoc-D-Ala-OH, and NODA-GA(tBu)$_3$. The peptide was then cleaved and purified by HPLC to afford the product. HRMS C61H92N18O18.

Radiolabeling of IMP 460

IMP 460 (0.0020 g) was dissolved in 732 4, pH 4, 0.1 M NaOAc. The $^{18}$F was purified as described above, neutralized with glacial acetic acid and mixed with the Al solution. The peptide solution, 20 µL was then added and the solution was heated at 99° C. for 25 min. The crude product was then purified on a WATERS® HLB column. The [Al$^{18}$F] labeled peptide was in the 1:1 EtOH/H$_2$O column eluent. The reverse phase HPLC trace in 0.1% TFA buffers showed a clean single HPLC peak at the expected location for the labeled peptide (not shown).

Example 12

Synthesis and Labeling of IMP 461 and IMP 462 NOTA-Conjugated Peptides

The simplest possible NOTA ligand (protected for peptide synthesis) was prepared and incorporated into two peptides for pretargeting—IMP 461 and IMP 462.

Synthesis of Di-t-butyl-NOTA

NO2AtBu (0.501 g 1.4×10$^{-3}$ mol) was dissolved in 5 mL anhydrous acetonitrile. Benzyl-2-bromoacetate (0.222 mL, 1.4×10$^{-3}$ mol) was added to the solution followed by 0.387 g of anhydrous K$_2$CO$_3$. The reaction was allowed to stir at room temperature overnight. The reaction mixture was filtered and concentrated to obtain 0.605 g (86% yield) of the benzyl ester conjugate. The crude product was then dissolved in 50 mL of isopropanol, mixed with 0.2 g of 10% Pd/C (under Ar) and placed under 50 psi H$_2$ for 3 days. The product was then filtered and concentrated under vacuum to obtain 0.462 g of the desired product ESMS MH$^-$ 415.

Synthesis of IMP 461

The peptide was synthesized on Sieber amide resin with the amino acids and other agents added in the following order Aloc-D-Lys(Fmoc)-OH, Trt-HSG-OH, Aloc removal, Fmoc-D-Tyr(But)-OH, Aloc-D-Lys(Fmoc)-OH, Trt-HSG-OH, Aloc removal, Fmoc-D-Ala-OH, and Bis-t-butylNOTA-OH. The peptide was then cleaved and purified by HPLC to afford the product IMP 461 ESMS MH$^+$ 1294 (NOTA-D-Ala-D-Lys(HSG)-D-Tyr-D-Lys(HSG)-NH$_2$; SEQ ID NO:27).

Synthesis of IMP 462

The peptide was synthesized on Sieber amide resin with the amino acids and other agents added in the following order Aloc-D-Lys(Fmoc)-OH, Trt-HSG-OH, Aloc removal, Fmoc-D-Tyr(But)-OH, Aloc-D-Lys(Fmoc)-OH, Trt-HSG-OH, Aloc removal, Fmoc-D-Asp(But)-OH, and Bis-t-butyl-NOTA-OH. The peptide was then cleaved and purified by HPLC to afford the product IMP 462 ESMS MH$^+$1338 (NOTA-D-Asp-D-Lys(HSG)-D-Tyr-D-Lys(HSG)-NH$_2$; SEQ ID NO:28).

$^{18}$F Labeling of IMP 461 & IMP 462

The peptides were dissolved in pH 4.13, 0.5 M NaOAc to make a 0.05 M peptide solution, which was stored in the freezer until needed. The F-18 was received in 2 mL of water and trapped on a SEP-PAK® Light, WATERS® ACCELL™ Plus QMA Cartridge. The $^{18}$F was eluted from the column with 200 µL aliquots of 0.4 M KHCO$_3$. The bicarbonate was neutralized to ~pH 4 by the addition of 10 µL of glacial acetic acid to the vials before the addition of the activity. A 100 µL aliquot of the purified $^{18}$F solution was removed and mixed with 3 µL, 2 mM Al in pH 4, 0.1 M NaOAc. The peptide, 10 µL (0.05 M) was added and the solution was heated at ~100° C. for 15 min. The crude reaction mixture was diluted with 700 µL DI water and placed on an HLB column and after washing the $^{18}$F was eluted with 2×100 µL of 1:1 EtOH/H$_2$O to obtain the purified $^{18}$F-labeled peptide.

Example 13

Preparation and $^{18}$F Labeling of IMP 467

```
IMP 467
                                              (SEQ ID NO: 29)
C-NETA-succinyl-D-Lys(HSG)-D-Tyr-D-Lys(HSG)-NH₂
```

Tetra tert-butyl C-NETA-succinyl was produced. The tert-Butyl {4-[2-(Bis-(tert-butyoxycarbonyl)methyl-3-(4-nitrophenyl)propyl]-7-tert-butyoxycarbonyl[1,4,7]triazanonan-1-yl} was prepared as described in Chong et al. (J. Med. Chem. 2008, 51:118-125).

The peptide, IMP 467 C-NETA-succinyl-D-Lys(HSG)-D-Tyr-D-Lys(HSG)-NH$_2$ (SEQ ID NO:29) was made on Sieber Amide resin by adding the following amino acids to the resin in the order shown: Aloc-D-Lys(Fmoc)-OH, Trt-HSG-OH, the Aloc was cleaved Fmoc-D-Tyr(But)-OH, Aloc-D-Lys(Fmoc)-OH, Trt-HSG-OH, the Aloc was cleaved, tert-Butyl {4-[Bis-(tert-butoxycarbonylmethyl)amino)-3-(4-succinylamidophenyl)propyl]-7-tert-butoxycarbonylmethyl[1,4,7]triazanonan-1-yl}acetate. The peptide was then cleaved from the resin and purified by RP-HPLC to yield 6.3 mg of IMP 467. The crude peptide was purified by high performance liquid chromatography (HPLC) using a C18 column.

Radiolabeling

A 2 mM solution of IMP 467 was prepared in pH 4, 0.1 M NaOAc. The $^{18}$F, 139 mCi, was eluted through a WATERS® ACCELL™ Plus SEP-PAK® Light QMA cartridge and the $^{18}$F was eluted with 1 mL of 0.4 M KHCO$_3$. The labeled IMP 467 was purified by HLB RP-HPLC. The RP-HPLC showed two peaks eluting (not shown), which are believed to be diastereomers of Al$^{18}$F IMP 467. Supporting this hypothesis, there appeared to be some interconversion between the two HLB peaks when IMP 467 was incubated at 37° C. (not shown). In pretargeting techniques as discussed below, since the Al$^{18}$F-chelator complex is not part of the hapten site for antibody binding, the presence of diastereomers does not appear to affect targeting of the $^{18}$F-labeled peptide to diseased tissues.

Comparison of Yield of Radiolabeled Peptides

In an attempt to improve labeling yields while maintaining in vivo stability, 3 NOTA derivatives of pretargeting peptide were synthesized (IMP 460, IMP 461 and IMP 467). Of these, IMP 467 nearly doubled the labeling yields of the other peptides (Table 5). All of the labeling studies in Table 5 were performed with the same number of moles of peptide and aluminum. The results shown in Table 5 represent an exemplary labeling experiment with each peptide.

The $^{18}$F-labeling yield of IMP 467 was ~70% when only 40 nmol (~13-fold less than IMP 449) was used with 1.3 GBq (35 mCi) of $^{18}$F, indicating this ligand has improved binding properties for the Al$^{18}$F complex. By enhancing the kinetics of ligand binding, yields were substantially improved (average 65-75% yield), while using fewer moles of IMP 467 (40 nmol), relative to IMP 449 (520 nmol, 44% yield).

TABLE 5

Comparison of yields of different NOTA containing peptides

| Peptide | Yield |
|---|---|
| IMP 449 | 44% |
| IMP 460 | 5.8% |
| IMP 461 | 31% |
| IMP 467 | 87% |

Example 14

Pretargeted Biodistribution with $^{18}$F-Labeled IMP 467 in LS174T Tumor Bearing Nude Mice The $^{18}$F-labeled IMP 467 peptide, prepared in the same manner as described above, was diluted for injection into LS174T tumor bearing nude mice. Al$^{18}$F-IMP 467 was prepared and injected in nude mice that were necropsied 1.5 h later. Table 6 shows the biodistribution of $^{18}$F-labeled IMP 467 using a TF2 pretargeting protocol. The peptide alone cleared quickly from the blood and body, similar to IMP 449 (not shown). The low uptake in the bone compared to $^{18}$F or Al$^{18}$F illustrates the stability of the Al$^{18}$F chelate and its suitability for pretargeting (not shown). As with IMP 449, using the TF2 bispecific antibody and pretargeting the distribution of labeled IMP 467 was mainly limited to tumor and kidney, with very little distribution to bone or other normal tissues (Table 6). Imaging studies with $^{18}$F-labeled IMP 467 are reported below. The data indicate that AlF-18 IMP 467 was stable in-vivo and the peptide targeted the antibody on the tumor surface.

Example 15

Factors Affecting Yield and Stability of IMP 467 Labeling

Peptide Concentration

To examine the effect of varying peptide concentration on yield, the amount of binding of Al$^{18}$F to peptide was determined in a constant volume (63 µL) with a constant amount of Al$^{3+}$ (6 nmol) and $^{18}$F, but varying the amount of peptide added. The yield of labeled peptide IMP 467 decreased with a decreasing concentration of peptide as follows: 40 nmol peptide (82% yield); 30 nmol (79% yield); 20 nmol (75% yield); 10 nmol (49% yield). Thus, varying the amount of peptide between 20 and 40 nmol had little effect on yield with IMP 467. However, a decreased yield was observed starting at 10 nmol of peptide in the labeling mix.

Aluminum Concentration

When IMP 467 was labeled in the presence of increasing amounts of Al$^{3+}$ (0, 5, 10, 15, 20 µL of 2 mM Al in pH 4 acetate buffer and keeping the total volume constant), yields of 3.5%, 80%, 77%, 78% and 74%, respectively, were achieved. These results indicated that (a) non-specific binding of $^{18}$F to this peptide in the absence of Al$^{3+}$ is minimal, (b) 10 nmol of Al$^{3+}$ was sufficient to allow for maximum $^{18}$F-binding, and (c) higher amounts of Al$^{3+}$ did not reduce binding substantially, indicating that there was sufficient chelation capacity at this peptide concentration.

Kinetics of Al$^{18}$F IMP 467 Radiolabeling

Kinetic studies showed that binding was complete within 5 min at 107° C. (5 min, 68%; 10 min, 61%; 15 min, 71%; and 30 min, 75%) with only moderate increases in isolated yield with reaction times as long as 30 min.

A radiolabeling reaction of IMP 467 performed at 50° C. showed that no binding was achieved at the lower temperature.

Effect of pH

The optimal pH for labeling was between 4.3 and 5.5. Yield ranged from 54% at pH 2.88; 70-77% at pH 3.99; 70% at pH 5; 41% at pH 6 to 3% at pH 7.3. The process could be expedited by eluting the $^{18}$F from the anion exchange column with nitrate or chloride ion instead of carbonate ion, which eliminates the need for adjusting the eluent to pH 4 with glacial acetic acid before mixing with the AlCl$_3$.

TABLE 6

TF2 Pretargeted Biodistribution in LS174T Tumor Bearing Nude Mice:

| Tissue | n | Weight | STD WT | % ID/g | STD % ID/g | % ID/org | STD % ID/org | T/NT | STD T/NT |
|---|---|---|---|---|---|---|---|---|---|
| Tumor | 6 | 0.741 | 0.522 | 3.415 | 1.265 | 2.742 | 2.112 | 1.0 | 0.0 |
| Liver | 6 | 1.510 | 0.475 | 0.175 | 0.086 | 0.247 | 0.087 | 22.6 | 12.9 |
| Spleen | 6 | 0.131 | 0.075 | 0.326 | 0.261 | 0.036 | 0.020 | 16.3 | 13.3 |
| Kidney | 6 | 0.160 | 0.027 | 3.098 | 0.647 | 0.484 | 0.076 | 1.1 | 0.3 |
| Lung | 6 | 0.178 | 0.032 | 0.204 | 0.059 | 0.035 | 0.011 | 17.0 | 5.0 |
| Blood | 6 | 0.207 | 0.006 | 0.153 | 0.100 | 0.252 | 0.145 | 28.2 | 13.8 |
| Stomach | 6 | 0.443 | 0.089 | 0.186 | 0.148 | 0.079 | 0.053 | 23.3 | 9.4 |
| Small Int. | 6 | 1.086 | 0.121 | 0.338 | 0.125 | 0.359 | 0.117 | 10.5 | 2.9 |
| Large Int. | 6 | 0.804 | 0.116 | 0.115 | 0.047 | 0.093 | 0.045 | 34.5 | 21.1 |
| Scapula | 6 | 0.154 | 0.040 | 0.123 | 0.020 | 0.019 | 0.005 | 28.0 | 10.9 |
| Spine | 6 | 0.199 | 0.022 | 0.503 | 0.372 | 0.101 | 0.082 | 9.4 | 6.5 |
| Muscle | 6 | 0.088 | 0.021 | 0.200 | 0.237 | 0.014 | 0.014 | 56.3 | 64.3 |
| Brain | 6 | 0.329 | 0.049 | 0.013 | 0.002 | 0.004 | 0.000 | 260.4 | 104.0 |

High-Dose Radiolabeling of IMP 467

Five microliters of 2 mM $Al^{3+}$ stock solution were mixed with 50 μL of $^{18}$F 1.3 GBq (35 mCi) followed by the addition of 20 μL of 2 mM IMP 467 in 0.1 mM, pH 4.1 acetate buffer. The reaction solution was heated to 104° C. for 15 min and then purified on an HLB column (~10 min) as described above, isolating 0.68 GBq (18.4 mCi) of the purified peptide in 69% radiochemical yield with a specific activity of 17 GBq/μmol (460 Ci/mmol). The reaction time was 15 min and the purification time was 12 min. The reaction was started 10 min after the 1.3 GBq (35 mCi) $^{18}$F was purified, so the total time from the isolation of the $^{18}$F to the purified final product was 37 min with a 52% yield without correcting for decay.

Human Serum Stability Test

An aliquot of the HLB purified peptide (~30 μL) was diluted with 200 μL human serum (previously frozen) and placed in the 37° C. HPLC sample chamber. Aliquots were removed at various time points and analyzed by HPLC. The HPLC analysis showed very high stability of the $^{18}$F-labeled peptides in serum at 37° C. for at least five hours (not shown). There was no detectable breakdown of the $^{18}$F-labeled peptide after a five hour incubation in serum (not shown).

The IMP 461 and IMP 462 ligands have two carboxyl groups available to bind the aluminum whereas the NOTA ligand in IMP 467 had four carboxyl groups. The serum stability study showed that the complexes with IMP 467 were stable in serum under conditions replicating in vivo use. Further, the in vivo biodistribution studies with labeled IMP 467 show that the $^{18}$F-Al labeled peptide is stable under actual in vivo conditions.

Peptides can be labeled with $^{18}$F rapidly (30 min) and in high yield by forming $Al^{18}F$ complexes that can be bound to a NOTA ligand on a peptide and at a specific activity of at least 17 GBq/μmol, without requiring HPLC purification. The $Al^{18}F$ NOTA-peptides are stable in serum and in vivo. Modifications of the NOTA ligand can lead to improvements in yield and specific activity, while still maintaining the desired in vivo stability of the $Al^{18}F$-NOTA complex, and being attached to a hydrophilic linker aids in the renal clearance of the peptide. Further, this method avoids the dry-down step commonly used to label peptides with $^{18}$F. As shown in the following Examples, this new $^{18}$F-labeling method is applicable to labeling of a broad spectrum of targeting peptides.

Optimized Labeling of $Al^{18}F$ IMP 467

Optimized conditions for $^{18}$F labeling of IMP 467 were identified. These consisted of eluting $^{18}$F-fluoride with commercial sterile saline (pH 5-7), mixing with 20 nmol of $AlCl_3$ and 40 nmol IMP 467 in pH 4 acetate buffer in a total volume of 100 μL, heating to 102° C. for 15 min, and performing SPE separation. High-yield (85%) and high specific activity (115 GBq/μmol) were obtained with IMP 467 in a single step, 30-min procedure after a simple solid-phase extraction (SPE) separation without the need for HPLC purification. $^{18}$F-IMP 467 was stable in PBS or human serum, with 2% loss of $^{18}$F$^-$ after incubation in either medium for 6 h at 37° C.

Concentration and Purification of $^{18}$F$^-$

Radiochemical-grade $^{18}$F$^-$ needs to be purified and concentrated before use. We examined 4 different SPE purification procedures to process the $^{18}$F$^-$ prior to its use. Most of the radiolabeling procedures were performed using $^{18}$F$^-$ prepared by a conventional process. The $^{18}$F$^-$ in 2 mL of water was loaded onto a SEP-PAK® Light, Waters Accell™ QMA Plus Cartridge that was pre-washed with 10 mL of 0.4M $KHCO_3$, followed by 10 mL water. After loading the $^{18}$F$^-$ onto the cartridge, it was washed with 5 mL water to remove any dissolved metal and radiometal impurities. The isotope was then eluted with ~1 mL of 0.4M $KHCO_3$ in several fractions to isolate the fraction with the highest concentration of activity. The eluted fractions were neutralized with 5 μL of glacial acetic acid per 100 μL of solution to adjust the eluent to pH 4-5.

In the second process, the QMA cartridge was washed with 10 mL pH 8.4, 0.5 M NaOAc followed by 10 mL DI $H_2O$. $^{18}$F$^-$ was loaded onto the column as described above and eluted with 1 mL, pH 6, 0.05 M $KNO_3$ in 200-μL fractions with 60-70% of the activity in one of the fractions. No pH adjustment of this solution was needed.

In the third process, the QMA cartridge was washed with 10 mL pH 8.4, 0.5 M NaOAc followed by 10 mL DI $H_2O$. The $^{18}$F$^-$ was loaded onto the column as described above and eluted with 1 mL, pH 5-7, 0.154 M commercial normal saline in 200-μL fractions with 80% of the activity in one of the fractions. No pH adjustment of this solution was needed.

Finally, we devised a method to prepare a more concentrated and high-activity $^{18}$F$^-$ solution, using tandem ion exchange. Briefly, Tygon tubing (1.27 cm long, 0.64 cm OD) was inserted into a TRICORN™ 5/20 column and filled with ~200 μL of AG 1-X8 resin, 100-200 mesh. The resin was washed with 6 mL 0.4 M $K_2CO_3$ followed by 6 mL $H_2O$. A SEP-PAK® light Waters ACCELL™ Plus CM cartridge was washed with DI $H_2O$. Using a syringe pump, the crude $^{18}$F$^-$ that was received in 5-mL syringe in 2 mL DI $H_2O$ flowed slowly through the CM cartridge and the TRICORN™ column over ~5 min followed by a 6 mL wash with DI $H_2O$ through both ion-binding columns. Finally, 0.4 M $K_2CO_3$ was pushed through only the TRICORN™ column in 50-μL fractions. Typically, 40 to 60% of the eluted activity was in one 50-μL fraction. The fractions were collected in 2.0 mL free-standing screw-cap microcentrifuge tubes containing 5 μL glacial acetic acid to neutralize the carbonate solution. The elution vial with the most activity was then used as the reaction vial.

Example 16

Synthesis and Labeling of IMP 470

IMP 470
(SEQ ID NO: 30)
L-NETA-succinyl-D-Lys(HSG)-D-Tyr-D-Lys(HSG)-NH₂

The peptide, IMP 470 was made on Sieber Amide resin by adding the following amino acids to the resin in the order shown: Aloc-D-Lys(Fmoc)-OH, Trt-HSG-OH, the Aloc was cleaved, Fmoc-D-Tyr(But)-OH, Aloc-D-Lys(Fmoc)-OH, Trt-HSG-OH. The free amine obtained after the removal of Aloc was reacted with succinic anhydride, to generate a carboxylic acid group at the N-terminus, which is activated using DIC in DMF and subsequently coupled with tert-butyl protected L-NETA. The peptide was then cleaved from the resin and purified by RP-HPLC to yield 16.4 mg of IMP 470. A product with molecular mass 1037.15 corresponding to the peptide without L-NETA and with retention time 9.001 min was also obtained.

For $^{18}$F labeling, to 3 μL 2 mM $AlCl_3$ solution was added 40 μL F-18 solution [1.736 mCi of $^{18}$F] followed by 20 μL (40 nmol) 2 mM IMP 470 solution and heated to 101° C. for 15 minutes. Reverse Phase HPLC analysis showed two radiolabeled peptide peaks at 26.10% (RT 8.90 min) and 47.29% (RT 9.30 min) and 26.61% of the activity eluted at the void volume of the column (2.70 min) (not shown).

The crude labeled peptide was purified by HLB column chromatography, eluting with 1:1 EtOH/H$_2$O to collect labeled peptide. The 790 µCi collected represents a recovery of 65.83% of labeled peptide.

Sixty µL of the HLB column purified $^{18}$F-labeled peptide were mixed with 100 µL human serum and the sample was maintained at 37° C. during the entire RP-HPLC analysis. The $^{18}$F-labeled IMP 470 was stable in serum for at least 4 hours (not shown).

Example 17

Labeling by Addition of $^{18}$F to a Peptide Pre-Incubated with Aluminum

An HSG containing peptide (IMP 465, NOTA-D-Ala-D-Lys(HSG)-D-Tyr-D-Lys(HSG)-NH$_2$) (SEQ ID NO:31) linked to macrocyclic NOTA complexed with aluminum, was successfully labeled with F-18. $^{18}$F incorporation using 40 nmol of IMP 465 was 13.20%. An intermediate peptide, IMP 461, was made as described above. Then 25.7 mg of IMP 461 was dissolved in 2 mL DI water to which was added 10.2 mg AlCl$_3$.6H$_2$O and the resultant solution heated to 100° C. for 1 h. The crude reaction mixture was purified by RP-HPLC to yield 19.6 mg of IMP 465.

For $^{18}$F labeling, 50 µL $^{18}$F solution [0.702 mCi of $^{18}$F] and 20 µL (40 nmol) 2 mM IMP 465 solution (0.1 M NaOAc, pH 4.18) was heated to 101° C. for 17 minutes. Reverse Phase HPLC analysis showed 15.38% (RT about 8.60 min) of the activity was attached to the peptide and 84.62% of the activity eluted at the void volume of the column (2.60 min).

In a separate experiment, the percent yield of $^{18}$F-labeled peptide could be improved by varying the amount of peptide added. The percent yield observed for IMP 465 was 0.27% at 10 nmol peptide, 1.8% at 20 nmol of peptide and 49% at 40 nmol of peptide.

IMP 467 showed higher yield than IMP 461 when peptide was pre-incubated with aluminum before exposure to $^{18}$F. IMP 467 was incubated with aluminum at room temperature and then frozen and lyophilized. The amount of aluminum added for the pre-incubation was varied.

TABLE 7

Labeling of IMP 467 Pre-Incubated with Aluminum Before $^{18}$F is Added

| IMP 467 + Al Premixed, Frozen and Lyophilized | Isolated Labeling Yield |
|---|---|
| 40 nmol IMP 467 + 10 nmol Al Premix | 82% |
| 40 nmol IMP 467 + 20 nmol Al Premix | 64% |
| 40 nmol IMP 467 + 30 nmol Al Premix | 74% |
| 40 nmol IMP 467 + 6 nmol Al Normal Labeling (Mix Al + $^{18}$F first) | 77% |

The yields were comparable to those obtained when IMP 467 is labeled by addition of an Al$^{18}$F complex. Thus, $^{18}$F labeling by addition of $^{18}$F to a peptide with aluminum already bound to the chelating moiety is a feasible alternative approach to pre-incubating the metal with $^{18}$F prior to addition to the chelating moiety.

Example 18

Synthesis and Labeling of IMP 468 Bombesin Peptide

The $^{18}$F labeled targeting moieties are not limited to antibodies or antibody fragments, but rather can include any molecule that binds specifically or selectively to a cellular target that is associated with or diagnostic of a disease state or other condition that may be imaged by $^{18}$F PET. Bombesin is a 14 amino acid peptide that is homologous to neuromedin B and gastrin releasing peptide, as well as a tumor marker for cancers such as lung and gastric cancer and neuroblastoma. IMP 468 (NOTA-NH—(CH$_2$)$_7$CO-Gln-Trp-Val-Trp-Ala-Val-Gly-His-Leu-Met-NH$_2$; SEQ ID NO:32) was synthesized as a bombesin analogue and labeled with $^{18}$F to target the gastrin-releasing peptide receptor.

The peptide was synthesized by Fmoc based solid phase peptide synthesis on Sieber amide resin, using a variation of a synthetic scheme reported in the literature (Prasanphanich et al., 2007, PNAS USA 104:12463-467). The synthesis was different in that a bis-t-butyl NOTA ligand was add to the peptide during peptide synthesis on the resin.

IMP 468 (0.0139 g, 1.02×10$^{-5}$ mol) was dissolved in 203 µL of 0.5 M pH 4.13 NaOAc buffer. The peptide dissolved but formed a gel on standing so the peptide gel was diluted with 609 µL of 0.5 M pH 4.13 NaOAc buffer and 406 µL of ethanol to produce an 8.35×10$^{-3}$ M solution of the peptide. The $^{18}$F was purified on a QMA cartridge and eluted with 0.4 M KHCO$_3$ in 200 µL fractions, neutralized with 10 µL of glacial acetic acid. The purified $^{18}$F, 40 µL, 1.13 mCi was mixed with 3 µL of 2 mM AlCl$_3$ in pH 4, 0.1 M NaOAc buffer. IMP 468 (59.2 µL, 4.94×10$^{-7}$ mol) was added to the Al$^{18}$F solution and placed in a 108° C. heating block for 15 min. The crude product was purified on an HLB column, eluted with 2×200 µL of 1:1 EtOH/H$_2$O to obtain the purified $^{18}$F-labeled peptide in 34% yield.

Example 19

Imaging of Tumors using $^{18}$F Labeled Bombesin

A NOTA-conjugated bombesin derivative (IMP 468) was prepared as described above. We began testing its ability to block radiolabeled bombesin from binding to PC-3 cells as was done by Prasanphanich et al. (PNAS 104:12462-12467, 2007). Our initial experiment was to determine if IMP 468 could specifically block bombesin from binding to PC-3 cells. We used IMP 333 as a non-specific control. In this experiment, 3×10$^6$ PC-3 cells were exposed to a constant amount (~50,000 cpms) of $^{125}$I-Bombesin (Perkin-Elmer) to which increasing amounts of either IMP 468 or IMP 333 was added. A range of 56 to 0.44 nM was used as our inhibitory concentrations.

The results showed that we could block the binding of $^{125}$I-BBN with IMP 468 but not with the control peptide (IMP 333) (not shown), thus demonstrating the specificity of IMP 468. Prasanphanich indicated an IC$_{50}$ for their peptide at 3.2 nM, which is approximately 7-fold lower than what we found with IMP 468 (21.5 nM).

This experiment was repeated using a commercially available BBN peptide. We increased the amount of inhibitory peptide from 250 to 2 nM to block the $^{125}$I-BBN from binding to PC-3 cells. We observed very similar IC$_{50}$-values for IMP 468 and the BBN positive control with an IC$_{50}$-value higher (35.9 nM) than what was reported previously (3.2 nM) but close to what the BBN control achieved (24.4 nM).

To examine in vivo targeting, the distribution of Al$^{18}$F IMP 468 was examined in scPC3 prostate cancer xenograft bearing nude male mice; alone vs. blocked with bombesin. For radiolabeling, aluminum chloride (10 µL, 2 mM), 51.9 mCi of $^{18}$F (from QMA cartridge), acetic acid, and 60 µL of IMP 468 (8.45 mM in ethanol/NaOAc) were heated at 100° C. for 15 min. The reaction mixture was purified on reverse phase HPLC. Fractions 40 and 41 (3.56, 1.91 mCi) were pooled and applied to HLB column for solvent exchange. The product was eluted in 800 μL (3.98 mCi) and 910 μCi remained on the column. ITLC developed in saturated NaCl showed 0.1% unbound activity.

Figure 3:
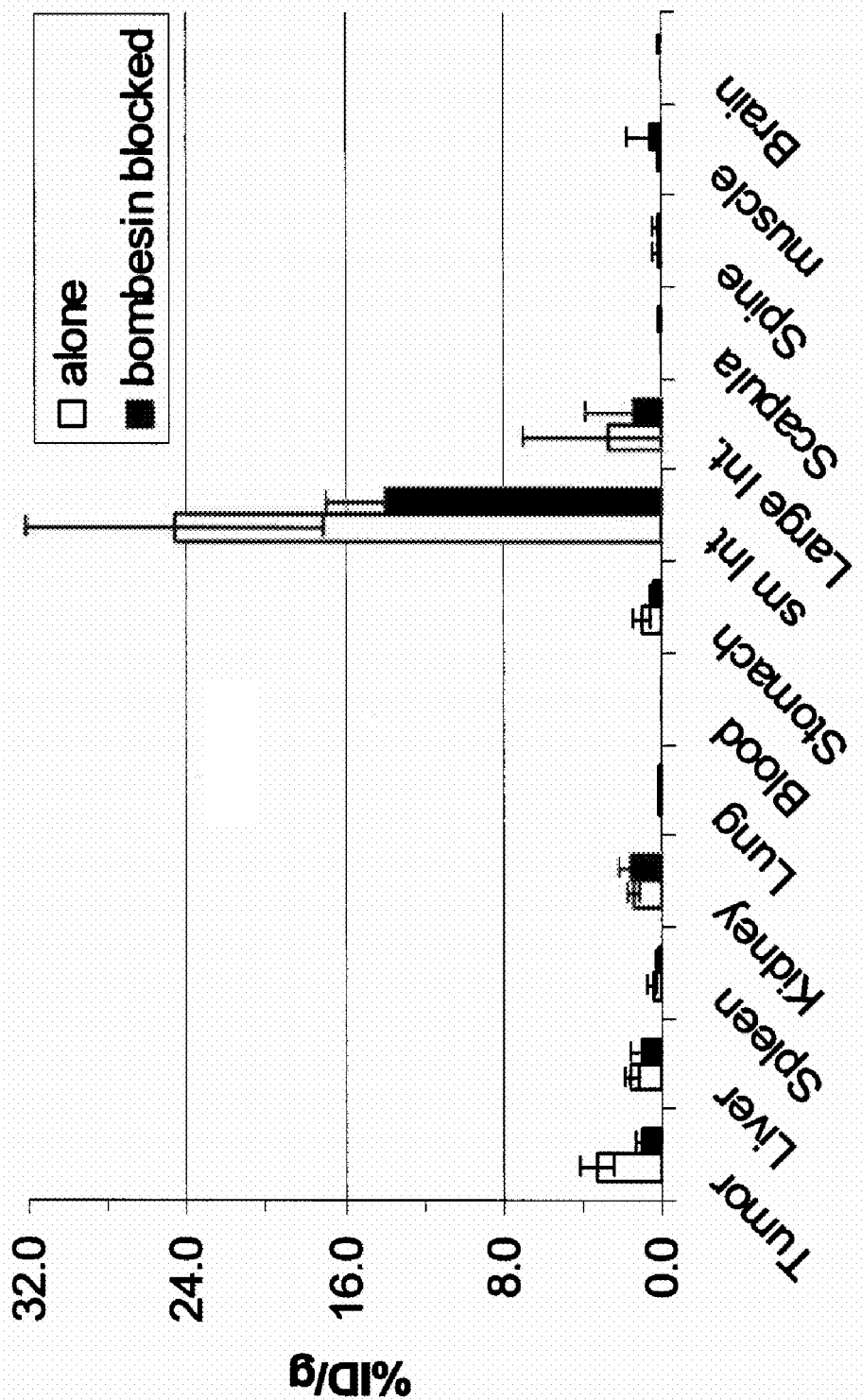
FIG. 3. In vivo tissue distribution with $^{18}$F-labeled IMP 468 bombesin analogue.

A group of six tumor-bearing mice were injected with [Al$^{18}$F] IMP 468 (167 μCi, ~9×10$^{-10}$ mol) and necropsied 1.5 h later. Another group of six mice were injected iv with 100 μg (6.2×10$^{-8}$ mol) of bombesin 18 min before administering [Al$^{18}$F] IMP 468. The second group was also necropsied 1.5 h post injection. The data shows specific targeting of the tumor with [Al$^{18}$F] IMP 468 (FIG. 3). Tumor uptake of the peptide is reduced when bombesin was given 18 min before the [Al$^{18}$F] IMP 468 (FIG. 3). Biodistribution data indicates in vivo stability of [Al$^{18}$F] IMP 468 for at least 1.5 h (not shown).

Larger tumors showed higher uptake of [Al$^{18}$F] IMP 468, possibly due to higher receptor expression in larger tumors (not shown). The biodistribution data showed [Al$^{18}$F] IMP 468 tumor targeting that was in the same range as reported for the same peptide labeled with $^{68}$Ga by Prasanphanich et al. (not shown). The results demonstrate that the $^{18}$F peptide labeling method can be used in vivo to target receptors that are upregulated in tumors, using targeting molecules besides antibodies. In this case, the IMP 468 targeting took advantage of a naturally occurring ligand-receptor interaction. The tumor targeting was significant with a P value of P=0.0013. Many such ligand-receptor pairs are known and any such targeting interaction may form the basis for $^{18}$F-imaging, using the methods described herein Example 20

Synthesis and Labeling of Somatostatin Analog IMP 466

Somatostatin is another non-antibody targeting peptide that is of use for imaging the distribution of somatostatin receptor protein. $^{123}$I-labeled octreotide, a somatostatin analog, has been used for imaging of somatostatin receptor expressing tumors (e.g., Kvols et al., 1993, Radiology 187:129-33; Leitha et al., 1993, J Nucl Med 34:1397-1402). However, $^{123}$I has not been of extensive use for imaging because of its expense, short physical half-life and the difficulty of preparing the radiolabeled compounds. The $^{18}$F-labeling methods described herein are preferred for imaging of somatostatin receptor expressing tumors.

```
                                              (SEQ ID NO: 33)
IMP 466
NOTA-D-Phe-Cys-Phe-D-Trp-Lys-Thr-Cys-Throl
```

A NOTA-conjugated derivative of the somatostatin analog octreotide (IMP 466) was made by standard Fmoc based solid phase peptide synthesis to produce a linear peptide. The C-terminal Throl residue is threoninol. The peptide was cyclized by treatment with DMSO overnight. The peptide, 0.0073 g, 5.59×10$^{-6}$ mol was dissolved in 111.9 μL of 0.5 M pH 4 NaOAc buffer to make a 0.05 M solution of IMP 466. The solution formed a gel over time so it was diluted to 0.0125 M by the addition of more 0.5 M NaOAc buffer.

$^{18}$F was purified and concentrated with a QMA cartridge to provide 200 μL of $^{18}$F in 0.4 M KHCO$_3$. The bicarbonate solution was neutralized with 10 μL of glacial acetic acid. A 40 μL aliquot of the neutralized $^{18}$F eluent was mixed with 3 μL of 2 mM AlCl$_3$, followed by the addition of 40 μL of 0.0125 M IMP 466 solution. The mixture was heated at 105° C. for 17 min. The reaction was then purified on a Waters 1 cc (30 mg) HLB column by loading the reaction solution onto the column and washing the unbound $^{18}$F away with water (3 mL) and then eluting the radiolabeled peptide with 2×200 μL 1:1 EtOH water. The yield of the radiolabeled peptide after HLB purification was 34.6%.

Effect of Ionic Strength

To lower the ionic strength of the reaction mixture escalating amounts of acetonitrile were added to the labeling mixture (final concentration: 0-80%). The yield of radiolabeled IMP 466 increased with increasing concentration of acetonitrile in the medium. The optimal radiolabeling yield (98%) was obtained in a final concentration of 80% acetonitrile, despite the increased volume (500 μL in 80% vs. 200 μL in 0% acetonitrile). In 0% acetonitrile the radiolabeling yield ranged from 36% to 55% in three experiments.

Example 21

Imaging of Neuroendocrine Tumors with an $^{18}$F- and $^{68}$Ga-Labeled IMP 466

Studies were performed to compare the PET images obtained using an $^{18}$F versus $^{68}$Ga-labeled somatostatin analogue peptide and direct targeting to somatostatin receptor expressing tumors.

Methods $^{18}$F labeling—IMP 466 was synthesized and $^{18}$F-labeled by a variation of the method described in the Example above. A QMA SEPPAK® light cartridge (Waters, Milford, Mass.) with 2-6 GBq $^{18}$F (BV Cyclotron VU, Amsterdam, The Netherlands) was washed with 3 mL metal-free water. $^{18}$F was eluted from the cartridge with 0.4 M KHCO$_3$ and fractions of 200 μL were collected. The pH of the fractions was adjusted to pH 4, with 10 μL metal-free glacial acid. Three μL of 2 mM AlCl$_3$ in 0.1 M sodium acetate buffer, pH 4 were added. Then, 10-50 μL IMP 466 (10 mg/mL) were added in 0.5 M sodium acetate, pH 4.1. The reaction mixture was incubated at 100° C. for 15 min unless stated otherwise. The radiolabeled peptide was purified on RP-HPLC. The $^{18}$F-IMP 466-containing fractions were collected and diluted two-fold with H$_2$O and purified on a 1-cc Oasis HLB cartridge (Waters, Milford, Mass.) to remove acetonitrile and TFA. In brief, the fraction was applied on the cartridge and the cartridge was washed with 3 mL H$_2$O. The radiolabeled peptide was then eluted with 2×200 μL 50% ethanol. For injection in mice, the peptide was diluted with 0.9% NaCl. A maximum specific activity of 45,000 GBq/mmol was obtained.

$^{68}$Ga labeling—IMP 466 was labeled with $^{68}$GaCl$_3$ eluted from a TiO$_2$-based 1,110 MBq $^{68}$Ge/$^{68}$Ga generator (Cyclotron Co. Ltd., Obninsk, Russia) using 0.1 M ultrapure HCl (J. T. Baker, Deventer, The Netherlands). IMP 466 was dissolved in 1.0 M HEPES buffer, pH 7.0. Four volumes of $^{68}$Ga eluate (120-240 MBq) were added and the mixture was heated at 95° C. for 20 min. Then 50 mM EDTA was added to a final concentration of 5 mM to complex the non-incorporated $^{68}$Ga$^{3+}$. The Ga-labeled IMP 466 was purified on an Oasis HLB cartridge and eluted with 50% ethanol.

Octanol-water partition coefficient (log P$_{oct/water}$)—To determine the lipophilicity of the radiolabeled peptides, approximately 50,000 dpm of the radiolabeled peptide was diluted in 0.5 mL phosphate-buffered saline (PBS). An equal volume of octanol was added to obtain a binary phase system. After vortexing the system for 2 min, the two layers were separated by centrifugation (100×g, 5 min). Three 100 μL samples were taken from each layer and radioactivity was measured in a well-type gamma counter (Wallac Wizard 3", Perkin-Elmer, Waltham, Mass.).

Stability—Ten µL of the $^{18}$F-labeled IMP 466 was incubated in 500 µL of freshly collected human serum and incubated for 4 h at 37° C. Acetonitrile was added and the mixture was vortexed followed by centrifugation at 1000×g for 5 min to precipitate serum proteins. The supernatant was analyzed on RP-HPLC as described above.

Cell culture—The AR42J rat pancreatic tumor cell line was cultured in Dulbecco's Modified Eagle's Medium (DMEM) medium (Gibco Life Technologies, Gaithersburg, Md., USA) supplemented with 4500 mg/L D-glucose, 10% (v/v) fetal calf serum, 2 mmol/L glutamine, 100 U/mL penicillin and 100 µg/mL streptomycin. Cells were cultured at 37° C. in a humidified atmosphere with 5% $CO_2$.

$IC_{50}$ determination—The apparent 50% inhibitory concentration ($IC_{50}$) for binding the somatostatin receptors on AR42J cells was determined in a competitive binding assay using $^{19}$F-IMP 466, $^{69}$Ga-IMP 466 or $^{115}$In-DTPA-octreotide to compete for the binding of $^{111}$In-DTPA-octreotide.

$^{19}$F-IMP 466 was formed by mixing an aluminium fluoride (AlF) solution (0.02 M $AlCl_3$ in 0.5 M NaAc, pH 4, with 0.1 M NaF in 0.5 M NaAc, pH 4) with IMP 466 and heating at 100° C. for 15 min. The reaction mixture was purified by RP-HPLC on a C-18 column as described above.

$^{69}$Ga-IMP 466 was prepared by dissolving gallium nitrate ($2.3 \times 10^{-8}$ mol) in 30 pit mixed with 20 µl IMP 466 (1 mg/mL) in 10 mM NaAc, pH 5.5, and heated at 90° C. for 15 min. Samples of the mixture were used without further purification.

$^{115}$In-DTPA-octreotide was made by mixing indium chloride ($1 \times 10^{-5}$ mol) with 10 µL DTPA-octreotide (1 mg/mL) in 50 mM NaAc, pH 5.5, and incubated at room temperature (RT) for 15 min. This sample was used without further purification. $^{111}$In-DTPA-octreotide (OCTREOSCAN®) was radiolabeled according to the manufacturer's protocol.

AR42J cells were grown to confluency in 12-well plates and washed twice with binding buffer (DMEM with 0.5% bovine serum albumin). After 10 min incubation at RT in binding buffer, $^{19}$F-IMP 466, $^{69}$Ga-IMP 466 or $^{115}$In-DTPA-octreotide was added at a final concentration ranging from 0.1-1000 nM, together with a trace amount (10,000 cpm) of $^{111}$In-DTPA-octreotide (radiochemical purity >95%). After incubation at RT for 3 h, the cells were washed twice with ice-cold PBS. Cells were scraped and cell-associated radioactivity was determined. Under these conditions, a limited extent of internalization may occur. We therefore describe the results of this competitive binding assay as "apparent $IC_{50}$" values rather than $IC_{50}$. The apparent $IC_{50}$ was defined as the peptide concentration at which 50% of binding without competitor was reached.

Biodistribution studies—Male nude BALB/c mice (6-8 weeks) were injected subcutaneously in the right flank with 0.2 mL AR42J cell suspension of $10^7$ cells/mL. Approximately two weeks after tumor cell inoculation when tumors were 5-8 mm in diameter, 370 kBq $^{18}$F or $^{68}$Ga-labeled IMP 466 was administered intravenously (n=5). Separate groups (n=5) were injected with a 1,000-fold molar excess of unlabeled IMP 466. One group of three mice was injected with unchelated [Al$^{18}$F]. All mice were killed by $CO_2/O_2$ asphyxiation 2 h post-injection (p.i.). Organs of interest were collected, weighed and counted in a gamma counter. The percentage of the injected dose per gram tissue (% ID/g) was calculated for each tissue. The animal experiments were approved by the local animal welfare committee and performed according to national regulations.

PET/CT imaging—Mice with s.c. AR42J tumors were injected intravenously with 10 MBq Al$^{18}$F-IMP 466 or $^{68}$Ga-IMP 466. One and two hours after the injection of peptide, mice were scanned on an Inveon animal PET/CT scanner (Siemens Preclinical Solutions, Knoxville, Tenn.) with an intrinsic spatial resolution of 1.5 mm (Visser et al, JNM, 2009). The animals were placed in a supine position in the scanner. PET emission scans were acquired over 15 minutes, followed by a CT scan for anatomical reference (spatial resolution 113 µm, 80 kV, 500 µA). Scans were reconstructed using Inveon Acquisition Workplace software version 1.2 (Siemens Preclinical Solutions, Knoxville, Tenn.) using an ordered set expectation maximization-3D/maximum a posteriori (OSEM3D/MAP) algorithm with the following parameters: matrix 256×256×159, pixel size 0.43×0.43×0.8 mm$^3$ and MAP prior of 0.5 mm.

Results

Effect of buffer—The effect of the buffer on the labeling efficiency of IMP 466 was investigated. IMP 466 was dissolved in sodium citrate buffer, sodium acetate buffer, 2-(N-morpholino)ethanesulfonic acid (MES) or 4-(2-hydroxyethyl)-1-piperazineethanesulfonic acid (HEPES) buffer at 10 mg/mL (7.7 mM). The molarity of all buffers was 1 M and the pH was 4.1. To 200 µg (153 nmol) of IMP 466 was added 100 µL Al—F-18 (pH 4) and incubated at 100° C. for 15 min. Radiolabeling yield and specific activity was determined with RP-HPLC. When using sodium acetate, MES or HEPES, radiolabeling yield was 49%, 44% and 46%, respectively. In the presence of sodium citrate, no labeling was observed (<1%). When the labeling reaction was carried out in sodium acetate buffer, the specific activity of the preparations was 10,000 GBq/mmol, whereas in MES and HEPES buffer a specific activity of 20,500 and 16,500 GBq/mmol was obtained, respectively.

Effect of $AlCl_3$ concentration—Three stock solutions of $AlCl_3$ in sodium acetate, pH 4.1 were prepared: 0.2, 2.0 and 20 mM. From these solutions, 3 µL was added to 200 µL, of $^{18}$F to form [Al$^{18}$F]. To these samples, 153 nmol of peptide was added and incubated for 15 min at 100° C. Radiolabeling yield was 49% after incubation at a final concentration of 6 nmol $AlCl_3$. Incubation with 0.6 nmol $AlCl_3$ and 60 nmol $AlCl_3$ resulted in a strong reduction of the radiolabeling yield: 10% and 6%, respectively.

Effect of amount of peptide—The effect of the amount of peptide on the labeling efficiency was investigated. IMP 466 was dissolved in sodium acetate buffer, pH 4.1 at a concentration of 7.7 mM (10 mg/mL) and 38, 153 or 363 nmol of IMP 466 was added to 200 µL [Al$^{18}$F] (581-603 MBq). The radiolabeling yield increased with increasing amounts of peptide. At 38 nmol, radiolabeling yield ranged from 4-8%, at 153 nmol, the yield had increased to 42-49% and at the highest concentration the radiolabeling yield was 48-52%.

Octanol-water partition coefficient—To determine the lipophilicity of the $^{18}$F and $^{68}$Ga-labeled IMP 466, the octanol-water partition coefficients were determined. The log $P_{octanol/water}$ value for the Al$^{18}$F-IMP 466 was −2.44±0.12 and that of $^{68}$Ga-IMP 466 was −3.79±0.07, indicating that the $^{18}$F-labeled IMP 466 was slightly less hydrophilic.

Stability—The $^{18}$F-labeled IMP 466 did not show release of $^{18}$F after incubation in human serum at 37° C. for 4 h, indicating excellent stability of the Al$^{18}$F—NOTA complex.

$IC_{50}$ determination—The apparent $IC_{50}$ of Al$^{19}$F-labeled IMP 466 was 3.6±0.6 nM, whereas that for $^{69}$Ga-labeled IMP 466 was 13±3 nM. The apparent $IC_{50}$ of the reference peptide, $^{115}$In-DTPA-octeotride (OCTREOSCAN®), was 6.3±0.9 nM.

Figure 4:
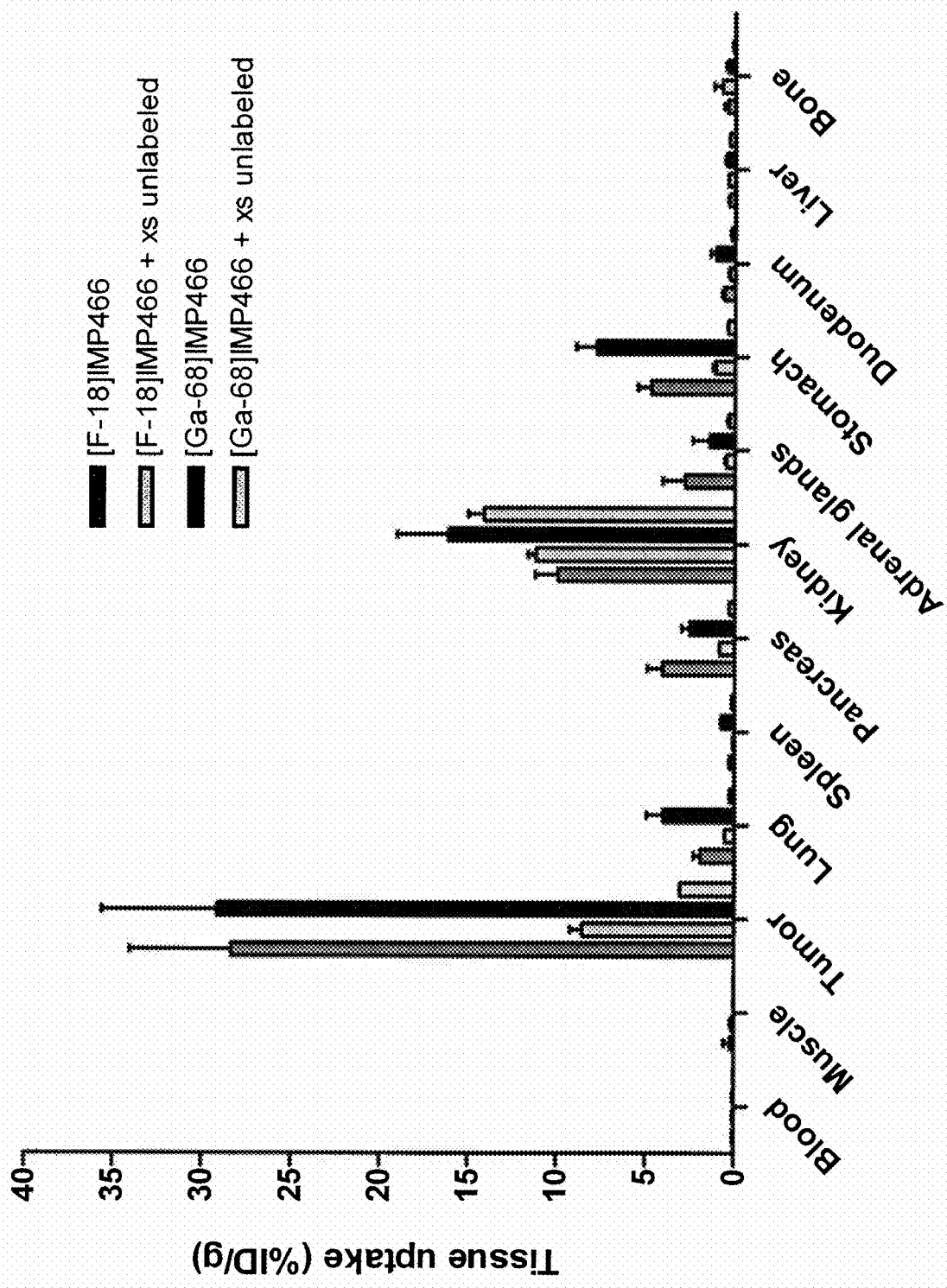
FIG. 4. Comparison of biodistribution of $^{18}$F-IMP 466 and $^{68}$Ga-IMP 466 at 2 h p.i. in AR42J tumor-bearing mice (n=5). As a control, mice in separate groups (n=5) received an excess of unlabeled octreotide to demonstrate receptor specificity.

Biodistribution studies—The biodistribution of both Al$^{18}$F-IMP 466 and $^{68}$Ga-IMP 466 was studied in nude BALB/c mice with s.c. AR42J tumors at 2 h p.i. (FIG. 4). Al$^{18}$F was included as a control. Tumor targeting of the $^{18}$F-IMP 466 was high with 28.3±5.7% ID/g accumulated at 2 h p.i. Uptake in the presence of an excess of unlabeled IMP 466 was 8.6±0.7% ID/g, indicating that tumor uptake was receptor-mediated. Blood levels were very low (0.10±0.07% ID/g, 2 h pi), resulting in a tumor-to-blood ratio of 299±88. Uptake in the organs was low, with specific uptake in receptor expressing organs such as adrenal glands, pancreas and stomach. Bone uptake of Al$^{18}$F-IMP 466 was negligible as compared to uptake of non-chelated Al$^{18}$F (0.33±0.07 vs. 36.9±5.0% ID/g at 2 h p.i., respectively), indicating good in vivo stability of the $^{18}$F-labeled NOTA-peptide.

The biodistribution of Al$^{18}$F-IMP 466 was compared to that of $^{68}$Ga-IMP 466 (FIG. 4). Tumor uptake of $^{68}$Ga-IMP 466 (29.2±0.5% ID/g, 2 h pi) was similar to that of Al$^{18}$F-IMP 466 (p<0.001). Lung uptake of $^{68}$Ga-IMP 466 was two-fold higher than that of $^{18}$F-IMP 466 (4.0±0.9% ID/g vs. 1.9±0.4% ID/g, respectively). In addition, kidney retention of $^{68}$Ga-IMP 466 was slightly higher than that of Al$^{18}$F-IMP 466 (16.2±2.86% ID/g vs. 9.96±1.27% ID/g, respectively).

Figure 5:
FIG. 5. Coronal slices of PET/CT scan of $^{18}$F-IMP 466 and $^{68}$Ga-IMP 466 at 2 h p.i. in mice with an s.c. AR42J tumor in the neck. Accumulation in tumor and kidneys is clearly visualized.
Figure 5:

Fused PET and CT scans are shown in FIG. 5. PET scans corroborated the biodistribution data. Both Al$^{18}$F-IMP 466 and $^{68}$Ga-IMP 466 showed high uptake in the tumor and retention in the kidneys. The activity in the kidneys was mainly localized in the renal cortex. Again, the Al$^{18}$F proved to be stably chelated by the NOTA chelator, since no bone uptake was observed.

FIG. 5 clearly shows that the distribution of an $^{18}$F-labeled analog of somatostatin (octreotide) mimics that of a $^{68}$Ga-labeled somatostatin analog. These results are significant, since $^{68}$Ga-labeled octreotide PET imaging in human subjects with neuroendocrine tumors has been shown to have a significantly higher detection rate compared with conventional somatostatin receptor scintigraphy and diagnostic CT, with a sensitivity of 97%, a specificity of 92% and an accuracy of 96% (e.g., Gabriel et al., 2007, J Nucl Med 48:508-18). PET imaging with $^{68}$Ga-labeled octreotide is reported to be superior to SPECT analysis with $^{111}$In-labeled octreotide and to be highly sensitive for detection of even small meningiomas (Henze et al., 2001, J Nucl Med 42:1053-56). Because of the higher energy of $^{68}$Ga compared with $^{18}$F, it is expected that $^{18}$F based PET imaging would show even better spatial resolution than $^{68}$Ga based PET imaging. This is illustrated in FIG. 5 by comparing the kidney images obtained with $^{18}$F-labeled IMP 466 (FIG. 5, left) vs. $^{68}$Ga-labeled IMP 466 (FIG. 5, right). The PET images obtained with $^{68}$Ga show more diffuse margins and lower resolution than the images obtained with $^{18}$F. These results demonstrate the superior images obtained with $^{18}$F-labeled targeting moieties prepared using the methods and compositions described herein and confirm the utility of the described $^{18}$F labeling techniques for non-antibody targeting peptides.

Example 22

Comparison of $^{68}$Ga and $^{18}$F PET Imaging using Pretargeting

We compared PET images obtained using $^{68}$Ga- or $^{18}$F-labeled peptides that were pretargeted with the bispecific TF2 antibody, prepared as described above. The half-lives of $^{68}$Ga ($t_{1/2}$=68 minutes) and $^{18}$F ($t_{1/2}$=110 minutes) match with the pharmacokinetics of the radiolabeled peptide, since its maximum accretion in the tumor is reached within hours. Moreover, $^{68}$Ga is readily available from $^{68}$Ge/$^{68}$Ga generators, whereas $^{18}$F is the most commonly used and widely available radionuclide in PET.

Methods

Mice with s.c. CEA-expressing LS174T tumors received TF2 (6.0 nmol; 0.94 mg) and 5 MBq $^{68}$Ga-labeled IMP 288 (0.25 nmol) or $^{18}$F-labeled IMP 449 (0.25 nmol) intravenously, with an interval of 16 hours between the injection of the bispecific antibody and the radiolabeled peptide. One or two hours after the injection of the radiolabeled peptide, PET/CT images were acquired and the biodistribution of the radiolabeled peptide was determined. Uptake in the LS174T tumor was compared with that in an s.c. CEA-negative SK-RC 52 tumor. Pretargeted immunoPET imaging was compared with $^{18}$F-FDG-PET imaging in mice with an s.c. LS174T tumor and contralaterally an inflamed thigh muscle.

(SEQ ID NO: 34)
IMT 288    DOTA-D-Tyr-D-Lys(HSG)-D-Glu-D-Lys(HSG)-NH$_2$

Pretargeting—The bispecific TF2 antibody was made by the DNL method, as described above. TF2 is a trivalent bispecific antibody comprising an HSG-binding Fab fragment from the h679 antibody and two CEA-binding Fab fragments from the hMN-14 antibody. The DOTA-conjugated, HSG-containing peptide IMP 288 was synthesized by peptide synthesis as described above. The IMP 449 peptide, synthesized as described above, contains a 1,4,7-triazacyclononane-1,4,7-triacetic acid (NOTA) chelating moiety to facilitate labeling with $^{18}$F. As a tracer for the antibody component, TF2 was labeled with $^{125}$I (Perkin Elmer, Waltham, Mass.) by the iodogen method (Fraker and Speck, 1978, Biochem Biophys Res Comm 80:849-57), to a specific activity of 58 MBq/nmol.

Labeling of IMP 288—IMP 288 was labeled with $^{111}$In (Covidien, Petten, The Netherlands) for biodistribution studies at a specific activity of 32 MBq/nmol under strict metal-free conditions. IMP 288 was labeled with $^{68}$Ga eluted from a TiO-based 1,110 MBq $^{68}$Ge/$^{68}$Ga generator (Cyclotron Co. Ltd., Obninsk Russia) using 0.1 M ultrapure HCl. Five 1 ml fractions were collected and the second fraction was used for labeling the peptide. One volume of 1.0 M HEPES buffer, pH 7.0 was added to 3.4 nmol IMP 288. Four volumes of $^{68}$Ga eluate (380 MBq) were added and the mixture was heated to 95° C. for 20 min. Then 50 mM EDTA was added to a final concentration of 5 mMM to complex the non-chelated $^{68}$Ga$^{3+}$. The $^{68}$Ga-labeled IMP 288 peptide was purified on a 1-mL Oasis HLB-cartridge (Waters, Milford, Mass.). After washing the cartridge with water, the peptide was eluted with 25% ethanol. The procedure to label IMP 288 with $^{68}$Ga was performed within 45 minutes, with the preparations being ready for in vivo use.

Labeling of IMP 449—IMP 449 was labeled with $^{18}$F as described above. 555-740 MBq $^{18}$F (B.V. Cyclotron VU, Amsterdam, The Netherlands) was eluted from a QMA cartridge with 0.4 M KHCO$_3$. The Al$^{18}$F activity was added to a vial containing the peptide (230 μg) and ascorbic acid (10 mg). The mixture was incubated at 100° C. for 15 min. The reaction mixture was purified by RP-HPLC. After adding one volume of water, the peptide was purified on a 1-mL Oasis HLB cartridge. After washing with water, the radiolabeled peptide was eluted with 50% ethanol. $^{18}$F-IMP 449 was prepared within 60 minutes, with the preparations being ready for in vivo use.

Radiochemical purity of $^{125}$I-TF2, $^{111}$In- and $^{68}$Ga-IMP 288 and Al$^{18}$F-IMP 449 preparations used in the studies always exceeded 95%.

Animal experiments—Experiments were performed in male nude BALB/c mice (6-8 weeks old), weighing 20-25 grams. Mice received a subcutaneous injection with 0.2 mL of a suspension of $1 \times 10^6$ LS174T-cells, a CEA-expressing human colon carcinoma cell line (American Type Culture Collection, Rockville, Md., USA). Studies were initiated when the tumors reached a size of about 0.1-0.3 g (10-14 days after tumor inoculation).

The interval between TF2 and IMP 288 injection was 16 hours, as this period was sufficient to clear unbound TF2 from the circulation. In some studies $^{125}$I-TF2, (0.4 MBq) was co-injected with unlabeled TF2. IMP 288 was labeled with either $^{111}$In or $^{68}$Ga. IMP 449 was labeled with $^{18}$F. Mice received TF2 and IMP 288 intravenously (0.2 mL). One hour after the injection of $^{68}$Ga-labeled peptide, and two hours after injection of $^{18}$F-IMP 449, mice were euthanized by $CO_2/O_2$, and blood was obtained by cardiac puncture and tissues were dissected.

PET images were acquired with an Inveon animal PET/CT scanner (Siemens Preclinical Solutions, Knoxville, Tenn.). PET emission scans were acquired for 15 minutes, preceded by CT scans for anatomical reference (spatial resolution 113 µm, 80 kV, 500 µA, exposure time 300 msec).

After imaging, tumor and organs of interest were dissected, weighed and counted in a gamma counter with appropriate energy windows for $^{125}$I, $^{111}$In, $^{68}$Ga or $^{18}$F. The percentage-injected dose per gram tissue (% ID/g) was calculated.

Results

Within 1 hour, pretargeted immunoPET resulted in high and specific targeting of $^{68}$Ga-IMP 288 in the tumor (10.7±3.6% ID/g), with very low uptake in the normal tissues (e.g., tumor/blood 69.9±32.3), in a CEA-negative tumor (0.35±0.35% ID/g), and inflamed muscle (0.72±0.20% ID/g). Tumors that were not pretargeted with TF2 also had low $^{68}$Ga-IMP 288 uptake (0.20±0.03% ID/g). [$^{18}$F]FDG accreted efficiently in the tumor (7.42±0.20% ID/g), but also in the inflamed muscle (4.07±1.13% ID/g) and a number of normal tissues, and thus pretargeted $^{68}$Ga-IMP 288 provided better specificity and sensitivity. The corresponding PET/CT images of mice that received $^{68}$Ga-IMP 288 or $^{18}$F-labeled IMP 449 following pretargeting with TF2 clearly showed the efficient targeting of the radiolabeled peptide in the subcutaneous LS174T tumor, while the inflamed muscle was not visualized. In contrast, with [$^{18}$F]FDG the tumor as well as the inflammation was clearly delineated.

Dose optimization—The effect of the TF2 bsMAb dose on tumor targeting of a fixed 0.01 nmol (15 ng) dose of IMP 288 was determined. Groups of five mice were injected intravenously with 0.10, 0.25, 0.50 or 1.0 nmol TF2 (16, 40, 80 or 160 µg respectively), labeled with a trace amount of $^{125}$I (0.4 MBq). One hour after injection of $^{111}$In-IMP 288 (0.01 nmol, 0.4 MBq), the biodistribution of the radiolabels was determined.

TF2 cleared rapidly from the blood and the normal tissues. Eighteen hours after injection the blood concentration was less than 0.45% ID/g at all TF2 doses tested. Targeting of TF2 in the tumor was 3.5% ID/g at 2 h p.i. and independent of TF2 dose (data not shown). At all TF2 doses $^{111}$In-IMP 288 accumulated effectively in the tumor (not shown). At higher TF2 doses enhanced uptake of $^{111}$In-IMP 288 in the tumor was observed: at 1.0 nmol TF2 dose maximum targeting of IMP 288 was reached (26.2±3.8% ID/g). Thus at the 0.01 nmol peptide dose highest tumor targeting and tumor-to-blood ratios were reached at the highest TF2 dose of 1.0 nmol (TF2:IMP 288 molar ratio=100:1). Among the normal tissues, the kidneys had the highest uptake of $^{111}$In IMP 288 (1.75±0.27% ID/g) and uptake in the kidneys was not affected by the TF2 dose (not shown). All other normal tissues had very low uptake, resulting in extremely high tumor-to-nontumor ratios, exceeding 50:1 at all TF2 doses tested (not shown).

For PET imaging using $^{68}$Ga-labeled IMP 288, a higher peptide dose is required, because a minimum activity of 5-10 MBq $^{68}$Ga needs to be injected per mouse if PET imaging is performed 1 h after injection. The specific activity of the $^{68}$Ga-IMP 288 preparations was 50-125 MBq/nmol at the time of injection. Therefore, for PET imaging at least 0.1-0.25 nmol of IMP 288 had to be administered. The same TF2:IMP 288 molar ratios were tested at 0.1 nmol IMP 288 dose. LS174T tumors were pretargeted by injecting 1.0, 2.5, 5.0 or 10.0 nmol TF2 (160, 400, 800 or 1600 µs). In contrast to the results at the lower peptide dose, $^{111}$In-IMP 288 uptake in the tumor was not affected by the TF2 doses (15% ID/g at all doses tested, data not shown). TF2 targeting in the tumor in terms of % ID/g decreased at higher doses (3.21±0.61% ID/g versus 1.16±0.27% ID/g at an injected dose of 1.0 nmol and 10.0 nmol, respectively) (data not shown). Kidney uptake was also independent of the bsMAb dose (2% ID/g). Based on these data we selected a bsMAb dose of 6.0 nmol for targeting 0.1-0.25 nmol of IMP 288 to the tumor.

PET imaging—To demonstrate the effectiveness of pretargeted immunoPET imaging with TF2 and $^{68}$Ga-IMP 288 to image CEA-expressing tumors, subcutaneous tumors were induced in five mice. In the right flank an s.c. LS174T tumor was induced, while at the same time in the same mice $1 \times 10^6$ SK-RC 52 cells were inoculated in the left flank to induce a CEA-negative tumor. Fourteen days later, when tumors had a size of 0.1-0.2 g, the mice were pretargeted with 6.0 nmol $^{125}$I-TF2 intravenously. After 16 hours the mice received 5 MBq $^{68}$Ga-IMP 288 (0.25 nmol, specific activity of 20 MBq/nmol). A separate group of three mice received the same amount of $^{68}$Ga-IMP 288 alone, without pretargeting with TF2. PET/CT scans of the mice were acquired 1 h after injection of the $^{68}$Ga-IMP 288.

Figure 6:
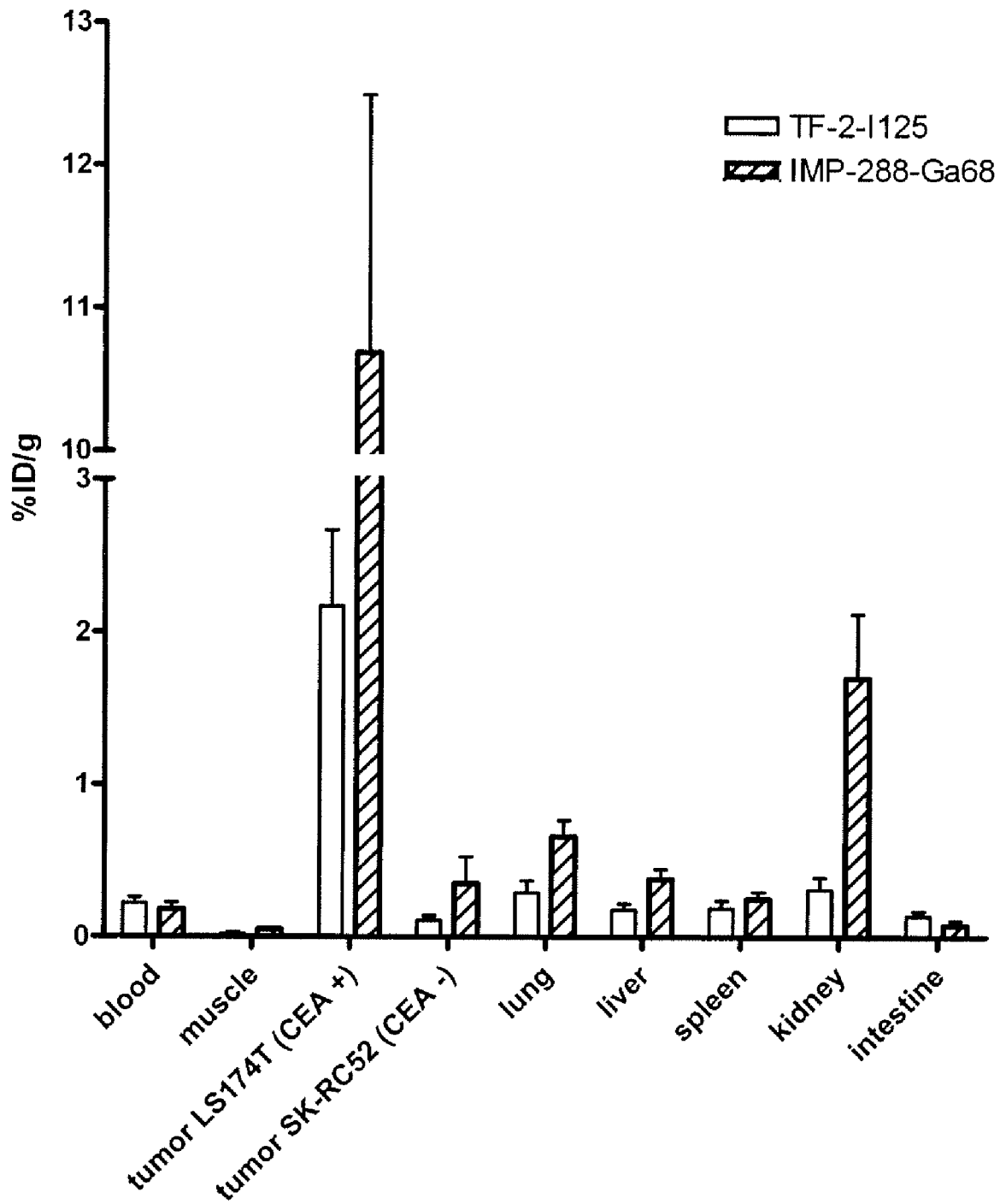
FIG. 6. Biodistribution of 6.0 nmol $^{125}$I-TF2 (0.37 MBq) and 0.25 nmol $^{68}$Ga-IMP 288 (5 MBq), 1 h after i.v. injection of $^{68}$Ga-IMP 288 in BALB/c nude mice with a subcutaneous LS174T and SK-RC52 tumor. Values are given as means±standard deviation (n=5).

The biodistribution of $^{125}$I-TF2 and $^{68}$Ga-IMP 288 in the mice are shown in FIG. 6. Again high uptake of the bsMAb (2.17±0.50% ID/g) and peptide (10.7±3.6% ID/g) in the tumor was observed, with very low uptake in the normal tissues (tumor-to-blood ratio: 64±22). Targeting of $^{68}$Ga-IMP 288 in the CEA-negative tumor SK-RC 52 was very low (0.35±0.35% ID/g). Likewise, tumors that were not pretargeted with TF2 had low uptake of $^{68}$Ga-IMP 288 (0.20±0.03% ID/g), indicating the specific accumulation of IMP 288 in the CEA-expressing LS174T tumor.

The specific uptake of $^{68}$Ga-IMP 288 in the CEA-expressing tumor pretargeted with TF2 was clearly visualized in a PET image acquired 1 h after injection of the $^{68}$Ga-labeled peptide (not shown). Uptake in the tumor was evaluated quantitatively by drawing regions of interest (ROI), using a 50% threshold of maximum intensity. A region in the abdomen was used as background region. The tumor-to-background ratio in the image of the mouse that received TF2 and $^{68}$Ga-IMP 288 was 38.2.

We then examined pretargeted immunoPET with [$^{18}$F] FDG. In two groups of five mice a s.c. LS174T tumor was induced on the right hind leg and an inflammatory focus in the left thigh muscle was induced by intramuscular injection of 50 µL turpentine (18). Three days after injection of the turpentine, one group of mice received 6.0 nmol TF2, followed 16 h later by 5 MBq $^{68}$Ga-IMP 288 (0.25 nmol). The other group received [$^{18}$F]FDG (5 MBq). Mice were fasted during 10 hours prior to the injection and anaesthetized and kept warm at 37° C. until euthanasia, 1 h post injection.

Figure 7:
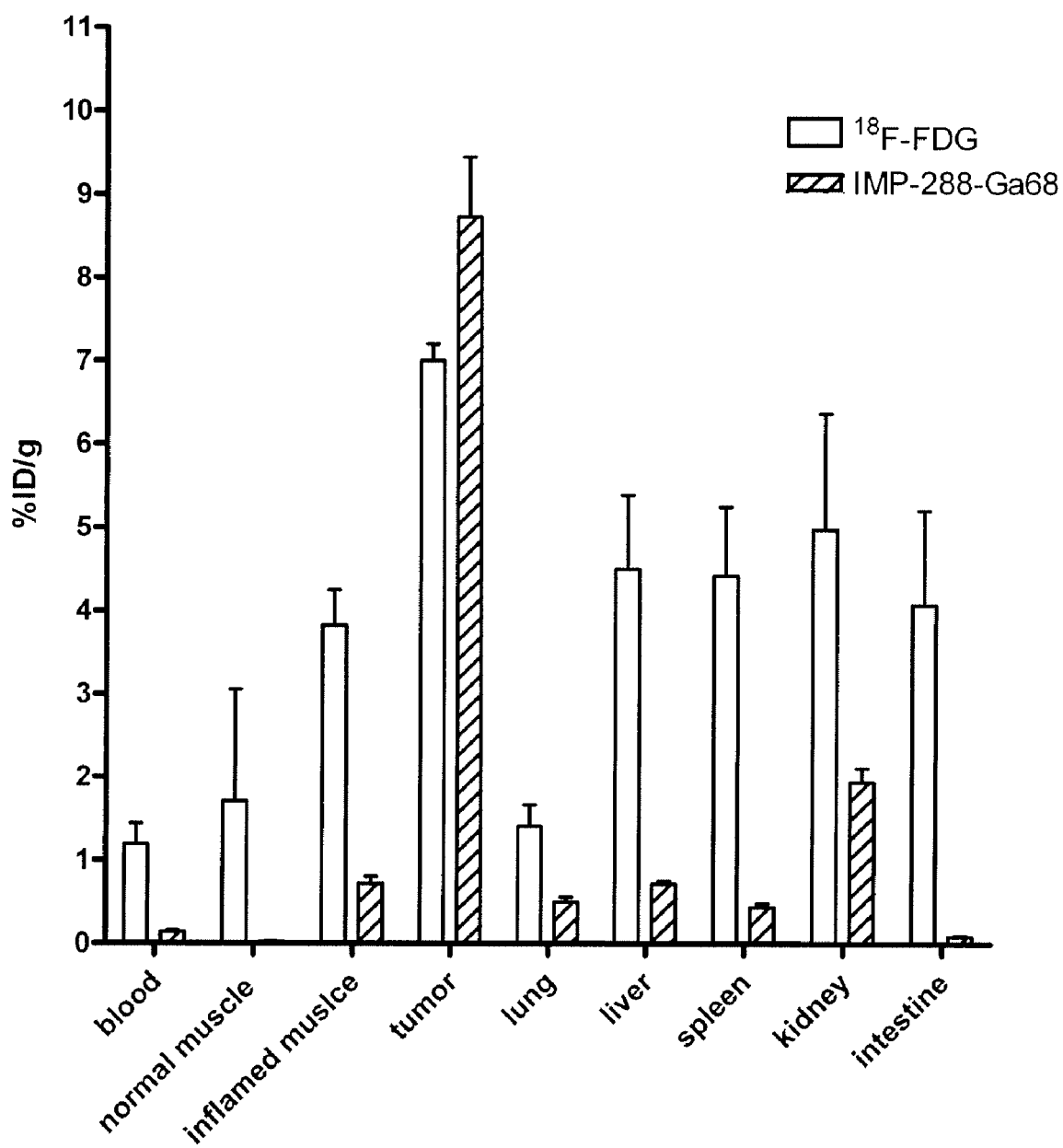
FIG. 7. Biodistribution of 5 MBq FDG and of 5 MBq $^{68}$Ga-IMP 288 (0.25 nmol) 1 hour after i.v. injection following pretargeting with 6.0 nmol TF2. Values are given as means±standard deviation (n=5).

Uptake of $^{68}$Ga-IMP 288 in the inflamed muscle was very low, while uptake in the tumor in the same animal was high (0.72±0.20% ID/g versus 8.73±1.60% ID/g, p<0.05, FIG. 7). Uptake in the inflamed muscle was in the same range as uptake in the lungs, liver and spleen (0.50±0.14% ID/g, 0.72±0.07% ID/g, 0.44±0.10% ID/g, respectively). Tumor-to-blood ratio of $^{68}$Ga-IMP 288 in these mice was 69.9±32.3; inflamed muscle-to-blood ratio was 5.9±2.9; tumor-to-inflamed muscle ratio was 12.5±2.1. In the other group of mice $^{18}$F-FDG accreted efficiently in the tumor (7.42±0.20% ID/g, tumor-to-blood ratio 6.24±1.5, FIG. 4). $^{18}$F-FDG also substantially accumulated in the inflamed muscle (4.07±1.13% ID/g), with inflamed muscle-to-blood ratio of 3.4±0.5, and tumor-to-inflamed muscle ratio of 1.97±0.71.

Figure 8:
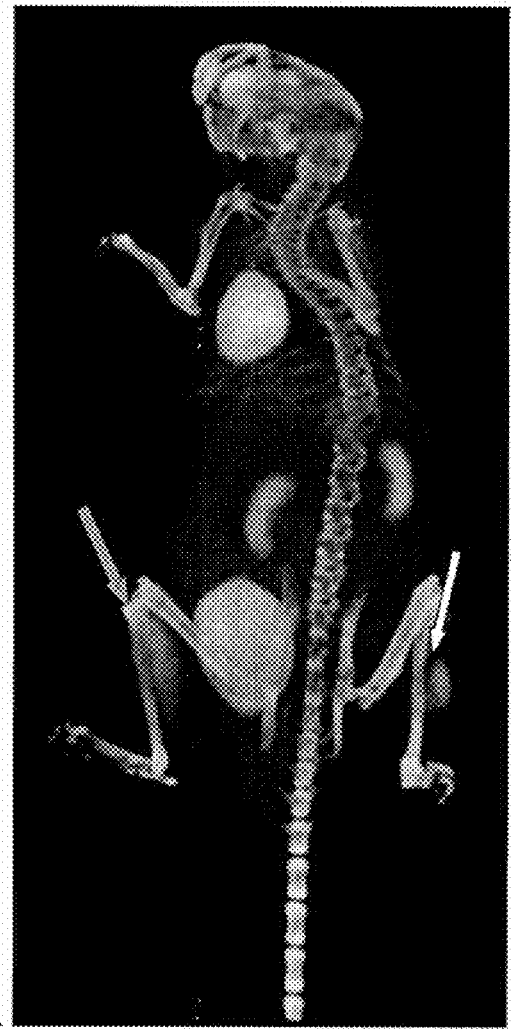
FIG. 8. PET/CT images of a BALB/c nude mouse with a subcutaneous LS174T tumor (0.1 g) on the right hind leg (light arrow) and a inflammation in the left thigh muscle (dark arrow), that received 5 MBq $^{18}$F-FDG, and one day later 6.0 nmol TF2 and 5 MBq $^{68}$Ga-IMP 288 (0.25 nmol) with a 16 hour interval. The animal was imaged one hour after the $^{18}$F-FDG and $^{68}$Ga-IMP 288 injection. The panel shows the 3D volume rendering (A), transverse sections of the tumor region (B) of the FDG-PET scan, and the 3D volume rendering (C), transverse sections of the tumor region (D) of the pretargeted immunoPET scan.
Figure 8:
Figure 8:
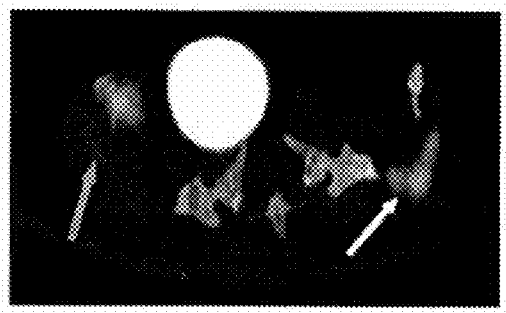
Figure 8:

The corresponding PET/CT image of a mouse that received $^{68}$Ga-IMP 288, following pretargeting with TF2, clearly showed the efficient accretion of the radiolabeled peptide in the tumor, while the inflamed muscle was not visualized (FIG. 8). In contrast, on the images of the mice that received $^{18}$F-FDG, the tumor as well as the inflammation was visible (FIG. 8). In the mice that received $^{68}$Ga-IMP 288, the tumor-to-inflamed tissue ratio was 5.4; tumor-to-background ratio was 48; inflamed muscle-to-background ratio was 8.9. [$^{18}$F] FDG uptake had a tumor-to-inflamed muscle ratio of 0.83; tumor-to-background ratio was 2.4; inflamed muscle-to-background ratio was 2.9.

Figure 9:
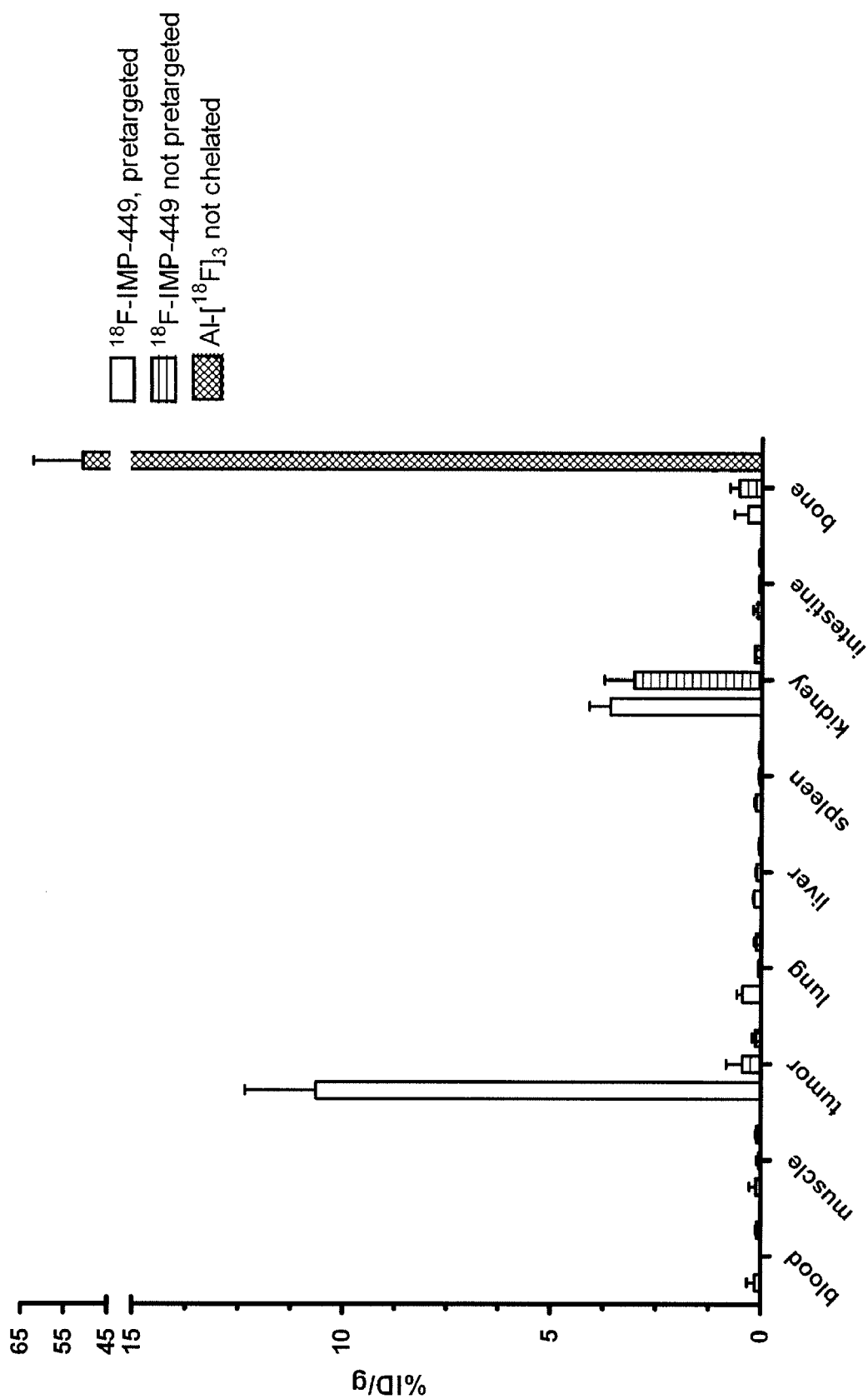
FIG. 9. Biodistribution of 0.25 nmol Al$^{18}$F-IMP 449 (5 MBq) 1 hour after i.v. injection of 6.0 nmol TF2 16 hours earlier, biodistribution of Al$^{18}$F-IMP 449 without pretargeting, or biodistribution of Al[$^{18}$F]. Values are given as means ± standard deviation.

The pretargeted immunoPET imaging method was tested using the Al$^{18}$F-labeled IMP 449. Five mice received 6.0 nmol TF2, followed 16 h later by 5 MBq Al$^{18}$F-IMP 449 (0.25 nmol). Three additional mice received 5 MBq Al$^{18}$F-IMP 449 without prior administration of TF2, while two control mice were injected with [Al$^{18}$F] (3 MBq). The results of this experiment are summarized in FIG. 9. Uptake of Al$^{18}$F-IMP 449 in tumors pretargeted with TF2 was high (10.6±1.7 ID/g), whereas it was very low in the non-pretargeted mice (0.45±0.38%ID/g). [Al$^{18}$F] accumulated in the bone (50.9±11.4% ID/g), while uptake of the radiolabeled IMP 449 peptide in the bone was very low (0.54±0.2% ID/g), indicating that the Al$^{18}$F-IMP 449 was stable in vivo. The biodistribution of Al$^{18}$F-IMP 449 in the TF2 pretargeted mice with s.c. LS174T tumors were highly similar to that of $^{68}$Ga-IMP 288.

Figure 10:
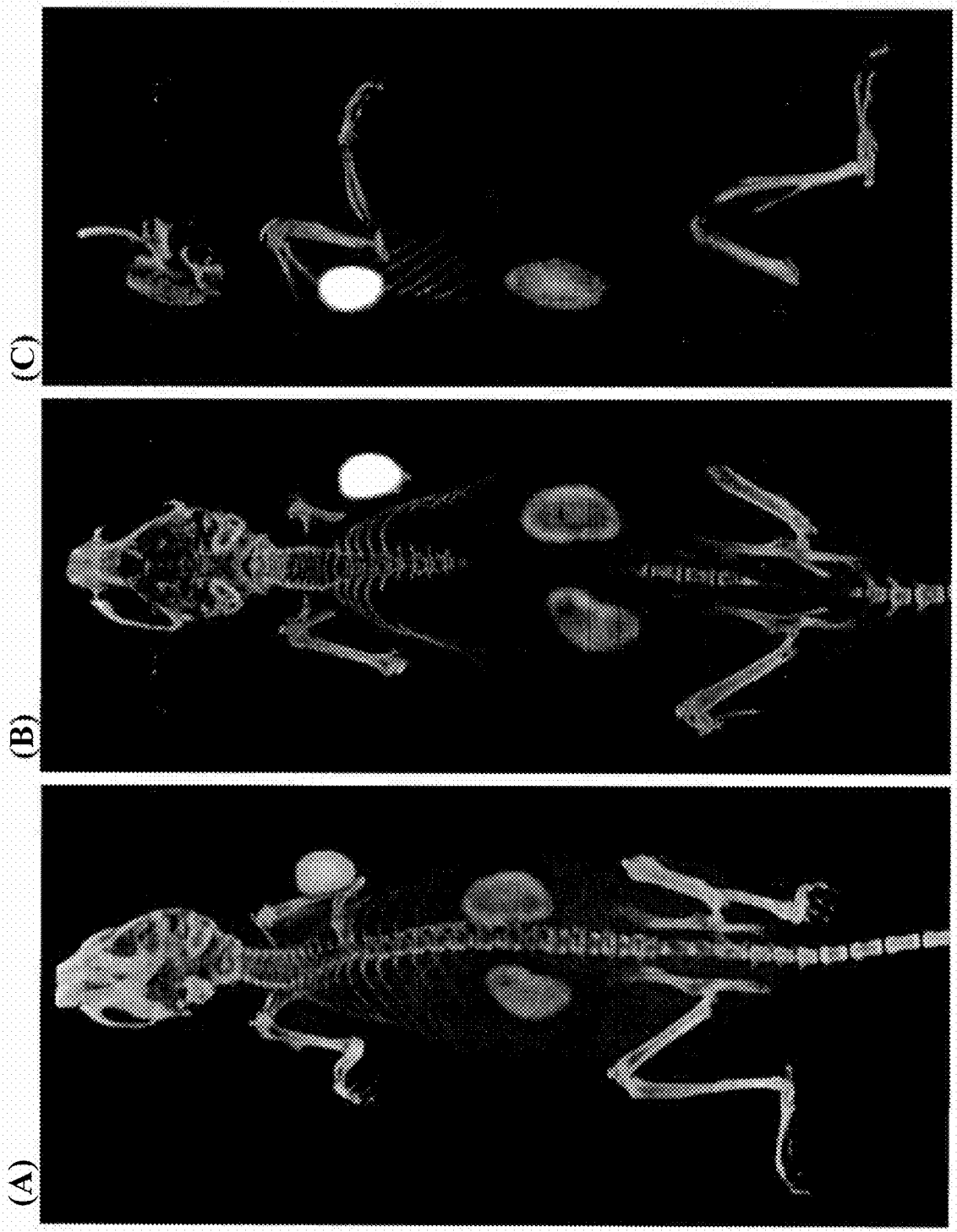
FIG. 10. Static PET/CT imaging study of a BALB/c nude mouse with a subcutaneous LS174T tumor (0.1 g) on the right side (arrow), that received 6.0 nmol TF2 and 0.25 nmol Al$^{18}$F-IMP 449 (5 MBq) intravenously with a 16 hour interval. The animal was imaged one hour after injection of Al$^{18}$F-IMP 449. The panel shows the 3D volume rendering (A) posterior view, and cross sections at the tumor region, (B) coronal, (C) sagittal.

The PET-images of pretargeted immunoPET with Al$^{18}$F-IMP 449 show the same intensity in the tumor as those with $^{68}$Ga-IMP 288, but the resolution of the $^{18}$F-images was superior to those of the $^{68}$Ga-images (FIG. 10). The tumor-to-background ratio of the Al$^{18}$F-IMP 449 signal was 66.

Conclusions

The present study showed that pretargeted immunoPET with the anti-CEAxanti-HSG bispecific antibody TF2 in combination with a $^{68}$Ga- or $^{18}$F-labeled di-HSG-DOTA-peptide is a rapid and specific technique for PET imaging of CEA-expressing tumors.

Pretargeted immunoPET with TF2 in combination with $^{68}$Ga-IMP 288 or Al$^{18}$F-IMP 449 involves two intravenous administrations. An interval between the infusion of the bsMAb and the radiolabeled peptide of 16 h was used. After 16 h most of the TF2 had cleared from the blood (blood concentration <1% ID/g), preventing complexation of TF2 and IMP 288 in the circulation.

For these studies the procedure to label IMP 288 with $^{68}$Ga was optimized, resulting in a one-step labeling technique. We found that purification on a C18/HLB cartridge was needed to remove the $^{68}$Ga colloid that is formed when the peptide was labeled at specific activities exceeding 150 GBq/nmol at 95° C. If a preparation contains a small percentage of colloid and is administered intravenously, the $^{68}$Ga colloid accumulates in tissues of the mononuclear phagocyte system (liver, spleen, and bone marrow), deteriorating image quality. The $^{68}$Ga-labeled peptide could be rapidly purified on a C18-cartridge. Radiolabeling and purification for administration could be accomplished within 45 minutes.

The half-life of $^{68}$Ga matches with the kinetics of the IMP 288 peptide in the pretargeting system: maximum accretion in the tumor is reached within 1 h. $^{68}$Ga can be eluted twice a day form a $^{68}$Ge/$^{68}$Ga generator, avoiding the need for an on-site cyclotron. However, the high energy of the positrons emitted by $^{68}$Ga (1.9 MeV) limits the spatial resolution of the acquired images to 3 mm, while the intrinsic resolution of the microPET system is as low as 1.5 mm.

$^{18}$F, the most widely used radionuclide in PET, has an even more favorable half-life for pretargeted PET imaging ($t_{1/2}$=110 min). The NOTA-conjugated peptide IMP 449 was labeled with $^{18}$F, as described above. Like labeling with $^{68}$Ga, it is a one-step procedure. Labeling yields as high as 50% were obtained. The biodistribution of Al$^{18}$F-IMP 449 was highly similar to that of $^{68}$Ga-labeled IMP 288, suggesting that with this labeling method $^{18}$F is a residualizing radionuclide.

In contrast with FDG-PET, pretargeted radioimmunodetection is a tumor specific imaging modality. Although a high sensitivity and specificity for FDG-PET in detecting recurrent colorectal cancer lesions has been reported in patients (Huebner et al., 2000, J Nucl Med 41:11277-89), FDG-PET images could lead to diagnostic dilemmas in discriminating malignant from benign lesions, as indicated by the high level of labeling observed with inflammation. In contrast, the high tumor-to-background ratio and clear visualization of CEA-positive tumors using pretargeted immunoPET with TF2 $^{68}$Ga- or $^{18}$F-labeled peptides supports the use of the described methods for clinical imaging of cancer and other conditions. Apart from detecting metastases and discriminating CEA-positive tumors from other lesions, pretargeted immunoPET could also be used to estimate radiation dose delivery to tumor and normal tissues prior to pretargeted radioimmunotherapy. As TF2 is a humanized antibody, it has a low immunogenicity, opening the way for multiple imaging or treatment cycles.

Example 23

Synthesis of Folic Acid NOTA Conjugate

Folic acid is activated as described (Wang et. al. Bioconjugate Chem. 1996, 7, 56-62.) and conjugated to Boc-NH—CH$_2$—CH$_2$—NH$_2$. The conjugate is purified by chromatography. The Boc group is then removed by treatment with TFA. The amino folate derivative is then mixed with p-SCN-Bn-NOTA (Macrocyclics) in a carbonate buffer. The product is then purified by HPLC. The folate-NOTA derivative is labeled with Al$^{18}$F as described in the preceding Examples and then HPLC purified. The $^{18}$F-labeled folate is injected i.v. into a subject and successfully used to image the distribution of folate receptors, for example in cancer or inflammatory diseases (see, e.g., Ke et al., Advanced Drug Delivery Reviews, 56:1143-60, 2004).

Example 24

Pretargeted PET Imaging in Humans

A patient (1.7 m$^2$ body surface area) with a suspected recurrent tumor is injected with 17 mg of bispecific monoclonal antibody (bsMab). The bsMab is allowed to localize to the target and clear from the blood. The $^{18}$F-labeled peptide (5-10 mCi on $5.7 \times 10^{-9}$ mol) is injected when 99% of the bsMab has cleared from the blood. PET imaging shows the presence of micrometastatic tumors.

Example 25

Imaging of Angiogenesis Receptors by $^{18}$F Labeling

Labeled Arg-Gly-Asp (RGD) peptides have been used for imaging of angiogenesis, for example in ischemic tissues, where $\alpha_v\beta_3$ integrin is involved. (Jeong et al., J. Nucl. Med. 2008, Apr. 15 epub). RGD is conjugated to SCN-Bn-NOTA according to Jeong et al. (2008). [Al$^{18}$F] is attached to the NOTA-derivatized RGD peptide as described above, by mixing aluminum stock solution with $^{18}$F and the derivatized RGD peptide and heating at 110° C. for 15 min, using an excess of peptide to drive the labeling reaction towards completion. The $^{18}$F labeled RGD peptide is used for in vivo biodistribution and PET imaging as disclosed in Jeong et al. (2008). The [Al$^{18}$F] conjugate of RGD-NOTA is taken up into ischemic tissues and provides PET imaging of angiogenesis.

Example 26

Carbohydrate Labeling

A NOTA thiosemicarbazide derivative is prepared by reacting the p-SCN-Bn-NOTA with hydrazine and then purifying the ligand by HPLC. [Al$^{18}$F] is prepared as described in the preceding Examples and the [Al$^{18}$F] is added to the NOTA thiosemicarbazide and heated for 15 min. Optionally the [Al$^{18}$F] NOTA thiosemicarbazide complex is purified by HPLC. The [Al$^{18}$F] NOTA thiosemicarbazide is conjugated to oxidized carbohydrates by known methods. The $^{18}$F-labeled carbohydrate is successfully used for imaging studies using PET scanning.

Example 27

Effect of Organic Solvents on F-18 Labeling

The affinity of chelating moieties such as NETA and NOTA for aluminum is much higher than the affinity of aluminum for $^{18}$F. The affinity of Al for $^{18}$F is affected by factors such as the ionic strength of the solution, since the presence of other counter-ions tends to shield the positively charged aluminum and negatively charged fluoride ions from each other and therefore to decrease the strength of ionic binding. Therefore low ionic strength medium should increase the effective binding of Al and $^{18}$F.

An initial study adding ethanol to the $^{18}$F reaction was found to increase the yield of radiolabeled peptide. IMP 461 was prepared as described above.

TABLE 8

$^{18}$F labeling of IMP 461 in ethanol

| # | 2 mM AlCl$_3$ | F-18 | 2 mM IMP 461 | Solvent | | Yield* |
|---|---|---|---|---|---|---|
| 1 | 10 µL | 741 µCi | 20 µL | EtOH | 60 µL | 64.9% |
| 2 | 10 µL | 739 µCi | 20 µL | H$_2$O | 60 µL | 21.4% |
| 3 | 10 µL | 747 µCi | 20 µL | EtOH | 60 µL | 46.7% |
| 4 | 5 µL | 947 µCi | 10 µL | EtOH | 60 µL | 43.2% |

*Yield after HLB column purification, Rxn # 1, 2 and 4 were heated to 101° C. for 5 minutes, Rxn # 3 was heated for 1 minute in a microwave oven.

Preliminary results showed that addition of ethanol to the reaction mixture more than doubled the yield of $^{18}$F-labeled peptide. Table 8 also shows that microwave irradiation can be used in place of heating to promote incorporation of [Al$^{18}$F] into the chelating moiety of IMP 461. Sixty seconds of microwave radiation (#3) appeared to be slightly less (18%) effective than heating to 101° C. for 5 minutes (#1).

The effect of additional solvents on 19F labeling of peptides was examined. In each case, the concentration of reactants was the same and only the solvent varied. Reaction conditions included mixing 25 µL Na$^{19}$F+20 µL AlCl$_3$+20 µL IMP-461+60 µL solvent, followed by heating at 101° C. for 5 min. Table 9 shows that the presence of a solvent does improve the yields of [Al$^{19}$F] IMP-461 (IMP 473) considerably.

TABLE 9

$^{19}$F labeling of IMP 461 in various solvents

| Solvent | H$_2$O | MeOH | EtOH | CH$_3$CN |
|---|---|---|---|---|
| Al-IMP-461 | 2.97 | 3.03 | 2.13 | 1.54 |
| IMP-465 | 52.46 | 34.19 | 31.58 | 24.58 |
| IMP-473 | 14.99 | 30.96 | 33.00 | 37.48 |
| IMP-473 | 15.96 | 31.81 | 33.29 | 36.40 |
| IMP-461 | 13.63 | — | — | — |

| Solvent | IPA | Acetone | THF | Dioxane |
|---|---|---|---|---|
| Al-IMP-461 | 2.02 | 2.05 | 2.20 | 16.67 |
| IMP-465 | 32.11 | 28.47 | 34.76 | 10.35 |
| IMP-473 | 27.31 | 34.35 | 29.38 | 27.09 |
| IMP-473 | 27.97 | 35.13 | 29.28 | 11.62 |
| IMP-461 | 10.58 | — | 4.37 | 34.27 |

| Solvent | DMF | DMSO | $t_R$ (min) |
|---|---|---|---|
| Al-IMP-461 | — | — | 9.739 |
| IMP-465 | 19.97 | 37.03 | 10.138 |
| IMP-473 | 27.77 | 31.67 | 11.729 |
| IMP-473 | 27.34 | 31.29 | 11.952 |
| IMP-461 | — | — | 12.535 |

[Al$^{19}$F] IMP 461 = IMP 473

Example 28

Elution of $^{18}$F with Bicarbonate $^{18}$F, 10.43 mCi, was received in 2 mL in a syringe. The solution was passed through a SEP-PAK® Light, WATERS® ACCELL™ Plus QMA Cartridge. The column was then washed with 5 mL of DI water. The $^{18}$F was eluted with 0.4 M KHCO$_3$ in fractions as shown in Table 10 below.

TABLE 10

Elution of QMA Cartridge with KHCO$_3$

| Vial | Vol. Acetic acid µL | Vol. 0.4M KHCO$_3$ µL | Activity mCi |
|---|---|---|---|
| 1 | 7.5 | 150 | 0.0208 |
| 2 | 10 | 200 | 7.06 |
| 3 | 5 | 100 | 1.653 |
| 4 | 25 | 500 | 0.548 |

The effects of the amount of additional solvent (CH$_3$CN) on $^{18}$F labeling of IMP-461 was examined. In each case, the concentration of reactants was the same and only the amount of solvent varied. Reaction conditions included mixing 10 µL AlCl$_3$+20 µL $^{18}$F+20 µL IMP-461+CH$_3$CN followed by heating at 101° C. for 5 min. Table 11 shows that following an initial improvement the labeling efficiency decreases in the presence of excess solvent.

TABLE 11

$^{18}$F labeling of IMP 461 using varying amounts of CH$_3$CN

| CH3CN (μL) | F-18 mCi | $t_R$ 2.70 min (%) | $t_R$ 8.70 min (%) | RCY % (HLB) |
|---|---|---|---|---|
| 0 | 0.642 | 13.48 | 86.52 | 50.7 |
| 100 | 0.645 | 1.55 | 98.45 | 81.8* |
| 200 | 0.642 | 2.85 | 97.15 | 80.8 |
| 400 | 0.645 | 14.51 | 85.49 | 57.8 |

*Aqueous wash contains labeled peptide. RCY = radiochemical yield after HLB purification

Example 29

High Dose Radiolabeling of IMP 461

$^{18}$F, 163 mCi, was received in 2 mL in a syringe. The solution was passed through a SEP-PAK® Light, WATERS® ACCELL™ Plus QMA Cartridge. The column was then washed with 5 mL of DI water. The $^{18}$F was eluted with 0.4 M K$_2$CO$_3$ in fractions as shown in Table 12.

TABLE 12

High Dose Labeling

| Vial | Vol. Acetic acid μL | Vol. 0.4M K$_2$CO$_3$ μL | Activity mCi |
|---|---|---|---|
| 1 | 18.5 | 185 | 5.59 |
| 2 | 5 | 50 | 35.8 |
| 3 | 5 | 50 | 59.9 |
| 4 | 5 | 50 | 20.5 |
| 5 | 5 | 50 | 5.58 |
| 6 | 50 | 500 | 4.21 |

An aluminum chloride solution (10 μL, 2 mM in pH 4, 2 mM NaOAc) was added to vial number 3 from Table 12. The peptide (20 μL, 2 mM in pH 4, 2 mM NaOAc) was added to the vial followed by the addition of 170 μL of CH$_3$CN. The solution was heated for 10 min at 103° C. the diluted with 6 mL of water. The solution was pulled into a 10 mL syringe and injected onto two WATERS® HLB Plus Cartridges arranged in tandem. The cartridges were washed with 8 mL water. The radiolabeled peptide Al$^{18}$F IMP 461 was then eluted with 10 mL 1:1 EtOH/H$_2$O, 30.3 mCi, 63.5% yield, specific activity 750 Ci/mmol. The labeled peptide was free of unbound $^{18}$F by HPLC. The total reaction and purification time was 20 min.

Example 30

Preparation of $^{19}$F Labeled Peptides

Products containing $^{27}$Al and/or $^{19}$F are useful for certain applications like NMR imaging. An improved method for preparing [Al$^{19}$F] labeled compounds was developed. IMP 461 was prepared as described above and labeled with $^{19}$F. Reacting IMP 461 with AlCl$_3$+NaF resulted in the formation of three products (not shown). However, by reacting IMP 461 with AlF$_3$.6H$_2$O we obtained a higher yield of [Al$^{19}$F] IMP 461.

Synthesis of IMP 473: ([Al$^{19}$F] IMP 461) To (14.1 mg, 10.90 μmol) IMP 461 in 2 mL NaOAc (2 mM, pH 4.18) solution added (4.51 mg, 32.68 μmol) AlF$_3$.6H$_2$O and 500 μL ethanol. The pH of the solution to adjusted to 4.46 using 3 μL 1 N NaOH and heated in a boiling water bath for 30 minutes. The crude reaction mixture was purified by preparative RP-HPLC to yield 4.8 mg (32.9%) of IMP 473. HRMS (ESI-TOF) MH$^+$ expected 1337.6341; found 1337.6332

These results demonstrate that $^{19}$F labeled molecules may be prepared by forming metal-$^{19}$F complexes and binding the metal-$^{19}$F to a chelating moiety, as discussed above for $^{18}$F labeling. The instant Example shows that a targeting peptide of use for pretargeting detection, diagnosis and/or imaging may be prepared using the instant methods.

Example 31

Synthesis and Labeling of IMP 479, IMP 485 and IMP 487

Figure 11:
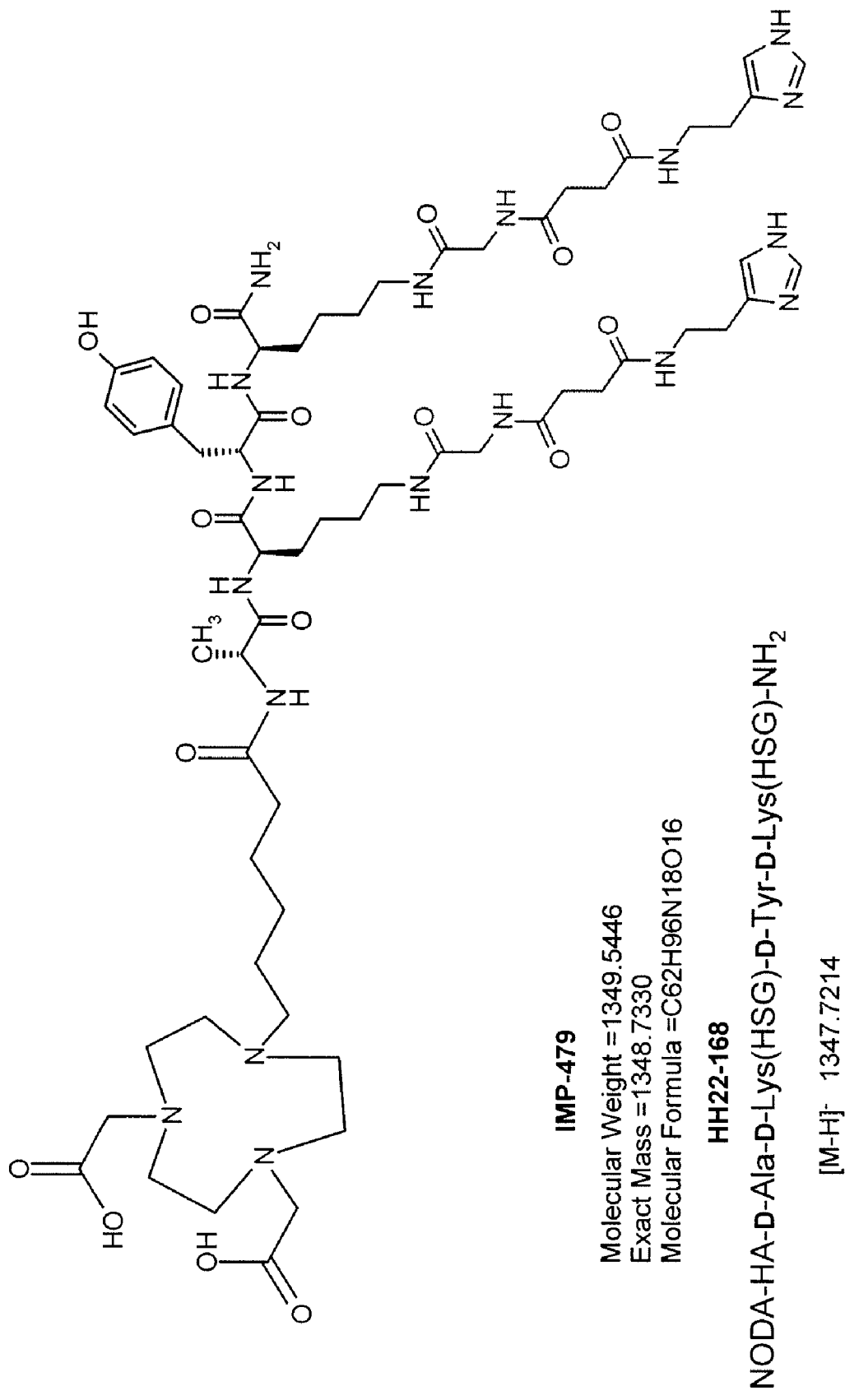
FIG. 11. Structure of IMP 479 (SEQ ID NO:35).
Figure 12:
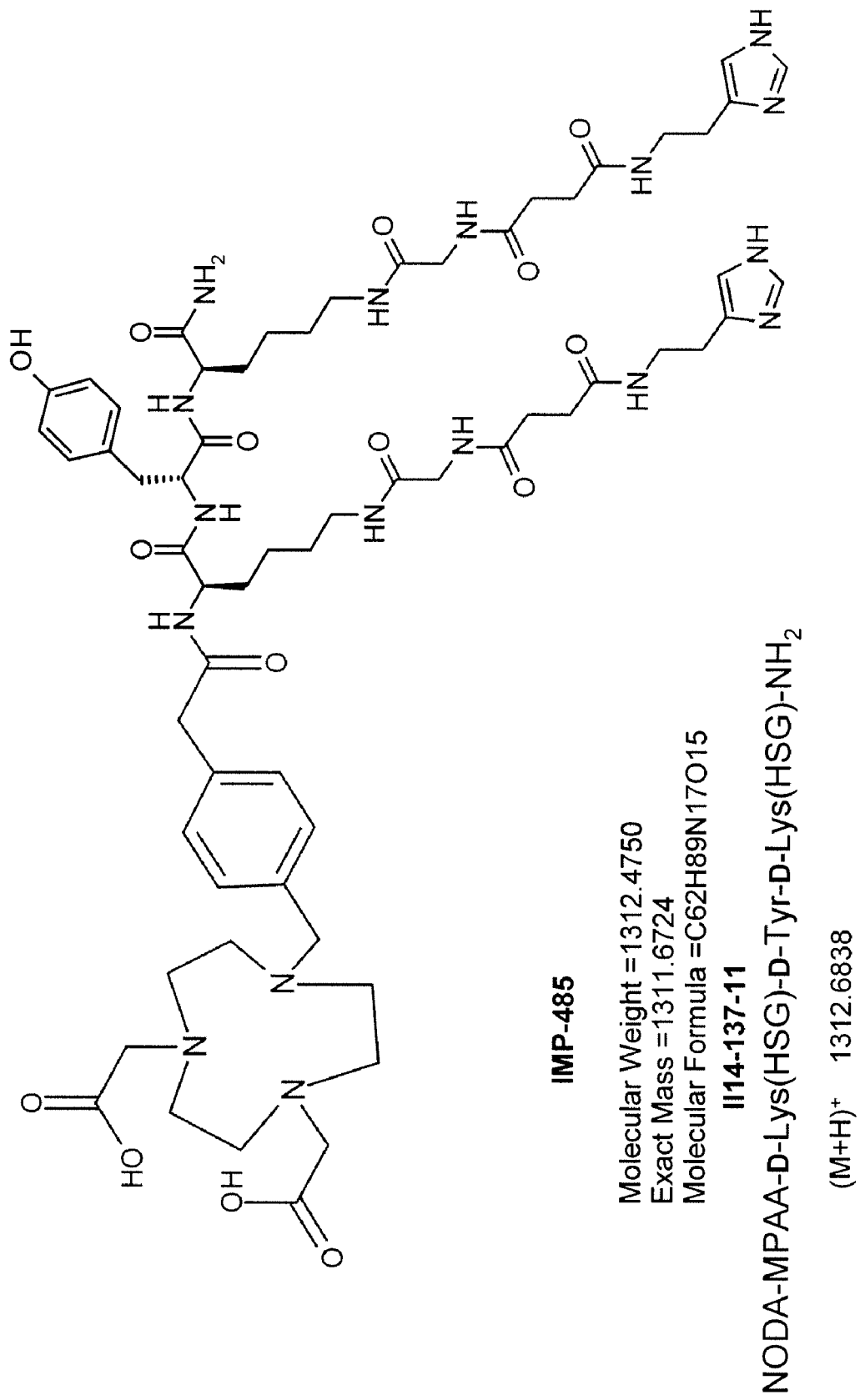
FIG. 12. Structure of IMP 485 (SEQ ID NO:36).
Figure 13:
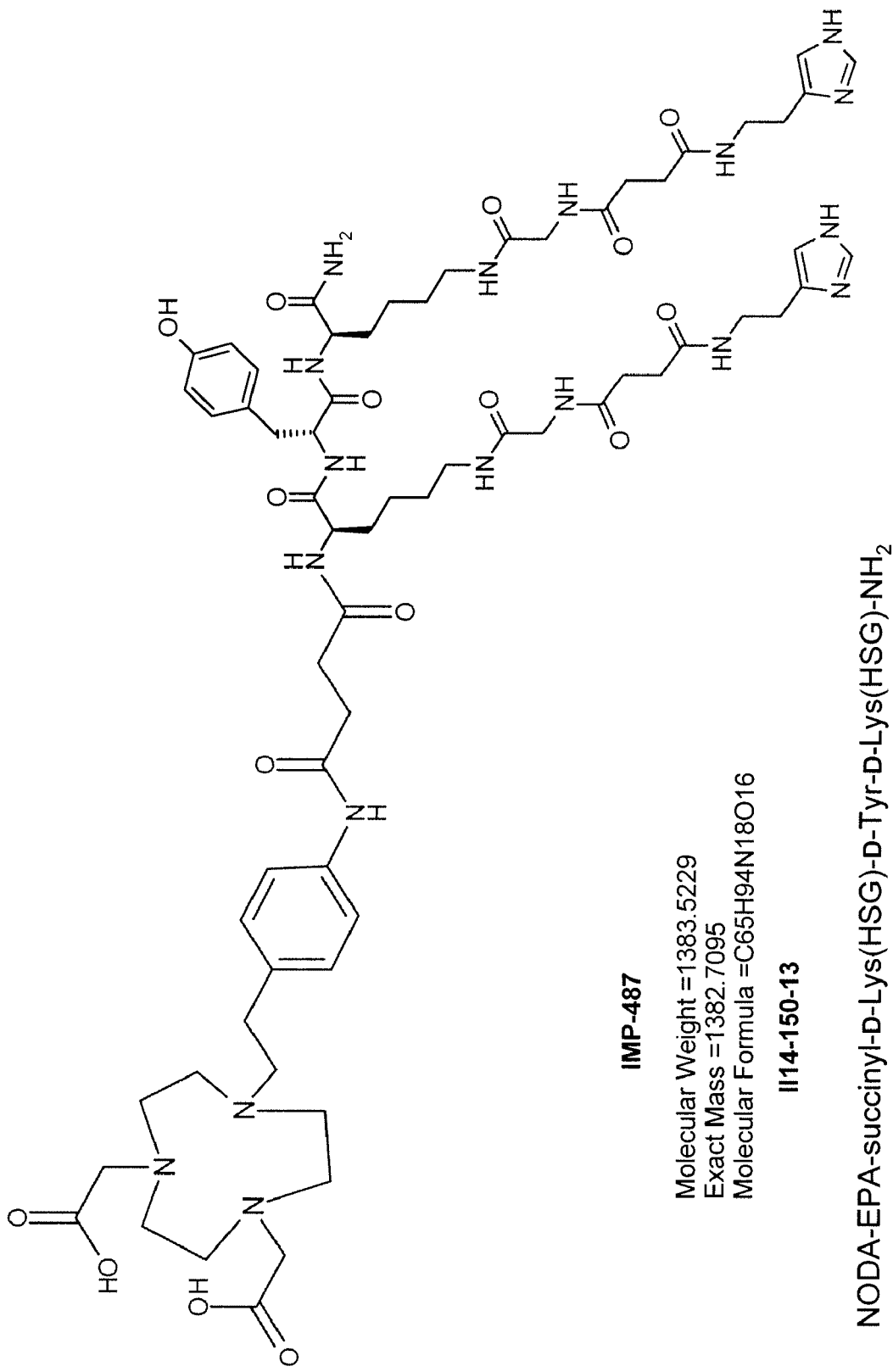
FIG. 13. Structure of IMP 487 (SEQ ID NO:37).

The structures of additional peptides IMP 479 (SEQ ID NO:35), IMP 485 (SEQ ID NO:36) and IMP 487 (SEQ ID NO:37) designed for $^{18}$F-labeling are shown in FIG. 11 to FIG. 13. IMP 485 is shown in FIG. 12. IMP 485 was made on Sieber Amide resin by adding the following amino acids to the resin in the order shown: Aloc-D-Lys(Fmoc)-OH, Trt-HSG-OH, the Aloc was cleaved, Fmoc-D-Tyr(But)-OH, Aloc-D-Lys(Fmoc)-OH, Trt-HSG-OH, the Aloc was cleaved, (tert-Butyl)$_2$NODA-MPAA (methyl phenyl acetic acid). The peptide was then cleaved from the resin and purified by RP-HPLC to yield 44.8 mg of IMP 485.

Synthesis of Bis-t-butyl-NODA-MPAA: NO2AtBu-MPAA for IMP 485 Synthesis

To a solution of 4-(bromomethyl)phenyl acetic acid (Aldrich 310417) (0.5925 g, 2.59 mmol) in CH$_3$CN (anhydrous) (50 mL) at 0° C. was added dropwise over 1 h a solution of NO2AtBu (1.0087 g, 2.82 mmol) in CH$_3$CN (50 mL). After 4 h anhydrous K$_2$CO$_3$ (0.1008 g, 0.729 mmol) was added to the reaction mixture and allowed to stir at room temperature overnight. Solvent was evaporated and the crude mixture was purified by preparative RP-HPLC to yield a white solid (0.7132 g, 54.5%).

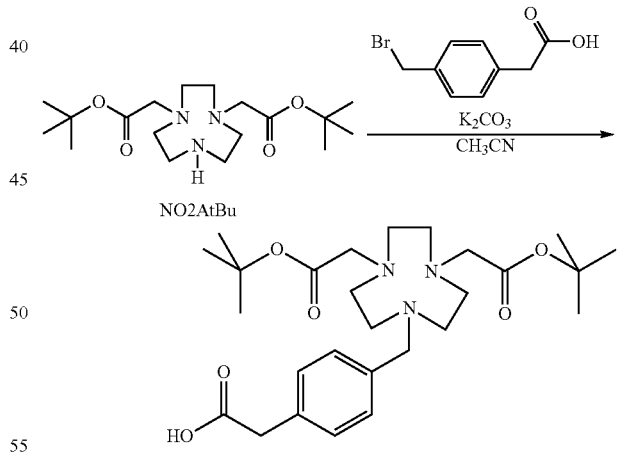

Figure 14:
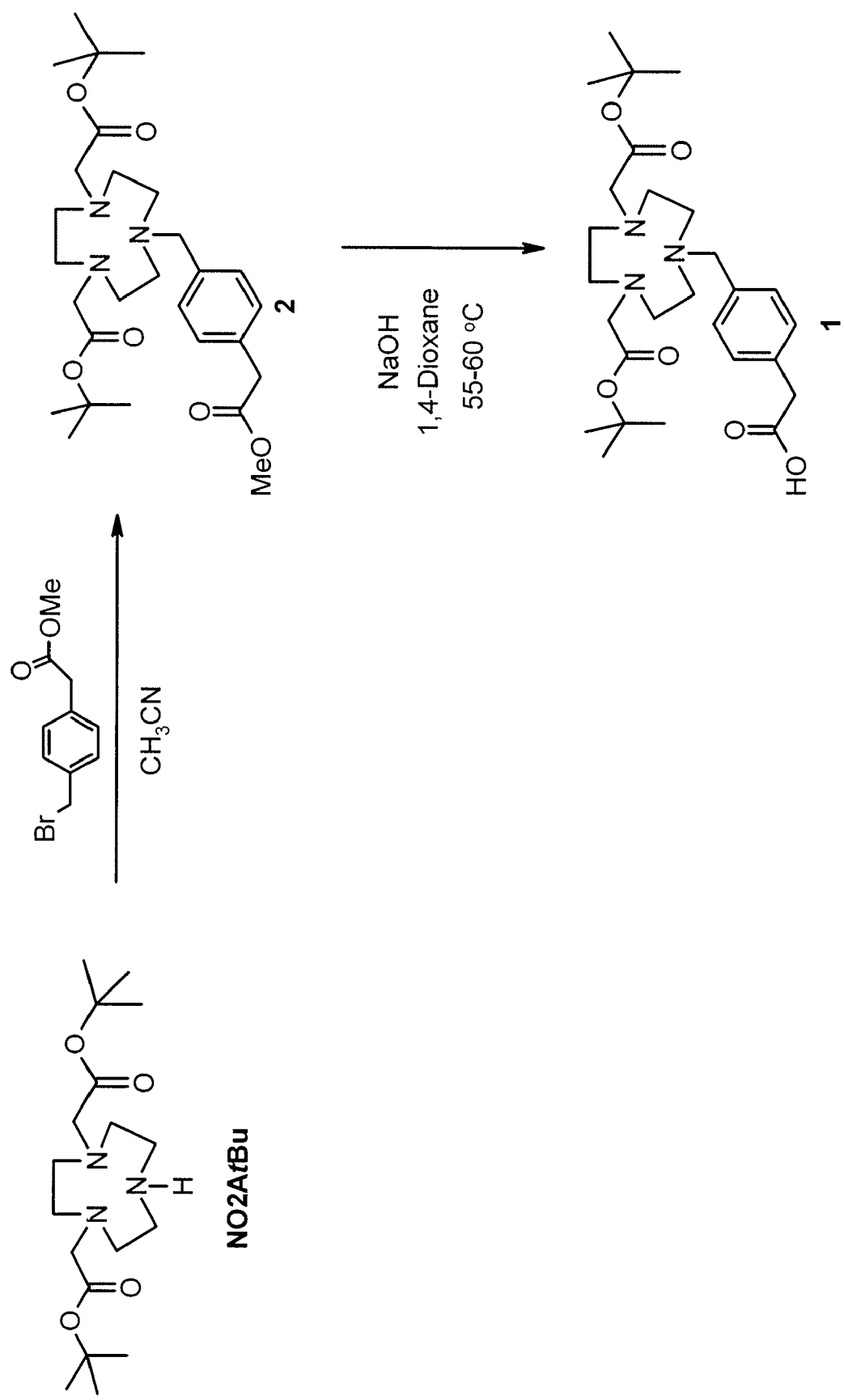
FIG. 14. Synthesis of bis-t-butyl-NODA-MPAA.

Although this is a one step synthesis, yields were low due to esterification of the product by 4-(bromomethyl)phenylacetic acid. Alkylation of NO2AtBu using methyl(4-bromomethyl)phenylacetate was employed to prevent esterification (FIG. 14).

$^{18}$F Labeling

For $^{18}$F labeling studies in water, to 40 nmol of IMP-479/485/487 (formulated using trehalose+ascorbic acid+AlCl$_3$) was added 250 μL F-18 solution [~919-1112 μCi of F-18] and heated to 101° C. for 15 minutes. In ethanol, to 40 nmol of IMP-479/485/487 (formulated using trehalose+ascorbic acid+AlCl$_3$) was added 250 µL F-18 solution [131.248-1.693 mCi of F-18], 100 µL EtOH and heated to 101° C. for 15 minutes. An exemplary experiment showing labeling of different peptides is shown in Table 13. With minimal optimization, radiolabeling of IMP 485 has been observed with up to an 88% yield and a specific activity of 2,500 Ci/mmol. At this specific activity, HPLC purification of the radiolabeled peptide is not required for in vivo PET imaging using the radiolabeled peptide.

TABLE 13

Labeling of IMP 479, IMP 485 and IMP 487

| IMP # | Isolated yields after HLB purification | |
|---|---|---|
| | H$_2$O | EtOH |
| IMP-479 | 44.0% | 57.5% |
| IMP 485 | 74.4% | 79.7% |
| IMP-487 | 63.6% | 81.6% |

Stability in Serum

A kit containing 40 nmol of IMP 485 or IMP 487, 20 nmol AlCl$_3$, 0.1 mg ascorbic acid and 0.1 g trehalose adjusted to pH 3.9 was reconstituted with purified $^{18}$F in 200 µL saline and heated 106° C. for 15 min. The reaction mixture was then diluted with 800 µL water and placed on an HLB column. After washing, the column was eluted with 2×200 µL 1:1 EtOH/H$_2$O to obtain the purified $^{18}$F-IMP 485 in 64.6% isolated yield. The radiolabeled peptide in 50 µL was mixed with 250 µL of fresh human serum in a vial and incubated at 37° C.

Both radiolabeled peptides were stable at 37° C. in fresh human serum over the four hours tested (not shown).

Effect of Bulking Agents on Yield of Lyophilized Peptide

An experiment was performed to compare yield using IMP 485 kits (40 nmol) with different bulking agents labeled with 2 mCi of F-18 (from the same batch of F-18) in 200 microliters of saline. The bulking agents were introduced at a concentration of 5% by weight in water with a dose of 200 microliters/vial. We tested sorbitol, trehalose, sucrose, mannitol and glycine as bulking agents. Results are shown in Table 14

TABLE 14

Effects of Bulking Agents on Radiolabeling Yield

| Bulking Agent | Activity mCi | Yield % |
|---|---|---|
| Sorbitol | 2.17 | 82.9 |
| Glycine | 2.17 | 41.5 |
| Mannitol | 2.11 | 81.8 |
| Sucrose | 2.11 | 66.1 |
| Trehalose | 2.10 | 81.3 |

Sorbitol, mannitol and trehalose all gave radiolabeled product in the same yield. The mannitol kit and the trehalose kit both formed nice cakes. The sucrose kit and the glycine kit both had significantly lower yields. We also recently tested 2-hydroxypropyl-beta-cyclodextrin as a bulking agent and obtained a 58% yield for the 40 nmol kit. We have found that radiolabeling is very pH sensitive and needs to be tuned to the ligand and possibly even to the peptide+the ligand. In the case of IMP 485 the optimal pH is pH 4.0±0.2 whereas the optimal pH for IMP 467 was pH 4.5±0.5. In both cases the yields drop off rapidly outside the ideal pH zone.

Time Course of Labeling

The time course for labeling of IMP 485 was examined. To 40 nmol of IMP 485 (formulated using trehalose+AlCl$_3$ (20 nmol)+ascorbic acid) was added ~200-250 µL F-18 solution (0.9% saline) and heated to 104° C. for 5 to 15 minutes. The results for labeling yield were: 5 min (28.9%), 10 min (57.9%), 15 min (83.7%) and 30 min (88.9%). Thus, the time course for labeling was approximately 15 minutes.

Biodistribution of IMP 485 Alone

The biodistribution of IMP 485 in the absence of any pretargeting antibody was examined in female Taconic nude mice (10 week old) bearing small or no BXPC3 pancreatic cancer xenografts. The mice were injected i.v. with $^{18}$F-IMP 485, (340 µCi, 2.29×109 mol, 100 µL in saline). The mice, 6 per time point, were necropsied at 30 min and 90 min post injection. In the absence of pretargeting antibody a low level of accumulation was seen in tumor and most normal tissues. The substantial majority of radiolabel was found in the bladder and to a lesser extent in kidney. Most of the activity was cleared before the 90 min time point.

Pretargeting of IMP 485 with TF2 DNL Targeting Molecule $^{18}$F-IMP 485 Radiolabeling—$^{18}$F (218 mCi) was purified to isolate 145.9 mCi. The purified $^{18}$F (135 mCi) was added to a lyophilized vial containing 40 nmol of pre-complexed Al-IMP 485. The reaction vial was heated at 110° C. for 17 min. Water (0.8 mL) was added to the reaction mixture before HLB purification. The product (22 mCi) was eluted with 0.6 mL of water:ethanol (1:1) mixture into a vial containing lyophilized ascorbic acid. The product was diluted with saline. The $^{18}$F-Al IMP 485 specific activity used for injection was 550 Ci/mmol.

Biodistribution of $^{18}$F-Al IMP 485 alone—Mice bearing sc LS174T xenografts were injected with $^{18}$F-Al IMP 485 (28 µCi, 5.2×10$^{-11}$ mol, 100 µL. Mice were necropsied at 1 and 3 h post injection, 6 mice per time point.

Biodistribution of TF2+$^{18}$F-Al IMP 485 With Pretargeting at 20:1 bsMAb to peptide ratio—Mice bearing sc LS174T xenografts were injected with TF2 (163.2 µg, 1.03×10$^{-9}$ mol, iv) and allowed 16.3 h for clearance before injecting $^{18}$F-Al IMP 485 (28 µCi, 5.2×10$^{-11}$ mol, 100 µL iv). Mice were necropsied at 1 and 3 h post injection, 7 mice per time point.

Urine stability—Ten mice bearing s.c. Capan-1 xenografts were injected with $^{18}$F—Al-IMP 485 (400 µCi, in saline, 100 µL). Urine was collected from 3 mice at 55 min post injection. The urine samples were analyzed by reverse phase and SE HPLC. Stability of the radiolabeled IMP 485 in urine was observed.

TABLE 15

$^{18}$F-IMP 485 Alone at 1 h post injection:

| Tissue | n | Weight | STD WT | % ID/g | STD % ID/g | % ID/org | STD % ID/org | T/NT | STD T/NT |
|---|---|---|---|---|---|---|---|---|---|
| Tumor | 6 | 0.235 | 0.147 | 0.316 | 0.114 | 0.081 | 0.063 | 1.0 | 0.0 |
| Liver | 6 | 1.251 | 0.139 | 0.176 | 0.032 | 0.220 | 0.043 | 1.8 | 0.4 |
| Spleen | 6 | 0.085 | 0.019 | 0.210 | 0.181 | 0.018 | 0.017 | 1.9 | 0.9 |
| Kidney | 6 | 0.149 | 0.013 | 3.328 | 0.556 | 0.499 | 0.119 | 0.1 | 0.0 |

TABLE 15-continued

¹⁸F-IMP 485 Alone at 1 h post injection:

| Tissue | n | Weight | STD WT | % ID/g | STD % ID/g | % ID/org | STD % ID/org | T/NT | STD T/NT |
|---|---|---|---|---|---|---|---|---|---|
| Lung | 6 | 0.141 | 0.039 | 0.238 | 0.048 | 0.033 | 0.010 | 1.3 | 0.3 |
| Blood | 6 | 0.222 | 0.006 | 0.165 | 0.062 | 0.268 | 0.101 | 2.0 | 0.4 |
| Stomach | 6 | 0.478 | 0.083 | 0.126 | 0.110 | 0.057 | 0.045 | 3.5 | 1.6 |
| Sm Int. | 6 | 0.896 | 0.098 | 0.396 | 0.128 | 0.353 | 0.110 | 0.8 | 0.3 |
| Lg Int. | 6 | 0.504 | 0.056 | 0.081 | 0.019 | 0.041 | 0.010 | 3.9 | 0.9 |
| Muscle | 6 | 0.103 | 0.029 | 0.114 | 0.079 | 0.011 | 0.008 | 4.1 | 2.5 |
| Scapula | 6 | 0.057 | 0.015 | 0.107 | 0.019 | 0.006 | 0.001 | 2.9 | 0.7 |

TABLE 16

¹⁸F-IMP 485 Alone at 3 h post injection:

| Tissue | n | Weight | STD WT | % ID/g | STD % ID/g | % ID/org | STD % ID/org | T/NT | STD T/NT |
|---|---|---|---|---|---|---|---|---|---|
| Tumor | 6 | 0.265 | 0.126 | 0.088 | 0.020 | 0.022 | 0.011 | 1.0 | 0.0 |
| Liver | 6 | 1.219 | 0.091 | 0.095 | 0.047 | 0.114 | 0.056 | 13.6 | 31.4 |
| Spleen | 6 | 0.091 | 0.015 | 0.065 | 0.009 | 0.006 | 0.001 | 1.4 | 0.2 |
| Kidney | 6 | 0.154 | 0.013 | 2.265 | 0.287 | 0.345 | 0.028 | 0.0 | 0.0 |
| Lung | 6 | 0.142 | 0.008 | 0.073 | 0.019 | 0.010 | 0.003 | 1.3 | 0.6 |
| Blood | 6 | 0.236 | 0.019 | 0.008 | 0.005 | 0.013 | 0.007 | 21.0 | 27.9 |
| Stomach | 6 | 0.379 | 0.054 | 0.041 | 0.017 | 0.016 | 0.008 | 2.5 | 1.0 |
| Sm. Int. | 6 | 0.870 | 0.042 | 0.137 | 0.031 | 0.119 | 0.029 | 0.7 | 0.3 |
| Lg. Int. | 6 | 0.557 | 0.101 | 0.713 | 0.215 | 0.408 | 0.194 | 0.1 | 0.0 |
| Muscle | 6 | 0.134 | 0.038 | 0.013 | 0.007 | 0.002 | 0.001 | 203.9 | 486.6 |
| Scapula | 6 | 0.074 | 0.009 | 0.079 | 0.026 | 0.006 | 0.002 | 1.2 | 0.6 |

TABLE 17

TF2 + ¹⁸F-IMP 485, at 1 h post peptide injection:

| Tissue | n | Weight | STD WT | % ID/g | STD % ID/g | % ID/org | STD % ID/org | T/NT | STD T/NT |
|---|---|---|---|---|---|---|---|---|---|
| Tumor | 7 | 0.291 | 0.134 | 28.089 | 4.545 | 8.025 | 3.357 | 1 | 0 |
| Liver | 7 | 1.261 | 0.169 | 0.237 | 0.037 | 0.295 | 0.033 | 123 | 38 |
| Spleen | 7 | 0.081 | 0.013 | 0.254 | 0.108 | 0.020 | 0.008 | 139 | 87 |
| Kidney | 7 | 0.140 | 0.018 | 3.193 | 0.730 | 0.444 | 0.098 | 9 | 4 |
| Lung | 7 | 0.143 | 0.014 | 0.535 | 0.147 | 0.075 | 0.018 | 57 | 22 |
| Blood | 7 | 0.205 | 0.029 | 0.278 | 0.071 | 0.456 | 0.129 | 110 | 43 |
| Stomach | 7 | 0.473 | 0.106 | 0.534 | 1.175 | 0.265 | 0.598 | 381 | 318 |
| Sm. Int. | 7 | 0.877 | 0.094 | 0.686 | 0.876 | 0.586 | 0.725 | 75 | 39 |
| Lg. Int. | 7 | 0.531 | 0.068 | 0.104 | 0.028 | 0.055 | 0.015 | 291 | 121 |
| Muscle | 7 | 0.090 | 0.014 | 0.136 | 0.102 | 0.012 | 0.009 | 348 | 274 |
| Scapula | 6 | 0.189 | 0.029 | 0.500 | 0.445 | 0.095 | 0.092 | 120 | 108 |

TABLE 18

TF2 + ¹⁸F-IMP 485, at 3 h post peptide injection:

| Tissue | n | Weight | STD WT | % ID/g | STD % ID/g | % ID/org | STD ID/org | T/NT | STD T/NT |
|---|---|---|---|---|---|---|---|---|---|
| Tumor | 7 | 0.320 | 0.249 | 26.518 | 5.971 | 8.127 | 5.181 | 1 | 0 |
| Liver | 7 | 1.261 | 0.048 | 0.142 | 0.019 | 0.178 | 0.025 | 189 | 43 |
| Spleen | 7 | 0.079 | 0.012 | 0.138 | 0.031 | 0.011 | 0.002 | 195 | 41 |
| Kidney | 7 | 0.144 | 0.012 | 2.223 | 0.221 | 0.319 | 0.043 | 12 | 3 |
| Lung | 7 | 0.145 | 0.014 | 0.244 | 0.056 | 0.035 | 0.005 | 111 | 24 |
| Blood | 7 | 0.229 | 0.014 | 0.023 | 0.008 | 0.037 | 0.012 | 1240 | 490 |
| Stomach | 7 | 0.430 | 0.069 | 0.025 | 0.017 | 0.010 | 0.005 | 1389 | 850 |
| Sm. Int. | 7 | 0.818 | 0.094 | 0.071 | 0.029 | 0.059 | 0.028 | 438 | 207 |
| Lg. Int. | 7 | 0.586 | 0.101 | 0.353 | 0.160 | 0.206 | 0.103 | 86 | 33 |
| Muscle | 7 | 0.094 | 0.014 | 0.025 | 0.006 | 0.002 | 0.001 | 1129 | 451 |
| Scapula | 7 | 0.140 | 0.030 | 0.058 | 0.018 | 0.008 | 0.002 | 502 | 193 |

Conclusions

The IMP 485 labels as well as or better than IMP 467, with equivalent stability in serum. However, IMP 485 is much easier to synthesize than IMP 467. Preliminary studies have shown that $^{18}$F labeling of lyophilized IMP 485 works as well as non-lyophilized peptide (data not shown). The presence of alkyl or aryl groups in the linker joining the chelating moiety to the rest of the peptide was examined. The presence of aryl groups in the linker appears to increase the radiolabeling yield relative to the presence of alkyl groups in the linker.

Biodistribution of IMP 485 in the presence or absence of pretargeting antibody resembles that observed with IMP 467. In the absence of pretargeting antibody, distribution of radiolabeled peptide in tumor and most normal tissues is low and the peptide is removed from circulation by kidney excretion. In the presence of the TF2 antibody, radiolabeled IMP 485 is found primarily in the tumor, with little distribution to normal tissues. Kidney radiolabeling is substantially decreased in the presence of the pretargeting antibody. We conclude that IMP 485 and other peptides with aryl groups in the linker are highly suitable for PET imaging with $^{18}$F labeling.

Example 32

Kit Formulation of IMP 485 for Imaging

Reagents List

Reagents were obtained from the following sources: Acetic acid (JT Baker 6903-05 or 9522-02), Sodium hydroxide (Aldrich semiconductor grade 99.99% 30, 657-6), α,α-Trehalose (JT Baker 4226-04), Aluminum chloride hexahydrate (Aldrich 99% 237078), Ascorbic acid (Aldrich 25, 556-4).

Acetate Buffer 2 mM—Acetic acid, 22.9 µL ($4.0 \times 10^{-4}$ mol) was diluted with 200 mL water and neutralized with 6 N NaOH (~15 µL) to adjust the solution to pH 4.22.

Aluminum Solution 2 mM—Aluminum hexahydrate, 0.0225 g ($9.32 \times 10^{-5}$ mol) was dissolved in 47 mL DI water.

α,α-Trehalose Solution—α,α-Trehalose, 4.004 g was dissolved in 40 mL DI water to make a 10% solution.

Peptide Solution, IMP 485 2 mM—The peptide IMP 485 (0.0020 g, 1.52 µmol) was dissolved in 762 µL of 2 mM acetate buffer. The pH was 2.48 (the peptide was lyophilized as the TFA salt). The pH of the peptide solution was adjusted to pH 4.56 by the addition of 4.1 µL of 1 M NaOH.

Ascorbic Acid Solution 5 mg/mL—Ascorbic acid, 0.0262 g ($1.49 \times 10^{-4}$ mol) was dissolved in 5.24 mL DI water.

Formulation of Peptide Kit

The peptide, 20 µL (40 nmol) was mixed with 12 µL (24 nmol) of Al, 100 µL of trehalose, 20 µL (0.1 mg) ascorbic acid and 900 µL of DI water in a 3 mL lyophilization vial. The final pH of the solution should be ~pH 4.0. The vial was frozen, lyophilized and sealed under vacuum. In this formulation, the peptide is loaded with aluminum prior to binding $^{18}$F.

Ten and 20 nmol kits have also been made. These kits are made the same as the 40 nmol kits keeping the peptide to $Al^{3+}$ ratio of 1 peptide to 0.6 $Al^{3+}$ but formulated in 2 mL vials with a total fill of 0.5 mL.

Purification of $^{18}$F

The crude $^{18}$F was received in 2 mL of DI water in a syringe. The syringe was placed on a syringe pump and the liquid pushed through a Waters CM cartridge followed by a QMA cartridge. Both cartridges were washed with 10 mL DI water. A sterile disposable three way valve between the two cartridges was switched and 1 mL commercial sterile saline was pushed through the QMA cartridge in 200 µL fractions. The second fraction usually contains ~80% of the $^{18}$F regardless of the amount of $^{18}$F applied (10-300 mCi loads were tested).

We alternatively use commercial $^{18}$F in saline, which has been purified on a QMA cartridge. This is a concentrated version of the commercial bone imaging agent so it is readily available and used in humans. The activity is supplied in 200 µL in a 0.5 mL tuberculin syringe.

Radiolabeling

The peptide was radiolabeled by adding $^{18}$F in 200 µL saline to the lyophilized peptide in a crimp sealed vial and then heating the solution to 90-105° C. for 15 min. The peptide was purified by adding 800 mL of DI water in a 1 mL syringe to the reaction vial, removing the liquid with the 1 mL syringe and applying the liquid to a Waters HLB column (1 cc, 30 mg). The HLB column was placed on a crimp sealed 5 mL vial and the liquid was drawn into the vial under vacuum supplied by a remote (using a sterile disposable line) 10 mL syringe. The reaction vial was washed with two one mL aliquots of DI water, which were also drawn through the column. The column was then washed with 1 mL more of DI water. The column was then moved to a vial containing buffered lyophilized ascorbic acid (~pH 5.5, 15 mg). The radiolabeled product was eluted with three 200 µL portions of 1:1 EtOH/DI water. The yield was determined by measuring the activity on the HLB cartridge, in the reaction vial, in the water wash and in the product vial to get the percent yield.

Adding ethanol to the radiolabeling reaction can increase the labeling yield. A 20 nmol kit can be reconstituted with a mixture of 200 µL F-18 in saline and 200 µL ethanol. The solution is then heated to 100-110° C. in the crimp sealed vial for 15 min. After heating, the reaction is diluted with 3 mL water before purification on a 3 cc (60 mg) HLB extraction cartridge. The peptide can be labeled in good yield and up to 4,100 Ci/mmol specific activity using this method.

The yield for this kit and label as described was 80-90% when labeled with 1.0 mCi of $^{18}$F. When higher doses of $^{18}$F (~100 mCi) were used the yield dropped. However if ethanol is added to the labeling mixture the yield goes up. If the peptides are diluted too much in saline the yields will drop. The labeling is also very sensitive to pH. For our peptide with this ligand we have found that the optimal pH for the final formulation was pH 4.0±0.2.

The purified radiolabeled peptide in 50 µL 1:1 EtOH/H$_2$O was mixed with 150 µL of human serum and placed in the HPLC autosampler heated to 37° C. and analyzed by RP-HPLC. No detectable $^{18}$F above background at the void volume was observed even after 4 h.

TABLE 19

IMP 485 Labeling

| Vial #/ Peptide | nmol of Peptide | Volume Saline µL | Volume EtOH µL | Activity at start mCi | Activity of isolated product mCi | % Yield | Specific Activity Ci/mmol |
|---|---|---|---|---|---|---|---|
| 1. IMP485 | 10 | 100 | 0 | 20.0 | 7.10 | 62 | |
| 2. IMP485 | 10 | 50 | 50 | 19.4 | 9.43 | 78 | |
| 3. IMP485 | 10 | 200 | 0 | 19.07 | 5.05 | 38 | |
| 4. IMP485 | 20 | 100 | 100 | 37.3 | 22.3 | 80 | |
| 5. IMP485 | 10 | 100 | 0 | 45.7 | 16.2 | 42 | |
| 6. IMP485 | 20 | 200 | 200 | 175.6 | 82.7 | 58 | 4135 |

Synthesis and Radiolabeling of IMP 486 (Al-OHIMP485)

IMP 485 (21.5 mg, 0.016 mmol) was dissolved in 1 mL of 2 mM NaOAc, pH 4.4 and treated with AlCl$_3$.6H$_2$O (13.2 mg, 0.055 mmol). The pH was adjusted to 4.5-5.0 and the reaction mixture was refluxed for 15 minutes. The crude mixture was purified by preparative RP-HPLC to yield a white solid (11.8 mg).

The pre-filled Al-NOTA complex (IMP 486) was also radiolabeled in excellent yield after formulating into lyophilized kits. The labeling yields with IMP 486 were as good as or better than IMP 485 kits (Table 19) when labeled in saline. This high efficiency of radiolabeling with chelator preloaded with aluminum was not observed with any of the other Al-NOTA complexes tested (data not shown). The equivalency of labeling in saline and in 1:1 ethanol/water the labeling yields was also not observed with other chelating moieties (not shown).

TABLE 20

IMP 486 Labeling

| Peptide 20 nmol | Volume Saline | Volume EtOH | Activity at start mCi | Activity of isolated product mCi | % Yield | Specific Activity Ci/mmol |
|---|---|---|---|---|---|---|
| IMP486 | 100 µL | 0 | 46 | 28 | 76 | 2800 |
| IMP485 | 100 µL | 100 µL | 41 | 25 | 83 | |
| IMP486 | 100 µL | 100 µL | 43 | 22 | 81 | |
| IMP486 | 200 µL | 0 | 42 | 18 | 73 | |

Effect of Bulking Agents

An experiment was performed to compare yield using IMP 485 kits (40 nmol) with different bulking agents. The peptide was labeled with 2 mCi of F-18 from the same batch of F-18 in 200 microliters saline. The bulking agents were introduced in water at a concentration of 5% by weight, with a dose of 200 microliters/vial. We tested sorbitol, trehalose, sucrose, mannitol and glycine as bulking agents. Results are shown in Table 20

TABLE 21

Effects of Bulking Agents on Radiolabeling Yield

| Bulking Agent | Activity mCi | Yield % |
|---|---|---|
| Sorbitol | 2.17 | 82.9 |
| Glycine | 2.17 | 41.5 |
| Mannitol | 2.11 | 81.8 |
| Sucrose | 2.11 | 66.1 |
| Trehalose | 2.10 | 81.3 |

Sorbitol, mannitol and trehalose all gave radiolabeled product in the same yield. The sucrose kit and the glycine kit both had significantly lower yields. Trehalose was formulated into IMP 485 kits at concentrations ranging from 2.5% to 50% by weight when reconstituted in 200 µL. The same radiolabeling yield, ~83%, was obtained for all concentrations, indicating that the $^{18}F$-radiolabeling of IMP 485 was not sensitive to the concentration of the trehalose bulking agent. IMP 485 kits were formulated and stored at 2-8° C. under nitrogen for up to three days before lyophilization to assess the impact of lyophilization delays on the radiolabeling. The radiolabeling experiments indicated that yields were all ~80% at time zero, and with 1, 2, and 3 days of delay before lyophilization.

Effect of pH on Radiolabeling

The effect of pH on radiolabeling of IMP 485 is shown in Table 21. The efficiency of labeling was pH sensitive and decreased at either higher or lower pH relative to the optimal pH of about 4.0.

TABLE 22

Effect of pH on IMP 485 Radiolabeling Efficiency.

| pH | Yield % |
|---|---|
| 3.27 | 33 |
| 3.53 | 61 |
| 3.84 | 85 |
| 3.99 | 88 |
| 4.21 | 89 |
| 4.49 | 80 |
| 5.07 | 14 |

Biodistribution

Biodistribution studies were performed in Taconic nude mice bearing subcutaneous LS174T tumor xenografts.

Al$^{18}$F-IMP 485 alone: Mice bearing sc LS174T xenografts were injected with Al$^{18}$F-IMP 485 (28 µCi, 5.2×10$^{-11}$ mol, 100 µL, iv). Mice were necropsied at 1 and 3 h post injection, 6 mice per time point.

TF2+Al$^{18}$F-IMP 485 Pretargeting at 20:1 bsMab to peptide ratio: Mice bearing sc LS174T xenografts were injected with TF2 (163.2 µg, 1.03×10$^{-9}$ mol, iv) and allowed 16.3 h for clearance before injecting Al$^{18}$F-IMP 485 (28 µCi, 5.2×10$^{-11}$ mol, 100 µL, iv). Mice were necropsied at 1 and 3 h post injection, 7 mice per time point.

TABLE 23

Biodistribution of TF2 pretargeted Al$^{18}$F[IMP 485] or Al$^{18}$F[IMP 485] alone at 1 and 3 h after peptide injection in nude mice bearing LS174T human colonic cancer xenografts.

| | Percent-injected dose per gram tissue (mean ± SD; N = 7) | | | |
|---|---|---|---|---|
| | TF2 pregargeted Al$^{18}$F[IMP485] | | Al$^{18}$F[IMP485] alone | |
| Tissue | 1 h | 3 h | 1 h | 3 h |
| Tumor | 28.09 ± 4.55 | 26.52 ± 5.97 | 0.32 ± 0.11 | 0.09 ± 0.02 |
| Liver | 0.24 ± 0.04 | 0.14 ± 0.02 | 0.18 ± 0.03 | 0.10 ± 0.05 |
| Spleen | 0.25 ± 0.11 | 0.25 ± 0.11 | 0.21 ± 0.18 | 0.07 ± 0.01 |
| Kidney | 3.19 ± 0.73 | 2.22 ± 0.22 | 3.33 ± 0.56 | 2.27 ± 0.29 |
| Lung | 0.54 ± 0.15 | 0.24 ± 0.06 | 0.24 ± 0.05 | 0.07 ± 0.02 |
| Blood | 0.28 ± 0.07 | 0.02 ± 0.01 | 0.17 ± 0.06 | 0.09 ± 0.01 |
| Stomach | 0.53 ± 1.18 | 0.03 ± 0.02 | 0.13 ± 0.11 | 0.04 ± 0.02 |
| Sm. Int. | 0.69 ± 0.88 | 0.07 ± 0.03 | 0.40 ± 0.13 | 0.14 ± 0.03 |
| Lg. Int. | 0.10 ± 0.03 | 0.35 ± 0.16 | 0.08 ± 0.02 | 0.71 ± 0.22 |
| Muscle | 0.14 ± 0.10 | 0.03 ± 0.01 | 0.11 ± 0.08 | 0.01 ± 0.01 |
| Scapula | 0.5 ± 0.45 | 0.06 ± 0.02 | 0.11 ± 0.02 | 0.03 ± 0.01 |

Synthesis of IMP 492 (Al$^{19}$FIMP485)

IMP485 (16.5 mg, 0.013 mmol) was dissolved in 1 mL of 2 mM NaOAc, pH 4.43, 0.5 mL ethanol and treated with AlF$_3$.3H$_2$O (2.5 mg, 0.018 mmol). The pH was adjusted to 4.5-5.0 and the reaction mixture was refluxed for 15 minutes. On cooling the pH was once again raised to 4.5-5.0 and the reaction mixture refluxed for 15 minutes. The crude was purified by preparative RP-HPLC to yield a white solid (10.3 mg).

Synthesis of IMP 490

(SEQ ID NO: 38)
NODA-MPAA-D-Phe-Cys-Phe-D-Trp-Lys-Thr-Cys-Throl

The peptide was synthesized on threoninol resin with the amino acids added in the following order: Fmoc-Cys(Trt)-OH, Fmoc-Thr(But)-OH, Fmoc-Lys(Boc)-OH, Fmoc-D-Trp(Boc)-OH, Fmoc-Phe-OH, Fmoc-Cys(Trt)-OH, Fmoc-D-Phe-OH and (tBu)$_2$NODA-MPAA. The peptide was then cleaved and purified by preparative RP-HPLC. The peptide was cyclized by treatment of the bis-thiol peptide with DMSO.

Synthesis of IMP 491 (Al$^{19}$FIMP490)

The Al$^{19}$FIMP490 was prepared as described above (IMP492) to produce the desired peptide after HPLC purification.

Synthesis of IMP 493

(SEQ ID NO: 39)
NODA-MPAA-(PEG)$_3$-Gln-Trp-Ala-Val-Gly-His-Leu-Met-NH$_2$

The peptide was synthesized on Sieber amide resin with the amino acids added in the following order: Fmoc-Met-OH, Fmoc-Leu-OH, Fmoc-His(Trt)-OH, Fmoc-Gly-OH, Fmoc-Val-OH, Fmoc-Ala-OH, Fmoc-Trp(Boc)-OH, Fmoc-Gln (Trt)-OH, Fmoc-NH-(PEG)$_3$—COOH and (tBu)$_2$NODA-MPAA. The peptide was then cleaved and purified by preparative RP-HPLC.

Synthesis of IMP 494 (Al$^{19}$FIMP493)

The Al$^{19}$FIMP493 was prepared as described above (IMP492) to produce the desired peptide after HPLC purification.

Example 33

Other Prosthetic Group Labeling Methods using Al$^{18}$F or Al$^{19}$F

In certain embodiments, the aluminum fluoride labeling method may be performed using prosthetic group labeling methods for molecules that are sensitive to heat. Prosthetic group conjugation may be carried out at lower temperatures for heat-sensitive molecules.

The prosthetic group NOTA is labeled with $^{18}$F or $^{19}$F as described above and then it is attached to the targeting molecule. In one non-limiting example, this is performed with an aldehyde NOTA that is then attached to an amino-oxy compound on a targeting molecule. Alternatively an amino-oxy maleimide is reacted with the aldehyde and then the maleimide is attached to a cysteine on a targeting molecule (Toyokuni et al., 2003, Bioconj Chem 14:1253).

In another alternative, the AlF-chelator complexes are attached to targeting molecules through click chemistry. The ligands are first labeled with Al$^{18}$F or Al$^{19}$F as discussed above. The AlF-chelator is then conjugated to a targeting molecule through a click chemistry reaction. For example, an alkyne NOTA is labeled according to Marik and Stucliffe (2006, Tetrahedron Lett 47:6681) and conjugated to an azide containing targeting agent.

Radiolabeling of Kits with $^{18}$F$^-$ in Saline

The $^{18}$F (0.01 mCi or higher) is received in 200 μL of saline in a 0.5 mL syringe and the solution is mixed with 200 μL of ethanol and injected into a lyophilized kit as described above. The solution is heated in the crimp sealed container at 100-110° C. for 15 min. The solution is diluted with 3 mL water and eluted through an HLB cartridge. The reaction vial and the cartridge are washed with 2×1 mL portions of water and then the product is eluted into a vial containing buffered ascorbic acid using 1:1 ethanol water in 0.5 mL fractions. Some of the ethanol may be evaporated off under a stream of inert gas. The solution is then diluted in saline and passed through a 0.2 μm sterile filter prior to injection.

Example 34

Maleimide Conjugates of NOTA for $^{18}$F Labeling

Figure 15:
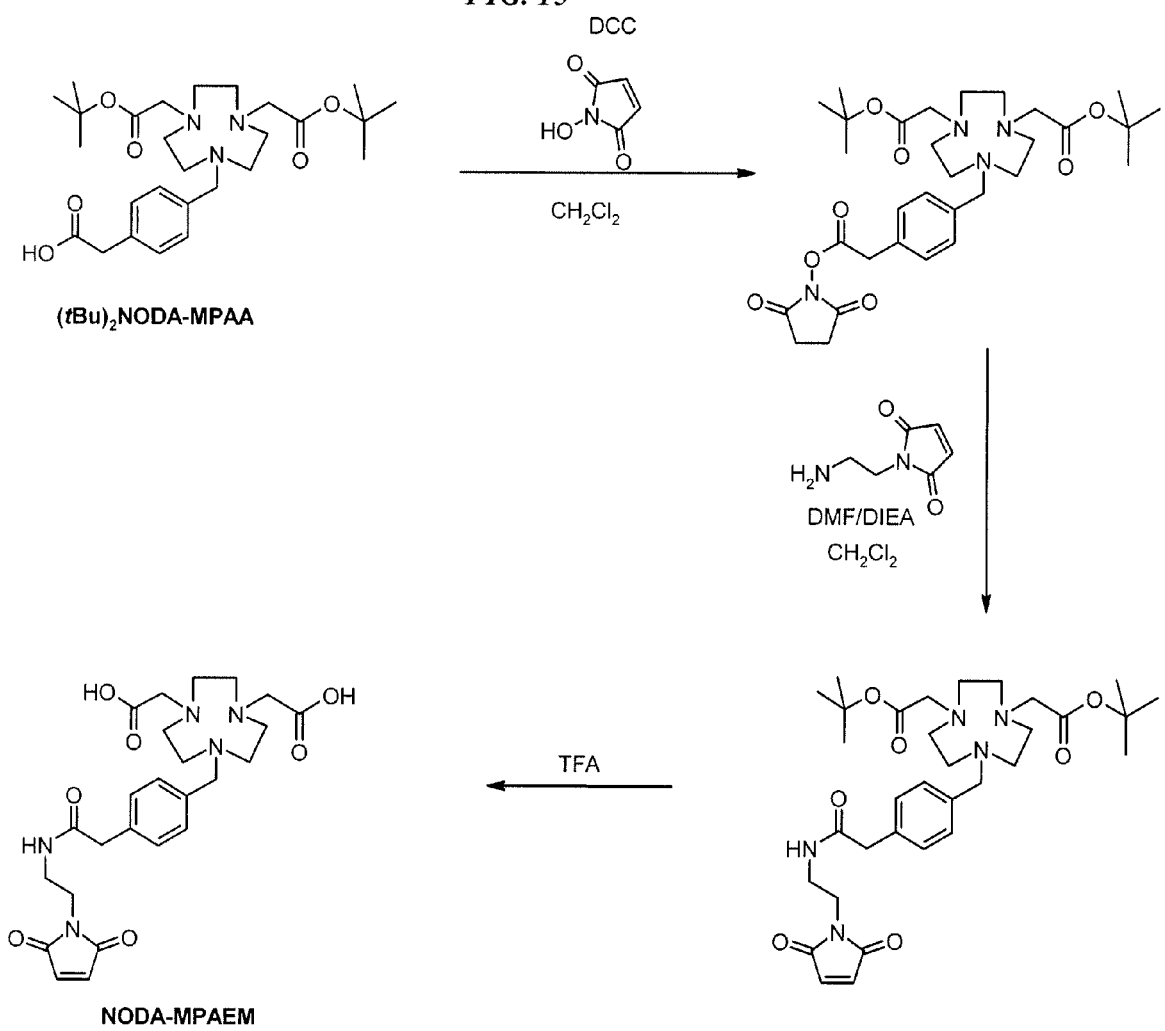
FIG. 15. Synthesis of maleimide conjugate of NOTA.

As discussed above, in certain embodiments a maleimide derivative of NOTA may be of use for low-temperature labeling of molecules. An exemplary method of preparing maleimide-derivatized NOTA is discussed below. Details are shown in FIG. 15.

Synthesis of Bis-t-butyl-NODA-MPAA NHS ester: (tBu)$_2$NODA-MPAA NHS ester

To a solution of (tBu)$_2$NODA-MPAA (175.7 mg, 0.347 mmol) in CH$_2$Cl$_2$ (5 mL) was added 347 μL (0.347 mmol) DCC (1 M in CH$_2$Cl$_2$), 42.5 mg (0.392 mmol) N-hydroxysuccinimide (NHS), and 20 μL N,N-diisopropylethylamine (DIEA). After 3 h DCU was filtered off and solvent evaporated. The crude mixture was purified by flash chromatography on (230-400 mesh) silica gel (CH$_2$Cl$_2$:MeOH::100:0 to 80:20) to yield (128.3 mg, 61.3%) of the NHS ester. The HRMS (ESI) calculated for C$_{31}$H$_{46}$N$_4$O$_8$ (M+H)$^+$ was 603.3388, observed was 603.3395.

Synthesis of NODA-MPAEM: (MPAEM=methyl phenyl acetamido ethyl maleimide)

To a solution of (tBu)$_2$NODA-MPAA NHS ester (128.3 mg, 0.213 mmol) in CH$_2$Cl$_2$ (5 mL) was added a solution of 52.6 mg (0.207 mmol) N-(2-aminoethyl) maleimide trifluoroacetate salt in 250 μL DMF and 20 μL DIEA. After 3 h the solvent was evaporated and the concentrate was treated with 2 mL TFA. The crude product was diluted with water and purified by preparative RP-HPLC to yield (49.4 mg, 45%) of the desired product. HRMS (ESI) calculated for C$_{25}$H$_{33}$N$_5$O$_7$ (M+H)$^+$ was 516.2453, observed was 516.2452.

$^{18}$F-Labeling of NODA-MPAEM

To 10 μL (20 nmol) 2 mM NODA-MPAEM solution was added 5 μL 2 mM AlCl$_3$, 40 μL $^{18}$F$^-$ solution [2.41 mCi, Na$^{18}$F, PETNET] followed by 50 μL CH$_3$CN and heated to 110° C. for 15 minutes. The crude reaction mixture was purified by transferring the resultant solution into a OASIS® HLB 1 cc (30 mg) cartridge and eluting with DI H$_2$O to remove unbound $^{18}$F$^-$ followed by 1:1 EtOH/H$_2$O to elute the $^{18}$F-labeled peptide. The crude reaction solution was pulled through the HLB cartridge into a 5 mL vial and the cartridge washed with 3×1 mL fractions of DI H$_2$O (49.9 μCi). The HLB cartridge was then placed on a new 3 mL vial and eluted with 4×200 μL 1:1 EtOH/H$_2$O to collect the labeled peptide (0.978 mCi). The reaction vessel retained 7.73 μCi, while the cartridge retained 22.1 μCi of activity.

0.978 mCi⇒92.5% of Al$^{18}$F(NODA-MPAEM).

Example 34

Preparation and Labeling of hMN14 F(ab')$_2$

Pepsin Digestion—To 90 ml of 9.8 mg/ml hMN14 IgG C/N 0206078 (Total 882 mg), added 9.0 ml of 0.1 M Citrate, pH 3.5 buffer, adjusted to pH 3.7 with 1M citric acid, added 1.2 ml of 1 mg/ml pepsin in 0.1 M citrate, pH 3.5 buffer (final conc. of pepsin was 12 μg/ml). The mixture was incubated at 37° C. for 40 min. Digestion was monitored by SE-HPLC and the reaction was stopped by adding 10% of 3M Tris, pH 8.6

Purification—Was performed on a protein A column (2.5×8 cm, 40 mL). The flowthrough (150 ml) was collected, containing an unbound F(ab')$_2$ peak. The F(ab')$_2$ was filtered through a 0.22 um filter. The final concentration was 15 mg/ml (33 ml, total 500 mg). A second step involved Q-SEPHAROSE® column chromatography (1×20, 16 mL). The protein A purified hMN14 F(ab')$_2$ was concentrated and dialfiltered into 0.02 M Tris, 0.01M NaCl, pH 8.5, with a 30K stir cell. The F(ab')$_2$ was loaded onto a Q-SEPHAROSE® column. The flow-through peak was collected and fractions 3 and 4 were pooled, concentrated and dilfiltered into 0.04 M PBS, pH 7.4. After filtration using a 0.22 um filter, the final concentration was 5.5 mg/ml, 40 mL, total 220 mg of protein.

Preparation of lyophilized hMN14 Fab'SH—TCEP reduction was performed as follows. To 3.8 mL of 5.5 mg/mL hMN14F(ab')$_2$ (total 20.9 mg) was added 0.38 mL of 20 mM TCEP-HCl diluted in PBS. The mixture was incubated at room temp for 2 hours and the reduction was monitored by SE-HPLC. The Fab'SH was concentrated and dialfiltered into formulation buffer (0.025M NaOAc, 5% trehalose, pH 6.7) with a 10K stir cell. About 80 mL buffer was used. The antibody was filtered through a 0.22 um filter. The final concentration was 2.3 mg/mL (9 mL, total 20.7 mg). The thiol content per antibody was determined by Elman's assay to be 2.4 SH/Fab. Lyophilization was performed using 0.45 mL (1 mg protein) per vial.

$^{18}$F-Labeling—The lypophilized hMN-14 Fab' was dissolved in 100 µL 20 mM PBS, pH 7.01. NODA-MPAEM was labeled with 20 nmol of $^{18}$F. Then 600 µL of F-18 NODA-MPAEM in 1:1 EtOH/H$_2$O was added to the Fab' vial and the mixture was incubated at RT for 10 min, then purified on a SEPHADEX® G50-80 spin column. About 80% of the added activity (80% yield) was eluted from a spin column as labeled antibody. Almost all the activity shifted by SEC after addition of CEA, indicating that the label was associated with the antibody Fab' fragment.

What is claimed is:

1. A method of labeling a molecule with $^{18}$F or $^{19}$F comprising attaching a complex of $^{18}$F or $^{19}$F and a group IIIA metal to a chelating moiety, wherein the chelating moiety is conjugated to the molecule or the chelating moiety is later attached to the molecule, wherein the chelating moiety is NODA-MPAA or NODA-MPAEM

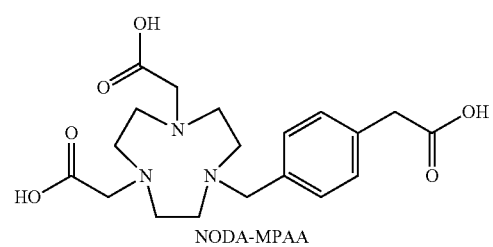

NODA-MPAA

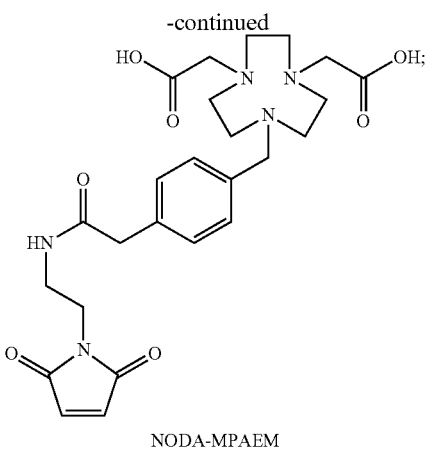

NODA-MPAEM

2. The method of claim 1, wherein the chelating moiety is conjugated to the molecule.

3. The method of claim 1, wherein the chelating moiety is later attached to the molecule and the method further comprises attaching the chelating moiety to the molecule.

4. The method of claim 1, wherein the molecule is a protein or peptide.

5. The method of claim 1, wherein the molecule is a targeting molecule selected from the group consisting of an antibody, a monoclonal antibody, a bispecific antibody, a multispecific antibody, an antibody fusion protein and an antigen-binding antibody fragment.

6. The method of claim 5, wherein the chelating moiety is conjugated to a targetable construct.

7. The method of claim 6, further comprising:
c) administering the targeting molecule to a subject;
d) allowing sufficient time for the targeting molecule to bind to a target antigen; and
e) subsequently administering the targetable construct to the subject, wherein the targetable construct binds to the targeting molecule.

8. The method of claim 1, wherein the group IIIA metal is selected from the group consisting of aluminum, gallium, indium, and thallium.

9. The method of claim 1, wherein the group IIIA metal is aluminum.

10. The method of claim 6, wherein the targetable construct is selected from the group consisting of IMP 485, IMP 490, IMP 491, IMP 492, IMP 493 and IMP 494.

11. The method of claim 1, wherein the $^{18}$F or $^{19}$F labeled molecule is produced in less than 30 minutes from the start of the method.

12. The method of claim 7, further comprising using PET scanning to image the distribution of the $^{18}$F-labeled molecule in the subject.

13. The method of claim 1, wherein the $^{18}$F or $^{19}$F complex is attached to the chelating moiety in an aqueous medium.

14. The method of claim 1, wherein an organic solvent is added to the medium to attach the $^{18}$F or $^{19}$F complex to a chelating moiety.

15. The method of claim 1, wherein the $^{18}$F or $^{19}$F complex is attached to the chelating moiety by microwave irradiation.

16. The method of claim 1, wherein the $^{18}$F or $^{19}$F complex is attached to the chelating moiety by heating.

17. The method of claim 5, wherein the targeting molecule is prepared by the dock-and-lock technique.

18. The method of claim 17, wherein the targeting molecule is TF2 or TF10.

19. The method of claim 3, wherein the chelating moiety is attached to the molecule by a maleimide-sulfhydryl reaction.

20. The method of claim 6, wherein the yield of radiolabeled targetable construct is at least 85%.

21. The method of claim 6, wherein the specific radioactivity of the targetable construct is at least 115 GBq/μmol.

22. The method of claim 6, wherein the targetable construct is lyophilized for storage before radiolabeling.

23. The method of claim 22, wherein the targetable construct is lyophilized in a bulking agent selected from the group consisting of sorbitol, mannitol and trehalose.

24. The method of claim 1, wherein the chelating moiety is attached to the $^{18}$F or $^{19}$F complex at a pH between 3.8 and 4.5.

25. The method of claim 7, wherein the targeting molecule binds to a diseased cell and further comprising detecting, diagnosing, or imaging the presence of a disease by PET imaging of the $^{18}$F-labeled molecule or NMR imaging of the $^{19}$F-labeled molecule wherein the disease is selected from the group consisting of fungi, viruses, parasites, bacteria, human immunodeficiency virus (HIV), herpes virus, cytomegalovirus, rabies virus, influenza virus, hepatitis B virus, Sendai virus, feline leukemia virus, Reovirus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, *Streptococcus agalactiae, Legionella pneumophila, Streptococcus pyogenes, Escherichia coli, Neisseria gonorrhoeae, Neisseria meningitidis, Pneumococcus, Hemophilus influenzae* B, *Treponema pallidum*, Lyme disease spirochetes, *Pseudomonas aeruginosa, Mycobacterium leprae, Brucella abortus, Mycobacterium tuberculosis, Clostridium tetani*, immune-mediated thrombocytopenia, acute idiopathic thrombocytopenic purpura, chronic idiopathic thrombocytopenic purpura, dermatomyositis, Sjogren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis obliterans, primary biliary cirrhosis, Hashimoto's thyroiditis, thyrotoxicosis, scleroderma, chronic active hepatitis, polymyositis/dermatomyositis, polychondrifis, pemphigus vulgaris, Wegener's granulomatosis, membranous nephropathy, amyotrophic lateral sclerosis, tabes dorsalis, giant cell arteritis/polymyalgia, pernicious anemia, glomerulonephritis, and fibrosing alveolitis.

26. The method of claim 7, wherein the targeting molecule binds to an antigen selected from the group consisting of carbonic anhydrase IX, CCCL19, CCCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CXCR4, CXCR7, CXCL12, HIF-1α, AFP, PSMA, CEACAM5, CEACAM-6, c-met, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN- α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, P1GF, complement factors C3, C3a, C3b, C5a, and C5.

27. The method of claim 25, wherein the targeting molecule is an antibody selected from the group consisting of hR1 (anti-IGF-1R), hPAM4 (anti-pancreatic cancer mucin), hA20 (anti-CD20), hA19 (anti-CD19), hIMMU31 (anti-AFP), hLL1 (anti-CD74), hLL2 (anti-CD22), hMu-9 (anti-CSAp), hL243 (anti-HLA-DR), hMN-14 (anti-CEACAM5), hMN-15 (anti-CEACAM6), hRS7 (anti-EGP-1) and hMN-3 (anti-CEACAM6).

28. A targetable construct comprising a chelating moiety attached to metal-$^{18}$F, metal-$^{19}$F or $^{68}$Ga, wherein the chelating moiety is NODA-MPAA or NODA-MPAEM

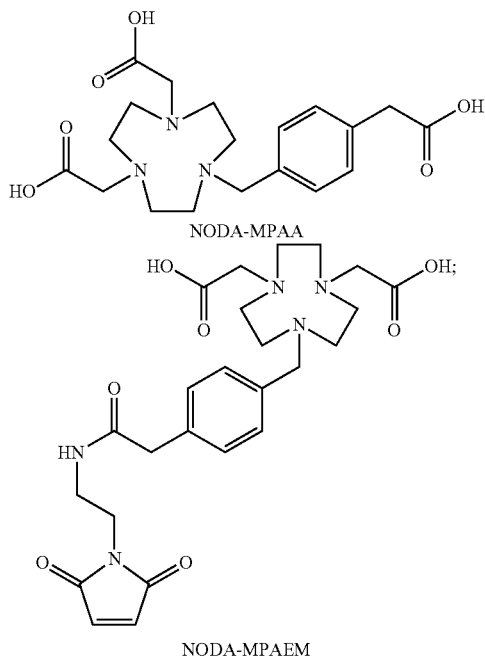

NODA-MPAA

NODA-MPAEM

29. The targetable construct of claim 28, wherein the targetable construct is selected from the group consisting of IMP 485, IMP 490, IMP 491, IMP 492, IMP 493 and IMP 494.

30. A composition comprising NODA-MPAA or NODA-MPAEM

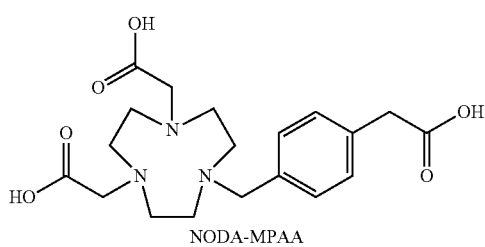

NODA-MPAA

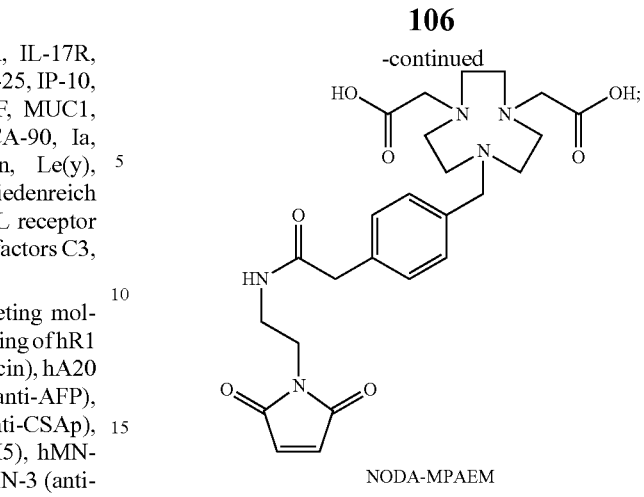

NODA-MPAEM

31. The composition of claim 30, wherein the NODA-MPAA or NODA-MPAEM is conjugated to a molecule.

32. The composition of claim 30, wherein the NODA-MPAA or NODA-MPAEM is complexed with a metal-$^{18}$F.

33. The composition of claim 30, wherein the NODA-MPAA or NODA-MPAEM is complex with Al-$^{18}$F.

34. The composition of claim 30, wherein the NODA-MPAA or NODA-MPAEM is complexed with $^{68}$Ga.

35. A method of labeling a molecule with $^{18}$F or $^{19}$F comprising:
 a) attaching a group IIIA metal to a chelating moiety in aqueous medium to form a metal-chelating moiety complex, wherein the chelating moiety is conjugated to the molecule or the chelating moiety is later attached to the molecule, wherein the chelating moiety is NODA-MPAA or NODA-MPAEM

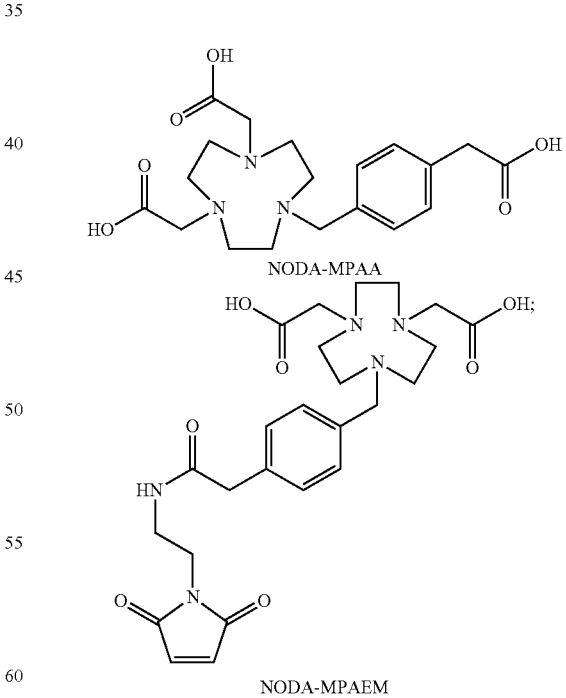

NODA-MPAA

NODA-MPAEM and
 b) adding $^{18}$F or $^{19}$F to the metal-chelating moiety complex, wherein the $^{18}$F or $^{19}$F binds to the metal.

36. The method of claim 19, wherein the chelating moiety is NODA-MPAEM.

37. The method of claim 36, wherein the complex of $^{18}$F or $^{19}$F and a group IIIA metal is attached to the chelating moiety by heating, before the chelating moiety is conjugated to the molecule.

38. The method of claim 37, wherein the molecule is heat sensitive.

39. The composition of claim 31, wherein the molecule is a protein or peptide.

40. The composition of claim 39, wherein the protein or peptide is selected from the group consisting of IMP 485, IMP 486, IMP 487, IMP 490, IMP 491, IMP 492 and IMP 493.

41. The composition of claim 30, further comprising a bulking agent selected from the group consisting of sorbitol, mannitol or trehalose.

42. The composition of claim 41, wherein the bulking agent is trehalose.

43. The composition of claim 30, further comprising ascorbic acid.

44. The composition of claim 30, further comprising $AlCl_3$.

45. The composition of claim 30, further comprising an organic solvent.

46. The composition of claim 30, wherein the organic solvent is selected from the group consisting of ethanol, methanol, acetonitrile, IPA, acetone, THF, dioxane, DMF and DMSO.

47. The composition of claim 30, wherein the organic solvent is ethanol.

48. The composition of claim 30, further comprising saline.

49. The composition of claim 31, wherein the NODA-MPAA or NODA-MPAEM is complexed with a metal-$^{18}$F.

50. The composition of claim 49, wherein the metal-$^{18}$F labeled molecule has a specific activity of 2,500 Ci/mmol or higher.

51. The composition of claim 31, wherein the NODA-MPAA or NODA-MPAEM is complexed with a metal-$^{19}$F.

52. The composition of claim 31, wherein the NODA-MPAA or NODA-MPAEM is complexed with $^{68}$Ga.

53. The composition of claim 31, wherein the molecule is heat sensitive.

54. The composition of claim 31, wherein the NODA-MPAEM is attached to the molecule by a maleimide-sulfhydryl reaction.

* * * * *